United States Patent
Galbraith et al.

(10) Patent No.: US 6,756,227 B1
(45) Date of Patent: Jun. 29, 2004

(54) PORCINE RETROVIRUS

(75) Inventors: Daniel Norman Galbraith, Glasgow (GB); Christine Haworth, Broomhill (GB); Gillian Margaret Lees, Newton Mearns (GB); Kenneth Thomas Smith, Newton Mearns (GB)

(73) Assignee: Quip Technology, Limited, Glasgow (GB)

( * ) Notice: Subject to any disclaimer, the term of this patent is extended or adjusted under 35 U.S.C. 154(b) by 0 days.

(21) Appl. No.: 09/171,553

(22) PCT Filed: Apr. 18, 1997

(86) PCT No.: PCT/GB97/01087

§ 371 (c)(1),
(2), (4) Date: Feb. 8, 1999

(87) PCT Pub. No.: WO97/40167

PCT Pub. Date: Oct. 30, 1997

(30) Foreign Application Priority Data

Apr. 19, 1996 (GB) .............................. 9608164
Feb. 10, 1997 (GB) .............................. 9702668

(51) Int. Cl.[7] .................. C12N 5/00; C12N 1/20; C12N 15/63; C07H 21/02; C07H 21/04
(52) U.S. Cl. ............... 435/325; 435/320.1; 435/252.1; 536/23.1
(58) Field of Search .......................... 435/320.1, 325; 536/22.1; 424/93.1

(56) References Cited

U.S. PATENT DOCUMENTS 6,033,905 A * 3/2000 Eiden et al. ............ 435/320.1

6,190,861 B1  2/2001 Fishman ................... 435/4

FOREIGN PATENT DOCUMENTS

WO    WO 97/21836    6/1997

OTHER PUBLICATIONS

SEQ ID No. 3 Patent No. 6190861, Feb. 20, 2001.*
Smith et al. Accession No AW657531, 05–04–200.*
Rudinger J in Peptide Hormones. Editor Parsons JA, pp. 1–7, 1976, University Park Press, Baltimore.*
Patience et al.; "Infection Of Human Cells By An Endogenous Retrovirus Of Pigs", Nature Medicine, vol. 3, No. 3, pp. 282–286, Mar. 1997.
John M. Coffin; "The Dangers Of Xenotransplantation", Letters To Editor, Nature Medicine, vol. 1, No. 11, p. 1100, Nov. 1995.

* cited by examiner

Primary Examiner—Ram R. Shukla
(74) Attorney, Agent, or Firm—Foley Hoag LLP

(57) ABSTRACT

The present invention provides porcine retrovirus (PoEV) polynucleotide fragments, particularly those encoding at least one PoEV expression product, a recombinant vector comprising such a polynucleotide fragment or fragments, use of PoEV polynucleotide fragments in the detection of native PoEV, a host cell containing at least one PoEv polynucleotide fragment or recombinant vector, PoEV polypeptides, antibodies immuno-reactive with PoEV polypeptides, pharmaceutical compositions comprising recombinant PoEV polypeptides for use as prophylactic and/or therapeutic agents and uses of PoEV polynucleotide fragments and/or polypeptides in medicine, including veterinary medicine and in the preparation of medicaments for use in medicine.

8 Claims, 22 Drawing Sheets

Figure 1

```
   1 GAATTCGCGGCCGCGTCGACAGATGCCTTCTTCTGCCTGAGATTACACCCCACTAGCCAA   60
  61 CCACTTTTTGCCTTCGAATGGAGAGATCCAGGTACGGGAAGAACCGGGCAGCTCACCTGG  120
 121 ACCCGACTGCCCCAAGGGTTCAAGAACTCCCCGACCATCTTTGACGAAGCCCTACACAGG  180
 181 GACCTGGCCAACTTCAGGATCCAACACCCTCAGGTGACCCTCCTCCAGTACGTGGATGAC  240
 241 CTGCTTCTGGCGGGAGCCACCAAACAGGACTGCTTAGAAGGTACGAAGGCACTACTGCTG  300
 301 GAATTGTCTGACCTAGGCTACAGAGCCTCTGCTAAGAAGGCCCAGATTTGCAGGAGAGAG  360
 361 GTAACATACTTGGGGTACAGTTTGCGGGGCGGGCAGCGATGGCTGACGGAGGCACGGAAG  420
 421 AAAACTGTAGTCCAGATACCGGCCCCAACCACAGCCAAACAAGTGAGAGAGTTTTTGGGG  480
 481 ACAGCTGGATTTTGCAGACTGTGGATCCGGGGTTTGCGACCTTAGCAGCCCCACTCTAC  540
 541 CCGCTAACCAAAGAAAAGGGGGATTCTCCTGGGCTCCTGAGCACCAGAAGGCATTTGAT  600
 601 GCTATCAAAAAGGCCCTGCTGAGCGCACCTGCTCTGGCCCTCCCTGACGTAACTAAACCC  660
 661 TTTACCCTTTATGTGGATGAGCGTAAGGGAGTAGCCCGAGGAGTTTTAACCCAAACCCTA  720
 721 GGACCATGGAGGAGACCTGTTGCCTACCTGTCAAAGAAGCTTGATCCTGTAGCCAGTGGT  780
 781 TGGCCCGTATGTCTGAAGGCTATCGCAGCTGTGGCCATACTGGTCAAGGACGCTGACAAA  840
 841 TTGACTTTGGGACAGAATATAACTGTAATAGCCCCCCATGCATTGGAGAACATCGTTCGG  900
 901 CAGCCCCCAGACCGATGGATGACCAACGCCCGCATGACCCACTATCAAAGCCTGCTTCTC  960
 961 ACAGAGAGGGTCACTTTCGCTCCACCAGCCGCTCTCAACCCTGCCACTCTTCTGCCTGAA 1020
1021 GAGACTGATGAACCAGTGACTCATGATTGCCATCAACTATTGATTGAGGAGACTGGGGTC 1080
1081 CGCAAGGACCTTACAGACATACCGCTGACTGGAGAAGTGCTAACCTGGTTCACTGACGGA 1140
1141 AGCAGCTATGTGGTGGAAGGTAAGAGGATGGCTGGGCGGCAGTGGTGGACGGGACCCGC 1200
1201 ACGATCTGGGCCAGCAGCCTGCCGGAAGGAACTTCAGCGCAAAAGGCTGAGCTCATGGCC 1260
```

Figure 1 cont.

```
1261  CTCACGCAAGCTTTGCGGCTGGCCGAAGGGAAATCCATAAACATTTATACGGACAGCAGG  1320
1321  TATGCCTTTGCGACTGCACACGTACACGGGGCCATCTATAAACAAAGGGGGTTGCTTACC  1380
1381  TCAGCAGGGAGGGAAATAAAGAACAAAGAGGAAATTCTAAGCCTATTAGAAGCCTTACAT  1440
1441  TTGCCAAAAAGGCTAGCTATTATACACTGTCCTGGACATCAGAAAGCCAAAGATCTCATA  1500
1501  TCTAGAGGGAACCAGATGGCTGACCGGGTTGCCAAGCAGGCAGCCCAGGCTGTTAACCTT  1560
1561  CTGCCTATAATAGAAACGCCCAAAGCCCCAGAACCCAGACGACAGTACACCCTAGAAGAC  1620
1621  TGGCAAGAGATAAAAAAGATAGACCAGTTCTCTGAGACTCCGGAGGGGACCTGCTATACC  1680
1681  TCATATGGGAAGGAAATCCTGCCCCACAAAGAAGGGTTAGAATATGTCCAACAGATACAT  1740
1741  CGTCTAACCCACCTAGGAACTAAACACCTGCAGCAGTTGGTCAGAACATCCCCTTATCAT  1800
1801  GTTCTGAGGCTACCAGGAGTGGCTGACTCGGTGGTCAAACATTGTGTGCCCTGCCAGCTG  1860
1861  GTTAATGCTAATCCTTCCAGAATACCTCCAGGAAAGAGACTAAGGGGAAGCCACCCAGGC  1920
1921  GCTCACTGGGAAGTGGACTTCACTGAGGTAAAGCCGGCTAAATACGGAAACAAATATCTA  1980
1981  TTGGTTTTTGTAGACACCTTTTCAGGATGGGTAGAGGCTTATCCTACTAAGAAAGAGACT  2040
2041  TCAACCGTGGTGGCTAAGAAAATACTGGAGGAAATTTTTCCAAGATTTGGAATACCTAAG  2100
2101  GTAATAGGGTCAGACAATGGTCCAGCTTTCGTTGCCCAGGTAAGTCAGGGACTGGCCAAG  2160
2161  ATATTGGGGATTGATTGGAAACTGCATTGTGCATACAGACCCCAAAGCTCAGGACAGGTA  2220
2221  GAGAGGATGAATAGAACCATTAAAGAGACCCTTACCAAATTGACCACAGAGACTGGCATT  2280
2281  AATGATTGGATGGCTCTCCTGCCCTTTGTGCTTTTAGGGTGAGGAACACCCCTGGACAG  2340
2341  TTTGGGCTGACCCCCTATGAATTGCTCTACGGGGACCCCCCCGTTGGCAGAAATTGCC  2400
2401  TTTGCACATAGTGCTGATGTGCTGCTTTCCCAGCCTTTGTTCTCTAGGCTCAAGGCGCTC  2460
2461  GAGTGGGTGAGGCAGCGAGCGTGGAAGCAGCTCCGGGAGGCCTACTCAGGAGGAGACTTG  2520
```

Figure 1 cont.

```
2521 CAAGTTCCACATCGCTTCCAAGTTGGAGATTCAGTCTATGTTAGACGCCACCGTGCAGGA  2580

2581 AACCTCGAGACTCGGTGGAAGGGACCTTATCTCGTACTTTTGACCACACCAACGGCTGTG  2640

2641 AAAGTCGAAGGAATCCCCACCTGGATCCATGCATCCCACGTTAAGCCGGCGCCACCTCCC  2700

2701 GATTCGGGGTGGAAAGCCGAAAAGACTGAAAATCCCCTTAAGCTTCGCCTCCATCGCGTG  2760

2761 GTTCCTTACTCTGTCAATAACTCCTCAAGTTAATGGTAAACGCCTTGTGGACAGCCCGAA  2820

2821 CTCCCATAAACCCTTATCTCTCACCTGGTTACTTACTGACTCCGGTACAGGTATTAATAT  2880

2881 TAACAGCACTCAAGGGGAGGCTCCCTTGGGGACCTGGTGGCCTGAATTATATGTCTGCCT  2940

2941 TCGATCAGTAATCCCTGGTCTCAATGACCAGGCCACACCCCCGATGTACTCCGTGCTTA  3000

3001 CGGGTTTTACGTTTGCCCAGGACCCCCAAATAATGAAGAATATTGTGGAAATCCTCAGGA  3060

3061 TTTCCTTTGCAAGCAATGGAGCTGCATAACTTCTAATGATGGGAATTGGAAATGGCCAGT  3120

3121 CTCTCAGCAAGACAGAGTAAGTTACTCTTTTGTTAACAATCCTACCAGTTATAATCAATT  3180

3181 TAATTATGGCCATGGGAGATGGAAAGATTGGCAACAGCGGGTACAAAAAGATGTACGAAA  3240

3241 TAAGCAAATAAGCTGTCATTCGTTAGACCTAGATTACTTAAAAATAAGTTTCACTAAAAA  3300

3301 AAAAAAAAAAAAAAAAAAAA  3320
```

Figure 2

```
   1  TGTGGGCCCCAGCGCGCTTGGAATAAAAATCCTCTTGCTGTTTGCATCAAGACCGCTTCT    60
  61  CGTGAGTGATTTGGGGTGTCGCCTCTTCCGAGCCCGGACGAGGGGATTGTTCTTTTACT   120
 121  GGCCTTTCATTTGGTGCGTTGGCCGGGAAATCCTGCGACCACCCCTTACACCCGAGAACC   180
 181  GACTTGGAGGTAAAGGGATCCCCTTTGGAACGTGTGTGTGTCGGCCGGCGTCTCTGTT    240
 241  CTGAGTGTCTGTTTTCGGTGATGCGCGCTTTCGGTTTGCAGCTGTCCTCTCAGACCGTAA   300
 301  GGACTGGAGGACTGTGATCAGCAGACGTGCTAGGAGGATCACAGGCTGCCACCCTGGGGG   360
 361  ACGCCCCGGGAGGTGGGGAGAGCCAGGGACGCCTGGTGGTCTCCTACTGTCGGTCAGAGG   420
 421  ACCGAGTTCTGTTGTTGAAGCGAAAGCTTCCCCCTCCGCGGCCGTCCGACTCTTTTGCCT   480
 481  GCTTGTGGAAGACGCGGACGGGTCGCGTGTGTCTGGATCTGTTGGTTTCTGTCTCGTGTG   540
 541  TCTTTGTCTTGTGCGTCCTTGTCTACAGTTTTAATATGGGACAGACAGTGACTACCCCC    600
 601  TTAGTTTGACTCTCGACCATTGGACTGAAGTTAGATCCAGGGCTCATAATTTGTCAGTTC   660
 661  AGGTTAAGAAGGGACCTTGGCAGACTTTCTGTGCCTCTGAATGGCAACATTCGATGTTG    720
 721  GATGGCCATCAGAGGGGACCTTTAATTCTGAAATTATCCTGGCTGTTAAGGCAATCATTT   780
 781  TTCAGACTGGACCCGGCTCTCATCCTGATCAGGAGCCCTATATCCTTACGTGGCAAGATT   840
 841  TGGCAGAAGATCCTCCGCCATGGGTTAAACCATGGCTAAATAAACCAGAAAGCCAGGTC    900
 901  CCCGAATCCTGGCTCTTGGAGAGAAAAACAAACACTCGGCCGAAAAAGTCGAGCCCTCTT   960
 961  CCTCGTATCTACCCCGAGATCGAGGAGCCGCCGACTTGGCCGGAACCCCAACCTGTTCCC  1020
1021  CCACCCCCTTATCCAGCACAGGGTGCTGTGAGGGGACCTCTGCCCCTCCTGGAGCTCCGG  1080
1081  TGGTGGAGGGACCTGCTGCCGGGACTCGGAGCCGGAGAGGCGCCACCCCGGAGCGGACAG  1140
1141  ACGAGATCGCGATATTACCGCTGCGCACCTATGGCCCTCCCATGCCAGGGGGCCAATTGC  1200
1201  AGCCCCTCCAGTATTGGCCCTTTTCTTCTGCAGATCTCTATAATTGGAAAACTAACCATC  1260
```

Figure 2 cont.

```
1261 CCCCTTTCTCGGAGGATCCCCAACGCCTCACGGGGTTGGTGGAGTCCCTTATGTTCTCTC 1320
1321 ACCAGCCTACTTGGGATGATTGTCAACAGCTGCTGCAGACACTCTTCACAACCGAGGAGC 1380
1381 GAGAGAGAATTCTGTTAGAGGCTAGAAAAAATGTTCCTGGGGCCGACGGGCGACCCACGC 1440
1441 AGTTGCAAAATGAGATTGACATGGGATTTCCCTTGACTCGCCCCGGTTGGGACTACAACA 1500
1501 CGGCTGAAGGTAGGGAGAGCTTGAAAATCTATCGCCAGGCTCTGGTGGCGGGTCTCCGGG 1560
1561 GCGCCTCAAGACGGCCCACTAATTTGGCTAAGGTAAGAGAGGTGATGCAGGGACCGAACG 1620
1621 AACCTCCCTCGGTATTTCTTGAGAGGCTCATGGAAGCCTTCAGGCGGTTCACCCCTTTTG 1680
1681 ATCCTACCTCAGAGGCCCAGAAAGCCTCAGTGGCCCTGGCCTTCATTGGGCAGTCGGCTC 1740
1741 TGGATATCAGGAAGAAACTTCAGAGACTGGAAGGGTTACAGGAGGCTGAGTTACGTGATC 1800
1801 TAGTGAGAGAGGCAGAGAAGGTGTATTACAGAAGGGAGACAGAAGAGGAGAAGGAACAGA 1860
1861 GAAAAGAAAAGGAGAGAGAAGAAAGGGAGGAAAGACGTGATAGACGGCAAGAGAAGAATT 1920
1921 TGACTAAGATCTTGGCCGCAGTGGTTGAAGGGAAGAGCAGCAGGGAGAGAGAGAGAGATT 1980
1981 TTAGGAAAATTAGGTCAGGCCCTAGACAGTCAGGGAACCTGGGCAATAGGACCCCACTCG 2040
2041 ACAAGGACCAGTGTGCGTATTGTAAAGAAAAGGACACTGGGCAAGGAACTGCCCCAAGA 2100
2101 AGGGAAACAAAGGACCGAAGTCCTAGCTCTAGAAGAAGATAAAGATTAGGGGAGACGGGT 2160
2161 TCGGACCCCCTCCCCGAGCCCAGGGTAACTTTGAAGGTGGAGGGGCAACCAGTTGAGTTC 2220
2221 CTGGTTGATACCGGAGCGGAGCATTCAGTGCTGCTACAACCATTAGGAAAACTAAAAGAA 2280
2281 AAAAAATCCTGGGTGATGGGTGCCACAGGGCAACGGCAGTATCCATGGACTACCCGAAGA 2340
2341 ACCGTTGACTTGGGAGTGGGACGGGTAACCCACTCGTTTCTGGTCATCCCTGAGTGCCCA 2400
2401 GTACCCCTTCTAGGTAGAGACTTACTGACCAAGATGGGAGCTCAAATTTCTTTTGAACAA 2460
2461 GGAAGACCAGAAGTGTCTGTGAATAACAAACCCATCACTGTGTTGACCCTCCAATTAGAT 2520
```

Figure 2 cont.

```
2521  GATGAATATCGACTATATTCTCCCCAAGTAAAGCCTGATCAAGATATACAGTCCTGGTTG  2580

2581  GAGCAGTTTCCCCAAGCCTGGGCAGAAACCGCAGGGATGGGTTTGGCAAAGCAAGTTCCC  2640

2641  CCACAGGTTATTCAACTGAAGGCCAGTGCTACACCAGTATCAGTCAGACAGTACCCCTTG  2700

2701  AGTAGAGAGGCTCGAGAAGGAATTTGGCCGCATGTTCAAAGATTAATCCAACAGGGCATC  2760

2761  CTAGTTCCTGTCCAATCCCCTTGGAATACTCCCTGCTACCGGTTAGGAAGCCTGGGACC  2820

2821  AATGATTATCGACCAGTACAGGACTTGAGAGAGGTCAATAAAAGGGTGCAGGACATACAC  2880

2881  CCAACGGTCCCGAACCCTTATAACCTCTTGAGCGCCCTCCCGCCTGAACGGAACTGGTAC  2940

2941  ACAGTATTGGACTTAAAAGATGCCTTCTTCTGCCTGAGATTACACCCCACTAGCCAACCA  3000

3001  CTTTTTGCCTTCGAATGGAGAGATCCAGGTACGGGAAGAACCGGGCAGCTCACCTGGACC  3060

3061  CGACTGCCCCAAGGGTTCAAGAACTCCCCGACCATCTTTGACGAAGCCCTACACAGGGAC  3120

3121  CTGGCCAACTTCAGGATCCAACACCCTCAGGTGACCCTCCTCCAGTACGTGGATGACCTG  3180

3181  CTTCTGGCGGGAGCCATCCAAACAGGACTGCTTAGAAGGTACGAAGGCACTACTGCTGGAA  3240

3241  TTGTCTGACCTAGGCTACAGAGCCTCTGCTAAGAAGGCCCAGATTTGCAGGAGAGAGGTA  3300

3301  ACATACTTGGGGTACAGTTTGCGGGGCGGGCAGCGATGGCTGACGGAGGCACGGAAGAAA  3360

3361  ACTGTAGTCCAGATACCGGCCCCAACCACAGCCAAACAAGTGAGAGAGTTTTTGGGGACA  3420

3421  GCTGGATTTTGCAGACTGTGGATCCCGGGGTTTGCGACCTTAGCAGCCCCACTCTACCCG  3480

3481  CTAACCAAAGAAAAGGGGGATTCTCCTGGGCTCCTGAGCACCAGAAGGCATTTGATGCT  3540

3541  ATCAAAAAGGCCCTGCTGAGCGCACCTGCTCTGGCCCTCCCTGACGTAACTAAACCCTTT  3600

3601  ACCCTTTATGTGGATGAGCGTAAGGGAGTAGCCCGAGGAGTTTTAACCCAAACCCTAGGA  3660

3661  CCATGGAGGAGACCTGTTGCCTACCTGTCAAAGAAGCTTGATCCTGTAGCCAGTGGTTGG  3720

3721  CCCGTATGTCTGAAGGCTATCGCAGCTGTGGCCATACTGGTCAAGGACGCTGACAAATTG  3780
```

Figure 2 cont.

```
3781  ACTTTGGGACAGAATATAACTGTAATAGCCCCCATGCATTGGAGAACATCGTTCGGCAG  3840

3841  CCCCCAGACCGATGGATGACCAACGCCCGCATGACCCACTATCAAAGCCTGCTTCTCACA  3900

3901  GAGAGGGTCACTTTCGCTCCACCAGCCGCTCTCAACCCTGCCACTCTTCTGCCTGAAGAG  3960

3961  ACTGATGAACCAGTGACTCATGATTGCCATCAACTATTGATTGAGGAGACTGGGGTCCGC  4020

4021  AAGGACCTTACAGACATACCGCTGACTGGAGAAGTGCTAACCTGGTTCACTGACGGAAGC  4080

4081  AGCTATGTGGTGGAAGGTAAGAGGATGGCTGGGGCGGCAGTGGTGGACGGGACCCGCACG  4140

4141  ATCTGGGCCAGCAGCCTGCCGGAAGGAACTTCAGCGCAAAAGGCTGAGCTCATGGCCCTC  4200

4201  ACGCAAGCTTTGCGGCTGGCCGAAGGGAAATCCATAAACATTTATACGGACAGCAGGTAT  4260

4261  GCCTTTGCGACTGCACACGTACACGGGGCCATCTATAAACAAAGGGGGTTGCTTACCTCA  4320

4321  GCAGGGAGGGAAATAAAGAACAAAGAGGAAATTCTAAGCCTATTAGAAGCCTTACATTTG  4380

4381  CCAAAAAGGCTAGCTATTATACACTGTCCTGGACATCAGAAAGCCAAAGATCTCATATCT  4440

4441  AGAGGGAACCAGATGGCTGACCGGGTTGCCAAGCAGGCAGCCCAGGCTGTTAACCTTCTG  4500

4501  CCTATAATAGAAACGCCCAAAGCCCCAGAACCCAGACGACAGTACACCCTAGAAGACTGG  4560

4561  CAAGAGATAAAAAAGATAGACCAGTTCTCTGAGACTCCGGAGGGGACCTGCTATACCTCA  4620

4621  TATGGGAAGGAAATCCTGCCCCACAAAGAAGGGTTAGAATATGTCCAACAGATACATCGT  4680

4681  CTAACCCACCTAGGAACTAAACACCTGCAGCAGTTGGTCAGAACATCCCCTTATCATGTT  4740

4741  CTGAGGCTACCAGGAGTGGCTGACTCGGTGGTCAAACATTGTGTGCCCTGCCAGCTGGTT  4800

4801  AATGCTAATCCTTCCAGAATACCTCCAGGAAAGAGACTAAGGGGAAGCCACCCAGGCGCT  4860

4861  CACTGGGAAGTGGACTTCACTGAGGTAAAGCCGGCTAAATACGGAAACAAATATCTATTG  4920

4921  GTTTTTGTAGACACCTTTTCAGGATGGGTAGAGGCTTATCCTACTAAGAAAGAGACTTCA  4980

4981  ACCGTGGTGGCTAAGAAAATACTGGAGGAAATTTTTCCAAGATTTGGAATACCTAAGGTA  5040
```

Figure 2 cont.

```
5041 ATAGGGTCAGACAATGGTCCAGCTTTCGTTGCCCAGGTAAGTCAGGGACTGGCCAAGATA 5100

5101 TTGGGGATTGATTGGAAACTGCATTGTGCATACAGACCCCAAAGCTCAGGACAGGTAGAG 5160

5161 AGGATGAATAGAACCATTAAAGAGACCCTTACCAAATTGACCACAGAGACTGGCATTAAT 5220

5221 GATTGGATGGCTCTCCTGCCCTTTGTGCTTTTAGGGTGAGGAACACCCCTGGACAGTTT 5280

5281 GGGCTGACCCCTATGAATTGCTCTACGGGGACCCCCCCGTTGGCAGAAATTGCCTTT 5340

5341 GCACATAGTGCTGATGTGCTGCTTTCCCAGCCTTTGTTCTCTAGGCTCAAGGCGCTCGAG 5400

5401 TGGGTGAGGCAGCGAGCGTGGAAGCAGCTCGGGAGGCCTACTCAGGAGGAGACTTGCAA 5460

5461 GTTCCACATCGCTTCCAAGTTGGAGATTCAGTCTATGTTAGACGCCACCGTGCAGGAAAC 5520

5521 CTCGAGACTCGGTGGAAGGGACCTTATCTCGTACTTTTGACCACACCAACGGCTGTGAAA 5580

5581 GTCGAAGGAATCCCCACCTGGATCCATGCATCCACGTTAAGCYGGCGCCACCTCCCGAC 5640

5641 TCGGGTGGAGAGCCGAAAAGACTGAGAATCCCCTTAAGCTTCGCCTCCATCGCCTGGTT 5700

5701 CCTTACTCTAACAATAACTCCCCAGGCCAGTAGTAAACGCCTTATAGACAGCTCGAACCC 5760

5761 CCATAGACCTTTATCCCTTACCTGGCTGATTATTGACCCTGATACGGGTGTCACTGTAAA 5820

5821 TAGCACTCGAGGTGTTGCTCCTAGAGGCACCTGGTGGCCTGAACTGCATTTCTGCCTCCG 5880

5881 ATTGATTAACCCCGCTGTTAARAGCACACCTCCCAACCTAGTCCGTAGTTATGGGTTCTA 5940

5941 TTGCTGCCCAGGCACAGAGAAAGAGAAATACTGTGGGGGTTCTGGGGAATCCTTCTGTAG 6000

6001 GAGATGGAGCTGCGTCACCTCCAACGATGGAGACTGGAAATGGCCGATCTCTCTCCAGGA 6060

6061 CCGGGTAAAATTCTCCTTTGTCAATTCCGGCCCGGGCAAGTACAAAATGATGAAACTATA 6120

6121 TAAAGATAAGAGCTGCTCCCCATCAGACTTAGATTATCTAAAGATAAGTTTCACTGAAAG 6180

6181 GAAAACAGGAAAATATTCAAAAGTGGATAAATGGTATGAGCTGGGGAATAGTTTTTTATT 6240

6241 ATATGGCGGGGAGCAGGGTCCACTTTAACCATTCGCCTTAGGATAGAGACGGGGACAGA 6300
```

Figure 2 cont.

```
6301  ACCCCCTGTGGCAATGGGACCCGATAAAGTACTGGCTGAACAGGGGCCCCCGGCCCTGGA  6360
6361  GCCACCGCATAACTTGCCGGTGCCCCAATTAACCTCGCTGCGGCCTGACATAACACAGCC  6420
6421  GCCTAGCAACAGTACCACTGGATTGATTCCTACCAACACGCCTAGAAACTCCCCAGGTGT  6480
6481  TCCTGTTAAGACAGGACAGAGACTCTTCAGTCTCATCCAGGGAGCTTTCCAAGCCATCAA  6540
6541  CTCCACCGACCCTGATGCCACTTCTTCTTGTTGGCTTTGTCTATCCTCAGGGCCTCCTTA  6600
6601  TTATGAGGGGATGGCTAAAGAAAGAAAATTCAATGTGACCAAAGAGCATAGAAATCAATG  6660
6661  TACATGGGGGTCCCGAAATAAGCTTACCCTCACTGAAGTTTCCGGGAAGGGGACATGCAT  6720
6721  AGGAAAAGCTCCCCCATCCCACCAACACCTTTGCTATAGTACTGTGGTTTATGAGCAGGC  6780
6781  CTCAGAAAATCAGTATTTAGTACCTGGTTATAACAGGTGGTGGGCATGCAATACTGGGTT  6840
6841  AACCCCCTGTGTTTCCACCTCAGTCTTCAACCAATCCAAAGATTTCTGTGTCATGGTCCA  6900
6901  AATCGTCCCCCGAGTGTACTACCATCCTGAGGAAGTGGTCCTTGATGAATATGACTATCG  6960
6961  GTATAACCGACCAAAAAGAGAACCCGTATCCCTTACCCTAGCTGTAATGCTCGGATTAGG  7020
7021  GACGGCCGTTGGCGTAGGAACAGGGACAGCTGCCCTGATCACAGGACCACAGCAGCTAGA  7080
7081  GAAAGGACTTGGTGAGCTACATGCGGCCATGACAGAAGATCTCCGAGCCTTAAAGGAGTC  7140
7141  TGTTAGCAACCTAGAAGAGTCCCTGACTTCTTTGTCTGAAGTGGTTCTACAGAACCGGAG  7200
7201  GGGATTAGATCTGCTGTTTCTAAGAGAAGGTGGGTTATGTGCAGCCTTAAAAGAAGAATG  7260
7261  TTGCTTCTATGTAGATCACTCAGGAGCCATCAGAGACTCCATGAACAAGCTTAGAAAAAA  7320
7321  GTTAGAGAGGCGTCGAAGGGAAAGAGAGGCTGACCAGGGGTGGTTTGAAGGATGGTTCAA  7380
7381  CAGGTCTCCTTGGATGACCACCCTGCTTTCTGCTCTGACGGGCCCCTAGTAGTCCTGCT  7440
7441  CCTGTTACTTACAGTTGGGCCTTGCTTAATTAATAGGTTTGTTGCCTTTGTTAGAGAACG  7500
7501  AGTGAGTGCAGTCCAGATCATGGTACTTAGGCAACAGTACCAAGGCCTTCTGAGCCAAGG  7560
```

Figure 2 cont.

```
7561  AGAAACTGACCTCTAGCCTTCCCAGTTCTAAGATTAGAACTATTAACAAGACAAGAAGTG  7620

7621  GGGAATGAAAGGATGAAAATGCAACCTAACCCTCCCAGAACCCAGGAAGTTAATAAAAAG  7680

7681  CTCTAAATGCCCCCGAATTMCAGACCCTGCTGGCTGCCAGTAAATAGGTAGAAGGTCACA  7740

7741  CTTCCTATTGTTCCAGGGCCTGCTATCCTGGCCTAAGTAAGATAACAGGAAATGAGTTGA  7800

7801  CTAATCGCTTATCTGGATTCTGTAAAACTGACTGGCACCATAGAAGAATTGATTACACAT  7860

7861  TGACAGCCCTAGTGACCTATCTCAACTGCAATCTGTCACTCTGCCCAGGAGCCCACGCAG  7920

7921  ATGCGGACCTCCGGAGCTATTTTAAAATGATTGGTCCACGGAGCGCGGGCTCTCGATATT  7980

7981  TTAAAATGATTGGTCCATGGAGCGCGGGCTCTCGATATTTTAAAATGATTGGTTTGTGAC  8040

8041  GCACAGGCTTTGTTGTGAACCCCATAAAAGCTGTCCCGATTCCGCACTCGGGGCCGCAGT  8100

8101  CCTCTACCCCTGCGTGGTGTACGACTGTGGGCCCAGCGCGCTTGGAATAAAAATCCTCT  8160

8161  TGCTGTTTGCATCAAAAAAAAAAAAAAAAAAAAAA  8196
```

Figure 3

```
   1  GTGGTGTACGACTGTGGGCCCCAGCGCGCTTGGAATAAAAATCCTCTTGCTGTTTGCATC    60

61  AAGACCGCTTCTCGTGAGTGATTTGGGGTGTCGCCTCTTCCGAGCCCGGACGAGGGGAT   120

121  TGTTCTTTTACTGGCCTTTCATTTGGTGCGTTGGCCGGGAAATCCTGCGACCACCCCTTA  180

181  CACCCGAGAACCGACTTGGAGGTAAAGGGATCCCCTTTGGAACGTGTGTGTGTCGCC    240

241  GGCGTCTCTGTTCTGAGTGTCTGTTTTCGGTGATGCGCGCTTTCGGTTTGCAGCTGTCCT  300

301  CTCAGACCGTAAGGACTGGAGGACTGTGATCAGCAGACGTGCTAGGAGGATCACAGGCTG  360

361  CCACCCTGGGGGACGCCCGGGAGGTGGGGAGAGCCAGGGACGCCTGGTGGTCTCCTACT   420

421  GTCGGTCAGAGGACCGAGTTCTGTTGTTGAAGCGAAAGCTTCCCCCTCCGCGGCCGTCCG  480

481  ACTCTTTTGCCTGCTTGTGGAAGACGCGGACGGGTCGCGTGTGTCTGGATCTGTTGGTTT  540

541  CTGTCTCGTGTGTCTTTGTCTTGTGCGTCCTTGTCTACAGTTTTAATATGGGACAGACAG  600
                                                    MetGlyGlnThrV

601  TGACTACCCCCTTAGTTTGACTCTCGACCATTGGACTGAAGTTAGATCCAGGGCTCATA   660
      alThrThrProLeuSerLeuThrLeuAspHisTrpThrGluValArgSerArgAlaHisA

661  ATTTGTCAGTTCAGGTTAAGAAGGGACCTTGGCAGACTTTCTGTGCCTCTGAATGGCCAA   720
      snLeuSerValGlnValLysLysGlyProTrpGlnThrPheCysAlaSerGluTrpProT

721  CATTCGATGTTGGATGGCCATCAGAGGGGACCTTTAATTCTGAAATTATCCTGGCTGTTA   780
      hrPheAspValGlyTrpProSerGluGlyThrPheAsnSerGluIleIleLeuAlaValL

781  AGGCAATCATTTTTCAGACTGGACCCGGCTCTCATCCTGATCAGGAGCCCTATATCCTTA   840
      ysAlaIleIlePheGlnThrGlyProGlySerHisProAspGlnGluProTyrIleLeuT

841  CGTGGCAAGATTTGGCAGAAGATCCTCCGCCATGGGTTAAACCATGGCTAAATAAACCAA   900
      hrTrpGlnAspLeuAlaGluAspProProProTrpValLysProTrpLeuAsnLysProA

901  GAAAGCCAGGTCCCCGAATCCTGGCTCTTGGAGAGAAAAACAAACACTCGGCCGAAAAAG   960
      rgLysProGlyProArgIleLeuAlaLeuGlyGluLysAsnLysHisSerAlaGluLysV

961  TCGAGCCCTCTTCCTCGTATCTACCCCGAGATCGAGGAGCCGCCGACTTGGCCGGAACCC  1020
      alGluProSerSerSerTyrLeuProArgAspArgGlyAlaAlaAspLeuAlaGlyThrP

1021  CAACCTGTTCCCCCACCCCCTTATCCAGCACAGGGTGCTGTGAGGGGACCTCTGCCCCTC  1080
      roThrCysSerProThrProLeuSerSerThrGlyCysCysGluGlyThrSerAlaProP
```

Figure 3 cont.

```
1081  CTGGAGCTCCGGTGGTGGAGGGACCTGCTGCCGGGACTCGGAGCCGGAGAGGCGCCACCC   1140
      roGlyAlaProValValGluGlyProAlaAlaGlyThrArgSerArgArgGlyAlaThrP

1141  CGGAGCGGACAGACGAGATCGCGATATTACCGCTGCGCACCTATGGCCCTCCCATGCCAG   1200
      roGluArgThrAspGluIleAlaIleLeuProLeuArgThrTyrGlyProProMetProG

1201  GGGGCCAATTGCAGCCCCTCCAGTATTGGCCCTTTTCTTCTGCAGATCTCTATAATTGGA   1260
      lyGlyGlnLeuGlnProLeuGlnTyrTrpProPheSerSerAlaAspLeuTyrAsnTrpL

1261  AAACTAACCATCCCCCTTTCTCGGAGGATCCCCAACGCCTCACGGGGTTGGTGGAGTCCC   1320
      ysThrAsnHisProProPheSerGluAspProGlnArgLeuThrGlyLeuValGluSerL

1321  TTATGTTCTCTCACCAGCCTACTTGGGATGATTGTCAACAGCTGCTGCAGACACTCTTCA   1380
      euMetPheSerHisGlnProThrTrpAspAspCysGlnGlnLeuLeuGlnThrLeuPheT

1381  CAACCGAGGAGCGAGAGAGAATTCTGTTAGAGGCTAGAAAAAATGTTCCTGGGGCCGACG   1440
      hrThrGluGluArgGluArgIleLeuLeuGluAlaArgLysAsnValProGlyAlaAspG

1441  GGCGACCCACGCAGTTGCAAAATGAGATTGACATGGGATTTCCCTTGACTCGCCCCGGTT   1500
      lyArgProThrGlnLeuGlnAsnGluIleAspMetGlyPheProLeuThrArgProGlyT

1501  GGGACTACAACACGGCTGAAGGTAGGGAGAGCTTGAAAATCTATCGCCAGGCTCTGGTGG   1560
      rpAspTyrAsnThrAlaGluGlyArgGluSerLeuLysIleTyrArgGlnAlaLeuValA

1561  CGGGTCTCCGGGGCGCCTCAAGACGGCCCACTAATTTGGCTAAGGTAAGAGAGGTGATGC   1620
      laGlyLeuArgGlyAlaSerArgArgProThrAsnLeuAlaLysValArgGluValMetG

1621  AGGGACCGAACGAACCTCCCTCGGTATTTCTTGAGAGGCTCATGGAAGCCTTCAGGCGGT   1680
      lnGlyProAsnGluProProSerValPheLeuGluArgLeuMetGluAlaPheArgArgP

1681  TCACCCCTTTTGATCCTACCTCAGAGGCCCAGAAAGCCTCAGTGGCCCTGGCCTTCATTG   1740
      heThrProPheAspProThrSerGluAlaGlnLysAlaSerValAlaLeuAlaPheIleG

1741  GGCAGTCGGCTCTGGATATCAGGAAGAAACTTCAGAGACTGGAAGGGTTACAGGAGGCTG   1800
      lyGlnSerAlaLeuAspIleArgLysLysLeuGlnArgLeuGluGlyLeuGlnGluAlaG

1801  AGTTACGTGATCTAGTGAGAGAGGCAGAGAAGGTGTATTACAGAAGGGAGACAGAAGAGG   1860
      luLeuArgAspLeuValArgGluAlaGluLysValTyrTyrArgArgGluThrGluGluG

1861  AGAAGGAACAGAGAAAAGAAAAGGAGAGAGAAGAAAGGGAGGAAAGACGTGATAGACGGC   1920
      luLysGluGlnArgLysGluLysGluArgGluGluArgGluGluArgArgAspArgArgG

1921  AAGAGAAGAAATTTGACTAAGATCTTGGCCGCAGTGGTTGAAGGGAAGAGCAGCAGGGAGA   1980
      lnGluLysAsnLeuThrLysIleLeuAlaAlaValValGluGlyLysSerSerArgGluA

1981  GAGAGAGAGATTTTAGGAAAATTAGGTCAGGCCCTAGACAGTCAGGGAACCTGGGCAATA   2040
      rgGluArgAspPheArgLysIleArgSerGlyProArgGlnSerGlyAsnLeuGlyAsnA
```

Figure 3 cont.

```
2041 GGACCCCACTCGACAAGGACCAGTGTGCGTATTGTAAAGAAAAAGGACACTGGGCAAGGA 2100
     rgThrProLeuAspLysAspGlnCysAlaTyrCysLysGluLysGlyHisTrpAlaArgA

2101 ACTGCCCCAAGAAGGGAAACAAAGGACCGAAGgTCCTAGCTCTAGAAGAAGATAAAGATT 2160
     snCysProLysLysGlyAsnLysGlyProLysValLeuAlaLeuGluGluAspLysAspE

2161 AGGGGAGACGGGgTTCGGACCCCCTCCCCGAGCCCAGGGTAACTTTGAAGGTGGAGGGGC 2220
     ndGlyArgArgGlySerAspProLeuProGluProArgValThrLeuLysValGluGlyG

2221 AACCAGTTGAGTTCCTGGTTGATACCGGAGCGGAGCATTCAGTGCTGCTACAACCATTAG 2280
     lnProValGluPheLeuValAspThrGlyAlaGluHisSerValLeuLeuGlnProLeuG

2281 GAAAACTAAAAGAAAAAAATCCTGGGTGATGGGTGCCACAGGGCAACGGCAGTATCCAT 2340
     lyLysLeuLysGluLysLysSerTrpValMetGlyAlaThrGlyGlnArgGlnTyrProT

2341 GGACTACCCGAAGAACCGTTGACTTGGGAGTGGGACGGGTAACCCACTCGTTTCTGGTCA 2400
     rpThrThrArgArgThrValAspLeuGlyValGlyArgValThrHisSerPheLeuValI

2401 TCCCTGAGTGCCCAGTACCCCTTCTAGGTAGAGACTTACTGACCAAGATGGGAGCTCAAA 2460
     leProGluCysProValProLeuLeuGlyArgAspLeuLeuThrLysMetGlyAlaGlnI

2461 TTTCTTTTGAACAAGGAAGACCAGAAGTGTCTGTGAATAACAAACCCATCACTGTGTTGA 2520
     leSerPheGluGlnGlyArgProGluValSerValAsnAsnLysProIleThrValLeuT

2521 CCCTCCAATTAGATGATGAATATCGACTATATTCTCCCCAAGTAAAGCCTGATCAAGATA 2580
     hrLeuGlnLeuAspAspGluTyrArgLeuTyrSerProGlnValLysProAspGlnAspI

2581 TACAGTCCTGGTTGGAGCAGTTTCCCCAAGCCTGGGCAGAAACCGCAGGGATGGGTTTGG 2640
     leGlnSerTrpLeuGluGlnPheProGlnAlaTrpAlaGluThrAlaGlyMetGlyLeuA

2641 CAAAGCAAGTTCCCCCACAGGTTATTCAACTGAAGGCCAGTGCTACACCAGTATCAGTCA 2700
     laLysGlnValProProGlnValIleGlnLeuLysAlaSerAlaThrProValSerValA

2701 GACAGTACCCCTTGAGTAGAGAGGCTCGAGAAGGAATTTGGCCGCATGTTCAAAGATTAA 2760
     rgGlnTyrProLeuSerArgGluAlaArgGluGlyIleTrpProHisValGlnArgLeuI

2761 TCCAACAGGGCATCCTAGTTCCTGTCCAATCCCCTTGGAATACTCCCCTGCTACCGGTTA 2820
     leGlnGlnGlyIleLeuValProValGlnSerProTrpAsnThrProLeuLeuProValA

2821 GGAAGCCTGGGACCAATGATTATCGACCAGTACAGGACTTGAGAGAGGTCAATAAAAGGG 2880
     rgLysProGlyThrAsnAspTyrArgProValGlnAspLeuArgGluValAsnLysArgV

2881 TGCAGGACATACACCCAACGGTCCCGAACCCTTATAACCTCTTGAGCGCCCTCCCGCCTG 2940
     alGlnAspIleHisProThrValProAsnProTyrAsnLeuLeuSerAlaLeuProProG

2941 AACGGAACTGGTACACAGTATTGGACTTAAAAGATGCCTTCTTCTGCCTGAGATTACACC 3000
     luArgAsnTrpTyrThrValLeuAspLeuLysAspAlaPhePheCysLeuArgLeuHisP
```

Figure 3 cont.

```
3001  CCACTAGCCAACCACTTTTTGCCTTCGAATGGAGAGATCCAGGTACGGGAAGAACCGGGC  3060
      roThrSerGlnProLeuPheAlaPheGluTrpArgAspProGlyThrGlyArgThrGlyG

3061  AGCTCACCTGGACCCGACTGCCCCAAGGGTTCAAGAACTCCCCGACCATCTTTGACGAAG  3120
      lnLeuThrTrpThrArgLeuProGlnGlyPheLysAsnSerProThrIlePheAspGluA

3121  CCCTACACAGGGACCTGGCCAACTTCAGGATCCAACACCCTCAGGTGACCCTCCTCCAGT  3180
      laLeuHisArgAspLeuAlaAsnPheArgIleGlnHisProGlnValThrLeuLeuGlnT

3181  ACGTGGATGACCTGCTTCTGGCGGGAGCCACCAAACAGGACTGCTTAGAAGGTACGAAGG  3240
      yrValAspAspLeuLeuLeuAlaGlyAlaThrLysGlnAspCysLeuGluGlyThrLysA

3241  CACTACTGCTGGAATTGTCTGACCTAGGCTACAGAGCCTCTGCTAAGAAGGCCCAGATTT  3300
      laLeuLeuLeuGluLeuSerAspLeuGlyTyrArgAlaSerAlaLysLysAlaGlnIleC

3301  GCAGGAGAGAGGTAACATACTTGGGGTACAGTTTGCGGGGCGGGCAGCGATGGCTGACGG  3360
      ysArgArgGluValThrTyrLeuGlyTyrSerLeuArgGlyGlyGlnArgTrpLeuThrG

3361  AGGCACGGAAGAAAACTGTAGTCCAGATACCGGCCCCAACCACAGCCAAACAAGTGAGAG  3420
      luAlaArgLysLysThrValValGlnIleProAlaProThrThrAlaLysGlnValArgG

3421  AGTTTTTGGGGACAGCTGGATTTTGCAGACTGTGGATCCCGGGTTTGCGACCTTAGCAG  3480
      luPheLeuGlyThrAlaGlyPheCysArgLeuTrpIleProGlyPheAlaThrLeuAlaA

3481  CCCCACTCTACCCGCTAACCAAAGAAAAAGGGGGATTCTCCTGGGCTCCTGAGCACCAGA  3540
      laProLeuTyrProLeuThrLysGluLysGlyGlyPheSerTrpAlaProGluHisGlnL

3541  AGGCATTTGATGCTATCAAAAAGGCCCTGCTGAGCGCACCTGCTCTGGCCCTCCCTGACG  3600
      ysAlaPheAspAlaIleLysLysAlaLeuLeuSerAlaProAlaLeuAlaLeuProAspV

3601  TAACTAAACCCTTTACCCTTTATGTGGATGAGCGTAAGGGAGTAGCCCGAGGAGTTTTAA  3660
      alThrLysProPheThrLeuTyrValAspGluArgLysGlyValAlaArgGlyValLeuT

3661  CCCAAACCCTAGGACCATGGAGGAGACCTGTTGCCTACCTGTCAAAGAAGCTTGATCCTG  3720
      hrGlnThrLeuGlyProTrpArgArgProValAlaTyrLeuSerLysLysLeuAspProV

3721  TAGCCAGTGGTTGGCCCGTATGTCTGAAGGCTATCGCAGCTGTGGCCATACTGGTCAAGG  3780
      alAlaSerGlyTrpProValCysLeuLysAlaIleAlaAlaValAlaIleLeuValLysA

3781  ACGCTGACAAATTGACTTTGGGACAGAATATAACTGTAATAGCCCCCCATGCATTGGAGA  3840
      spAlaAspLysLeuThrLeuGlyGlnAsnIleThrValIleAlaProHisAlaLeuGluH

3841  ACATCGTTCGGCAGCCCCCAGACCGATGGATGACCAACGCCCGCATGACCCACTATCAAA  3900
      isIleValArgGlnProProAspArgTrpMetThrAsnAlaArgMetThrHisTyrGlnS

3901  GCCTGCTTCTCACAGAGAGGGTCACTTTCGCTCCACCAGCCGCTCTCAACCCTGCCACTC  3960
      erLeuLeuLeuThrGluArgValThrPheAlaProProAlaAlaLeuAsnProAlaThrL
```

Figure 3 cont

```
3961  TTCTGCCTGAAGAGACTGATGAACCAGTGACTCATGATTGCCATCAACTATTGATTGAGG    4020
      euLeuProGluGluThrAspGluProValThrHisAspCysHisGlnLeuLeuIleGluG

4021  AGACTGGGGTCCGCAAGGACCTTACAGACATACCGCTGACTGGAGAAGTGCTAACCTGGT    4080
      luThrGlyValArgLysAspLeuThrAspIleProLeuThrGlyGluValLeuThrTrpP

4081  TCACTGACGGAAGCAGCTATGTGGTGGAAGGTAAGAGGATGGCTGGGGCGGCAGTGGTGG    4140
      heThrAspGlySerSerTyrValValGluGlyLysArgMetAlaGlyAlaAlaValValA

4141  ACGGGACCCGCACGATCTGGGCCAGCAGCCTGCCGGAAGGAACTTCAGCGCAAAAGGCTG    4200
      spGlyThrArgThrIleTrpAlaSerSerLeuProGluGlyThrSerAlaGlnLysAlaG

4201  AGCTCATGGCCCTCACGCAAGCTTTGCGGCTGGCCGAAGGGAAATCCATAAACATTTATA    4260
      luLeuMetAlaLeuThrGlnAlaLeuArgLeuAlaGluGlyLysSerIleAsnIleTyrT

4261  CGGACAGCAGGTATGCCTTTGCGACTGCACACGTACACGGGGCCATCTATAAACAAAGGG    4320
      hrAspSerArgTyrAlaPheAlaThrAlaHisValHisGlyAlaIleTyrLysGlnArgG

4321  GGTTGCTTACCTCAGCAGGGAGGGAAATAAAGAACAAAGAGGAAATTCTAAGCCTATTAG    4380
      lyLeuLeuThrSerAlaGlyArgGluIleLysAsnLysGluGluIleLeuSerLeuLeuG

4381  AAGCCTTACATTTGCCAAAAAGGCTAGCTATTATACACTGTCCTGGACATCAGAAAGCCA    4440
      luAlaLeuHisLeuProLysArgLeuAlaIleIleHisCysProGlyHisGlnLysAlaL

4441  AAGATCTCATATCTAGAGGGAACCAGATGGCTGACCGGGTTGCCAAGCAGGCAGCCCAGG    4500
      ysAspLeuIleSerArgGlyAsnGlnMetAlaAspArgValAlaLysGlnAlaAlaGlnA

4501  CTGTTAACCTTCTGCCTATAATAGAAACGCCCAAAGCCCCAGAACCCAGACGACAGTACA    4560
      laValAsnLeuLeuProIleIleGluThrProLysAlaProGluProArgArgGlnTyrT

4561  CCCTAGAAGACTGGCAAGAGATAAAAAAGATAGACCAGTTCTCTGAGACTCCGGAGGGGA    4620
      hrLeuGluAspTrpGlnGluIleLysLysIleAspGlnPheSerGluThrProGluGlyT

4621  CCTGCTATACCTCATATGGGAAGGAAATCCTGCCCCACAAAGAAGGGTTAGAATATGTCC    4680
      hrCysTyrThrSerTyrGlyLysGluIleLeuProHisLysGluGlyLeuGluTyrValG

4681  AACAGATACATCGTCTAACCCACCTAGGAACTAAACACCTGCAGCAGTTGGTCAGAACAT    4740
      lnGlnIleHisArgLeuThrHisLeuGlyThrLysHisLeuGlnGlnLeuValArgThrS

4741  CCCCTTATCATGTTCTGAGGCTACCAGGAGTGGCTGACTCGGTGGTCAAACATTGTGTGC    4800
      erProTyrHisValLeuArgLeuProGlyValAlaAspSerValValLysHisCysValP

4801  CCTGCCAGCTGGTTAATGCTAATCCTTCCAGAATACCTCCAGGAAAGAGACTAAGGGGAA    4860
      roCysGlnLeuValAsnAlaAsnProSerArgIleProProGlyLysArgLeuArgGlyS

4861  GCCACCCAGGCGCTCACTGGGAAGTGGACTTCACTGAGGTAAAGCCGGCTAAATACGGAA    4920
      erHisProGlyAlaHisTrpGluValAspPheThrGluValLysProAlaLysTyrGlyA
```

Figure 3 cont.

```
4921 ACAAATATCTATTGGTTTTTGTAGACACCTTTTCAGGATGGGTAGAGGCTTATCCTACTA  4980
     snLysTyrLeuLeuValPheValAspThrPheSerGlyTrpValGluAlaTyrProThrL

4981 AGAAAGAGACTTCAACCGTGGTGGCTAAGAAAATACTGGAGGAAATTTTTCCAAGATTTG  5040
     ysLysGluThrSerThrValValAlaLysLysIleLeuGluGluIlePheProArgPheG

5041 GAATACCTAAGGTAATAGGGTCAGACAATGGTCCAGCTTTCGTTGCCCAGGTAAGTCAGG  5100
     lyIleProLysValIleGlySerAspAsnGlyProAlaPheValAlaGlnValSerGlnG

5101 GACTGGCCAAGATATTGGGGATTGATTGGAAACTGCATTGTGCATACAGACCCCAAAGCT  5160
     lyLeuAlaLysIleLeuGlyIleAspTrpLysLeuHisCysAlaTyrArgProGlnSerS

5161 CAGGACAGGTAGAGAGGATGAATAGAACCATTAAAGAGACCCTTACCAAATTGACCACAG  5220
     erGlyGlnValGluArgMetAsnArgThrIleLysGluThrLeuThrLysLeuThrThrG

5221 AGACTGGCATTAATGATTGGATGGCTCTCCTGCCCTTTGTGCTTTTTAGGGTGAGGAACA  5280
     luThrGlyIleAsnAspTrpMetAlaLeuLeuProPheValLeuPheArgValArgAsnT

5281 CCCCTGGACAGTTTGGGCTGACCCCCTATGAATTGCTCTACGGGGACCCCCCCGTTGG   5340
     hrProGlyGlnPheGlyLeuThrProTyrGluLeuLeuTyrGlyGlyProProProLeuA

5341 CAGAAATTGCCTTTGCACATAGTGCTGATGTGCTGCTTTCCCAGCCTTTGTTCTCTAGGC  5400
     laGluIleAlaPheAlaHisSerAlaAspValLeuLeuSerGlnProLeuPheSerArgL

5401 TCAAGGCGCTCGAGTGGGTGAGGCAGCGAGCGTGGAAGCAGCTCCGGGAGGCCTACTCAG  5460
     euLysAlaLeuGluTrpValArgGlnArgAlaTrpLysGlnLeuArgGluAlaTyrSerG

5461 GAGGAGACTTGCAAGTTCCACATCGCTTCCAAGTTGGAGATTCAGTCTATGTTAGACGCC  5520
     lyGlyAspLeuGlnValProHisArgPheGlnValGlyAspSerValTyrValArgArgH

5521 ACCGTGCAGGAAACCTCGAGACTCGGTGGAAGGGACCTTATCTCGTACTTTTGACCACAC  5580
     isArgAlaGlyAsnLeuGluThrArgTrpLysGlyProTyrLeuValLeuLeuThrThrP

5581 CAACGGCTGTGAAAGTCGAAGGAATCCCCACCTGGATCCATGCATCCCACGTTAAGCCGG  5640
     roThrAlaValLysValGluGlyIleProThrTrpIleHisAlaSerHisValLysProA
                                                MetHisProThrLeuSerArg

5641 CGCCACCTCCCGACTCGGGGTGGAGAGCCGAAAAGACTGAGAATCCCCTTAAGCTTCGCC  5700
     laProProProAspSerGlyTrpArgAlaGluLysThrGluAsnProLeuLysLeuArgL
     ArgHisLeuProThrArgGlyGlyGluProLysArgLeuArgIleProLeuSerPheAla

5701 TCCATCGCCTGGTTCCTTACTCTAACAATAACTCCCCAGGCCAGTAGTAAACGCCTTATA  5760
     euHisArgLeuValProTyrSerAsnAsnAsnSerProGlyGlnEnd
     SerIleAlaTrpPheLeuThrLeuThrIleThrProGlnAlaSerSerLysArgLeuIle

5761 GACAGCTCGAACCCCCATAGACCTTTATCCCTTACCTGGCTGATTATTGACCCTGATACG  5820
     AspSerSerAsnProHisArgProLeuSerLeuThrTrpLeuIleIleAspProAspThr
```

Figure 3 cont.

```
5821  GGTGTCACTGTAAATAGCACTCGAGGTGTTGCTCCTAGAGGCACCTGGTGGCCTGAACTG   5880
      GlyValThrValAsnSerThrArgGlyValAlaProArgGlyThrTrpTrpProGluLeu

5881  CATTTCTGCCTCCGATTGATTAACCCCGCTGTTAAAAGCACACCTCCCAACCTAGTCCGT   5940
      HisPheCysLeuArgLeuIleAsnProAlaValLysSerThrProProAsnLeuValArg

5941  AGTTATGGGTTCTATTGCTGCCCAGGCACAGAGAAAGAGAAATACTGTGGGGGTTCTGGG   6000
      SerTyrGlyPheTyrCysCysProGlyThrGluLysGluLysTyrCysGlyGlySerGly

6001  GAATCCTTCTGTAGGAGATGGAGCTGCGTCACCTCCAACGATGGAGACTGGAAATGGCCG   6060
      GluSerPheCysArgArgTrpSerCysValThrSerAsnAspGlyAspTrpLysTrpPro

6061  ATCTCTCTCCAGGACCGGGTAAAATTCTCCTTTGTCAATTCCGGCCCGGGCAAGTACAAA   6120
      IleSerLeuGlnAspArgValLysPheSerPheValAsnSerGlyProGlyLysTyrLys

6121  ATGATGAAACTATATAAAGATAAGAGCTGCTCCCCATCAGACTTAGATTATCTAAAGATA   6180
      MetMetLysLeuTyrLysAspLysSerCysSerProSerAspLeuAspTyrLeuLysIle

6181  AGTTTCACTGAAAGGAAAACAGGAAAATATTCAAAAGTGGATAAATGGTATGAGCTGGGG   6240
      SerPheThrGluArgLysThrGlyLysTyrSerLysValAspLysTrpTyrGluLeuGly

6241  AATAGTTTTTTATTATATGGCGGGGGAGCAGGGTCCACTTTAACCATTCGCCTTAGGATA   6300
      AsnSerPheLeuLeuTyrGlyGlyGlyAlaGlySerThrLeuThrIleArgLeuArgIle

6301  GAGACGGGGACAGAACCCCCTGTGGCAATGGGACCCGATAAAGTACTGGCTGAACAGGGG   6360
      GluThrGlyThrGluProProValAlaMetGlyProAspLysValLeuAlaGluGlnGly

6361  CCCCCGGCCCTGGAGCCACCGCATAACTTGCCGGTGCCCCAATTAACCTCGCTGCGGCCT   6420
      ProProAlaLeuGluProProHisAsnLeuProValProGlnLeuThrSerLeuArgPro

6421  GACATAACACAGCCGCCTAGCAACAGTACCACTGGATTGATTCCTACCAACACGCCTAGA   6480
      AspIleThrGlnProProSerAsnSerThrThrGlyLeuIleProThrAsnThrProArg

6481  AACTCCCCAGGTGTTCCTGTTAAGACAGGACAGAGACTCTTCAGTCTCATCCAGGGAGCT   6540
      AsnSerProGlyValProValLysThrGlyGlnArgLeuPheSerLeuIleGlnGlyAla

6541  TTCCAAGCCATCAACTCCACCGACCCTGATGCCACTTCTTCTTGTTGGCTTTGTCTATCC   6600
      PheGlnAlaIleAsnSerThrAspProAspAlaThrSerSerCysTrpLeuCysLeuSer

6601  TCAGGGCCTCCTTATTATGAGGGGATGGCTAAAGAAAGAAAATTCAATGTGACCAAAGAG   6660
      SerGlyProProTyrTyrGluGlyMetAlaLysGluArgLysPheAsnValThrLysGlu

6661  CATAGAAATCAATGTACATGGGGGTCCCGAAATAAGCTTACCCTCACTGAAGTTTCCGGG   6720
      HisArgAsnGlnCysThrTrpGlySerArgAsnLysLeuThrLeuThrGluValSerGly

6721  AAGGGGACATGCATAGGAAAAGCTCCCCCATCCCACCAACACCTTTGCTATAGTACTGTG   6780
      LysGlyThrCysIleGlyLysAlaProProSerHisGlnHisLeuCysTyrSerThrVal
```

Figure 3 cont.

```
6781  GTTTATGAGCAGGCCTCAGAAAATCAGTATTTAGTACCTGGTTATAACAGGTGGTGGGCA        6840
      ValTyrGluGlnAlaSerGluAsnGlnTyrLeuValProGlyTyrAsnArgTrpTrpAla

6841  TGCAATACTGGGTTAACCCCCTGTGTTTCCACCTCAGTCTTCAACCAATCCAAAGATTTC        6900
      CysAsnThrGlyLeuThrProCysValSerThrSerValPheAsnGlnSerLysAspPhe

6901  TGTGTCATGGTCCAAATCGTCCCCCGAGTGTACTACCATCCTGAGGAAGTGGTCCTTGAT        6960
      CysValMetValGlnIleValProArgValTyrTyrHisProGluGluValValLeuAsp

6961  GAATATGACTATCGGTATAACCGACCAAAAAGAGAACCCGTATCCCTTACCCTAGCTGTA        7020
      GluTyrAspTyrArgTyrAsnArgProLysArgGluProValSerLeuThrLeuAlaVal

7021  ATGCTCGGATTAGGGACGGCCGTTGGCGTAGGAACAGGGACAGCTGCCCTGATCACAGGA        7080
      MetLeuGlyLeuGlyThrAlaValGlyValGlyThrGlyThrAlaAlaLeuIleThrGly

7081  CCACAGCAGCTAGAGAAAGGACTTGGTGAGCTACATGCGGCCATGACAGAAGATCTCCGA        7140
      ProGlnGlnLeuGluLysGlyLeuGlyGluLeuHisAlaAlaMetThrGluAspLeuArg

7141  GCCTTAAAGGAGTCTGTTAGCAACCTAGAAGAGTCCCTGACTTCTTTGTCTGAAGTGGTT        7200
      AlaLeuLysGluSerValSerAsnLeuGluGluSerLeuThrSerLeuSerGluValVal

7201  CTACAGAACCGGAGGGGATTAGATCTGCTGTTTCTAAGAGAAGGTGGGTTATGTGCAGCC        7260
      LeuGlnAsnArgArgGlyLeuAspLeuLeuPheLeuArgGluGlyGlyLeuCysAlaAla

7261  TTAAAAGAAGAATGTTGCTTCTATGTAGATCACTCAGGAGCCATCAGAGACTCCATGAAC        7320
      LeuLysGluGluCysCysPheTyrValAspHisSerGlyAlaIleArgAspSerMetAsn

7321  AAGCTTAGAAAAAAGTTAGAGAGGCGTCGAAGGGAAAGAGAGGCTGACCAGGGGTGGTTT        7380
      LysLeuArgLysLysLeuGluArgArgArgArgGluArgGluAlaAspGlnGlyTrpPhe

7381  GAAGGATGGTTCAACAGGTCTCCTTGGATGACCACCCTGCTTTCTGCTCTGACGGGGCCC        7440
      GluGlyTrpPheAsnArgSerProTrpMetThrThrLeuLeuSerAlaLeuThrGlyPro

7441  CTAGTAGTCCTGCTCCTGTTACTTACAGTTGGGCCTTGCTTAATTAATAGGTTTGTTGCC        7500
      LeuValValLeuLeuLeuLeuThrValGlyProCysLeuIleAsnArgPheValAla

7501  TTTGTTAGAGAACGAGTGAGTGCAGTCCAGATCATGGTACTTAGGCAACAGTACCAAGGC        7560
      PheValArgGluArgValSerAlaValGlnIleMetValLeuArgGlnGlnTyrGlnGly

7561  CTTCTGAGCCAAGGAGAAACTGACCTCTAGCCTTCCCAGTTCTAAGATTAGAACTATTAA        7620
      LeuLeuSerGlnGlyGluThrAspLeuEnd

7621  CAAGACAAGAAGTGGGGAATGAAAGGATGAAAATGCAACCTAACCCTCCCAGAACCCAGG        7680

7681  AAGTTAATAAAAAGCTCTAAATGCCCCCGAATTACAGACCCTGCTGGCTGCCAGTAAATA        7740
```

Figure 3 cont.

```
7741  GGTAGAAGGTCACACTTCCTATTGTTCCAGGGCCTGCTATCCTGGCCTAAGTAAGATAAC  7800

7801  AGGAAATGAGTTGACTAATCGCTTATCTGGATTCTGTAAAACTGACTGGCACCATAGAAG  7860

7861  AATTGATTACACATTGACAGCCCTAGTGACCTATCTCAACTGCAATCTGTCACTCTGCCC  7920

7921  AGGAGCCCACGCAGATGCGGACCTCCGGAGCTATTTTAAAATGATTGGTCCACGGAGCGC  7980

7981  GGGCTCTCGATATTTTAAAATGATTGGTCCATGGAGCGCGGGCTCTCGATATTTTAAAAT  8040

8041  GATTGGTTTGTGACGCACAGGCTTTGTTGTGAACCCCATAAAAGCTGTCCCGATTCCGCA  8100

8101  CTCGGGGCCGCAGTCCTCTACCCCTGCGTGGTGTACGACTGTGGGCCCCAGCGCGCTTGG  8160

8161  AATAAAAATCCTCTTGCTGTTTGCATCAAAAAAAAAAAAAAAAAAAAA  8209
```

Figure 4.

The same nucleotide sequence as represented by bases 5260 to 8210 in Figure 3 is also representative for this Figure, with the following changes:

| Position | Change |
|----------|--------|
| 5273 | G-T |
| 5341 | C-T |
| 5351 | C-T |
| 5353 | T-C |
| 5356 | C-T |
| 5426 | G-A |
| 5464 | Insertion AGA |
| 5607 | C-T |
| 5638 | C-T |
| 5792 | T-C |
| 6191 | Insertion AA |
| 6253 | T-A |
| 6255 | Insertion A |
| 6900 | C-G |

Such nucleotide changes result in the following amino acid changes in the ENV polypeptide.

| Position | Change |
|----------|--------|
| 7 | R-W |
| 192 | R-K |
| 193 | Deletion |
| 194 | Deletion |
| 197 | Y-Q |
| 198 | S-E |
| 199 | K-N |
| 200 | V-I |
| 201 | D-Q |
| 204 | Y-I |
| 205 | E-N |
| 206 | Insertions: G,M,S |
| 206 | L-W |
| 208 | N-I |
| 209 | S-V |
| 211 | L-Y |
| 212 | L-K |
| 427 | F-L |

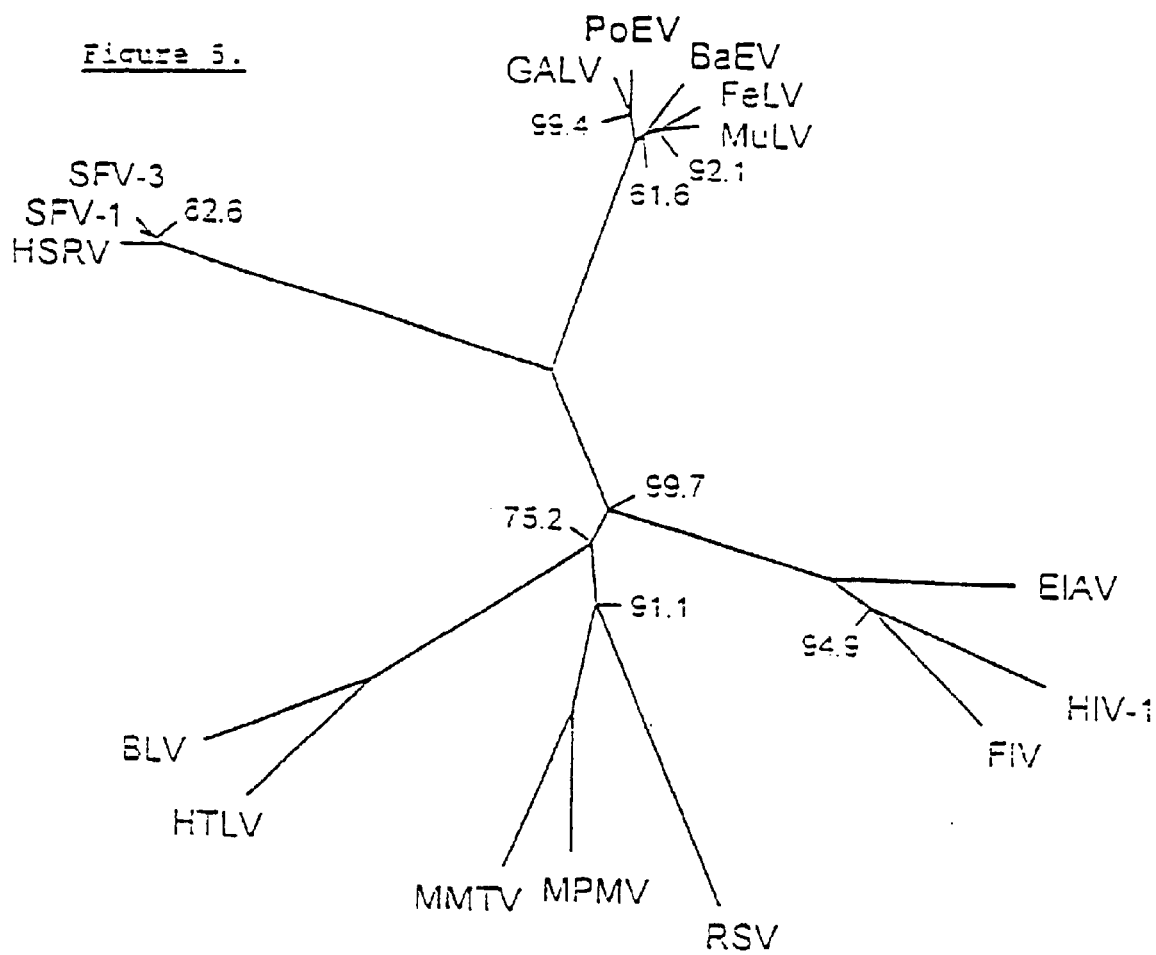

Figure 5.

| | |
|---|---|
| MuLV | murine leukaemia virus |
| FeLV | feline leukaemia virus |
| GaLV | gibbon ape leukaemia virus |
| SVV-1 | simian foamy virus 1 |
| SFV-3 | simian foamy virus 3 |
| HSRV | human foamy virus |
| BLV | Bovine leukaemia virus |
| HTLV | human T-cell leukaemia virus |
| MMTV | murine mammary tumour virus |
| MPMV | Mason Pfizer monkey virus |
| RSV | Rous sarcoma virus |
| FIV | feline immunodeficiency virus |
| HIV | human immunodeficiency virus |
| EIAV | equine infectious anaemia virus |

Figure 6

```
         PPT | U3       OCT-1          c-Myb      LyF-1    E47
  1  AAGAAGTGGGGAATGAAAGGATGAAAATGCAACCTAACCCTCCCAGAACC

ETS-1                                              AP-1
 51  CAGGAAGTTAATAAAAAGCTCTAAATGCCCCCGAATTMCAGACCCTGCTG

NF-1              AP-1/TR
101  GCTGCCAGTAAATAGGTAGAAGGTCACACTTCCTATTGTTCCAGGGCCTG

ETS-1/GATA      GATA       ETS-1  c-Myb   AP-1      GATA
151  CTATCCTGGCCTAAGTAAGATAACAGGAAATGAGTTGACTAATCGCTTAT

E47                AP-1
201  CTGGATTCTGTAAAACTGACTGGCACCATAGAAGAATTGATTACACATTG

AP-1     AP-1/GATA    c-Myb      AP-1
251  ACAGCCCTAGTGACCTATCTCAACTGCAATCTGTCACTCTGCCCAGGAGC

E47         ETS-1    →              CCAAT
301  CCACGCAGATGCGGACCTCCGGAGCTATTTTAAAATGATTGGTCCACGGA

GATA →               CCAAT ←
351  GCGCGGGCTCTCGATATTTTAAAATGATTGGTCCATGGAGCGCGGGCTCT

GATA        CCAAT ←   AP-1/CREB
401  CGATATTTTAAAATGATTGGTTTGTGACGCACAGGCTTTGTTGTGAACCC

TATA                  U3 | R
451  CATAAAAGCTGTCCCGATTCCGCACTCGGGGCCGCAGTCCTCTACCCCTG

PADS                              polyA
501  CGTGGTGTACGACTGTGGGCCCCAGCGCGCTTGGAATAAAAATCCTCTTG

R | U5
551  CTGTTTGCATCAAGACCGCTTCTYGTGAGTGATTTGGGGTGTCGCCTCTT

U5 | PBS
601  CCGAKCCCGGACGAGGGGATTGTTCTTTTACTGGCCTTTCATTTGGTGC

651  GTTGGCCGGGAAATCCTGCGACC
```

PORCINE RETROVIRUS

BACKGROUND OF THE INVENTION

The present invention relates inter alia to porcine retrovirus (PoEV) fragments, in particular polynucleotide fragments encoding at least one porcine retrovirus expression product, a recombinant vector comprising at least one polynucleotide fragment, use of PoEV polynucleotide fragments in the detection of native porcine retrovirus, a host cell containing at least one PoEV polynucleotide fragment or a recombinant vector comprising at least one PoEV polynucleotide fragment, PoEV polypeptides, antibodies immuno-reactive with PoEV polypeptides, pharmaceutical compositions comprising recombinant PoEV polypeptides for use as prophylactic and/or therapeutic agents and uses of PoEV polynucleotide fragments and/or polypeptides in medicine, including veterinary medicine and in the preparation of medicaments for use in medicine, including veterinary medicine.

Porcine retrovirus (PoEV) is an endogenous (genetically acquired) retrovirus isolated from pigs and expressed in cell lines derived from porcine material. There are no known pathogenic effects associated with the virus per se in its natural host although the virus appears to be associated with lymphomas in pigs and related viruses are associated with leukaemias and lymphomas in other species. The virus has been reported to infect cells from a variety of non-porcine origins and is, therefore, designated as a xenotropic, amphotropic or polytrophic virus (Lieber M M, Sherr C J. Benveniste R E and Todaro G J. 1975; Strandstrom H, Verjalainen P, Moening V, Hunsmann G, Schwarz H, and Schafer W. 1974; Todaro G J, Benveniste R E, Lieber M M and Sherr C J. 1974). The observation that the above viruses may have the potential to infect humans and have a pathogenic effect suggests that the issue of porcine retroviruses must be addressed in the context of xenotransplanting pig tissues or cells. Therefore, information on the properties of PoEV and the development of diagnostic reagents, molecular engineering tools and potential vaccine materials is of paramount importance for example in xenotransplantation technology and the like.

BRIEF DESCRIPTION OF THE DRAWINGS

FIG. 1 shows a nucleic acid sequence from a cDNA isolated from PoEV having the sequence of SEQ ID NO: 1.

FIG. 2 shows a nucleic acid sequence from a cDNA isolated from PoEV having the sequence of SEQ ID NO: 2.

FIG. 3 shows a nucleic acid sequence from a cDNA isolated from PoEV having the sequence of SEQ ID NO: 3. Also depicted are the amino acid sequences produced by the 3 ORFs encoded by SEQ ID NO: 3 including (i) the gag gene encoding for a polypeptide having the amino acid sequence of SEQ ID NO: 4 (corresponding to nucleotides 588–2162 of SEQ ID NO: 3); (ii) the pol gene encoding for a polypeptide having the amino sequence of SEQ ID NO: 5 (corresponding to nucleotides 2163–5747 of SEQ ID NO: 3); and (iii) the env gene encoding for a polypeptide having the amino sequence of SEQ ID NO: 6 (corresponding to nucleotides 5620–7590 of SEQ ID NO: 3).

FIG. 4 (top) shows a list of changes to the PoEV nucleic acid sequence (as compared to the sequence depicted in FIG. 3) which were found in PoEV DNA isolated from PoEV infected Raji cells. The bottom half shows a list of changes to the ENV polypeptide (as compared to the sequence depicted in FIG. 3) resulting from the nucleotide changes shown in the top half of the figure. SEQ ID NO: 9 is a nucleic acid sequence corresponding to nucleotides 5260–8210 of SEQ ID NO: 3 and containing the specified modifications. SEQ ID NO: 10 is an amino acid sequence corresponding to the ENV polypeptide of SEQ ID NO: 6 and containing the specified modifications.

FIG. 5 shows a phylogenetic tree for the POL polypeptide.

FIG. 6 the nucleotide sequence for a portion of the PoEV genome corresponding to the U3 region and depicting the multiple potential transcription sites located therein (SEQ ID NO: 17).

DETAILED DESCRIPTION OF THE INVENTION

It is an objected of the present invention to obviate and/or mitigate against at least some of the above disadvantages.

In one aspect the present invention provides an isolated PoEV polynucleotide fragment:
(a) encoding at least one porcine retrovirus (PoEV) expression product;
(b) encoding a physiologically active and/or immunogenic derivative of said expression product; or
(c) which is complementary to a polynucleotide sequence as defined in (a) or (b)

Preferably, the polynucleotide fragment encodes the gag gene (gag), polymerase gene (pol) and/or envelope (env) gene of PoEV. Thus, said expression product can be the virion core polypeptides (GAG) and polymerase (POL) and/or envelope (ENV) polypeptides of PoEV. Thus, the invention further provides a recombinant PoEV virion core, polymerase and/or envelope polypeptide.

"Polynucleotide fragment" as used herein refers to a chain of nucleotides such as deoxyribose nucleic acid (DNA) and transcription products thereof, such as RNA. Naturally, the skilled addressee will appreciate the whole naturally occurring PoEV genome is not included in the definition of polynucleotide fragment.

The polynucleotide fragment can be isolated in the sense that it is substantially free of biological material with which the whole genome is normally associated in vivo. The isolated polynucleotide fragment may be cloned to provide a recombinant molecule comprising the polynucleotide fragment. Thus, "polynucleotide fragment" includes double and single stranded DNA, RNA and polynucleotide sequences derived therefrom, for example, subsequences of said fragment and which are of any desirable length. Where a nucleic acid is single stranded then both a given strand and a sequence complementary thereto is within the scope of the present invention.

In general, the term "expression product" refers to both transcription and translation products of said polynucleotide fragments. When the expression product is a "polypetide" (i.e. a chain or sequence or amino acids displaying a biological and/or immunological activity substantially similar to the biological and/or immunological activity of PoEV virion core, polymerase and/or envelope protein), it does not refer to a specific length of the product as such. Thus, the skilled addressee will appreciate that "polypeptide" encompasses inter alia peptides, polypeptides and proteins of PoEV. The polypeptide if required, can be modified in vivo and in vitro, for example by glycosylation, amidation, carboxylation, phosphorylation and/or post-translational cleavage.

Polynucleotide fragments comprising portions encompassing the PoEV genome, and derived from retrovirus particles released from a reverse transcriptase-positive porcine kidney cell line PK-15, have been molecularly cloned into a plasmid vector. This was achieved by synthesising cDNAs of PoEV RNA genomes which were recovered from porcine kidney cells expressing the endogenous virus. The cDNA was cloned into a plasmid vector and the isolated PoEV DNA fragment determined (see FIGS. 1,2 and 3). The sequence of the sequence identified in FIG. 1 was the earliest determined sequence, followed by the sequence in FIG. 2 and lastly by the most recently revised sequence shown in FIG. 3. An additional study has been carried out to determine whether or not the human cell line "Raji" was susceptible to infection with the PoEV present in porcine kidney calls (PK15). A raji clone has now been obtained and the DNA sequence of its any gene region has been determined (see FIG. 4).

The DNA fragment of FIG. 3 was shown to encode three open reading frames (ORFs) of 524, 1194 and 656 amino acids respectively.

A comparison of the amino acid sequence against previously sequenced retroviruses from other species indicated that novel retrovirus cDNA had been cloned. Sequence analysis using the Lasergene software from DNASTAR Inc. showed that homologies were observed between the cloned PoEV DNA and the majority of retroviruses and that the closest homologies were to gibbon leukaemia virus (GaLV) in the polymerase (pol) and (env) regions of the pro-virus.

The first open reading frame ORF of FIG. 3 (nucleotides 588–2162) is predicted to encode the PoEV virion core polypeptide (gag gene). The second ORF (nucleotides 2163–5747) is predicted to encode the PoEV polymerase polypeptide (pol gene). The third ORF (nucleotides 5620–7590) is predicted to encode the PoEV envelope polypeptide (env gene). The skilled addressee will appreciate that it is possible to genetically manipulate the polynucleotide fragment or derivatives thereof, for example to clone the gene by recombinant DNA techniques generally known in the art and to express the polypeptides encoded thereby in vitro and/or in vivo. DNA fragments having the polynucleotide sequence depicted in FIGS. 1,2,3, and/or 4 or DNA/RNA derivatives thereof, may be used as a diagnostic tool or as reagent for detecting PoEV nucleic acid in nucleic acids from donor animals or as a vaccine.

Preferred fragments of this aspect of the invention are polynucleotide fragments encoding: (a) at least one of the one to three polypeptides having an amino acid sequence which is shown in FIGS. 1,2,3 and/or 4 (b) encoding a polypeptide which is a physiologically active and/or immunogenic derivative of at least one of the polypeptides defined in (a); or (c) which is complementary to a polynucleotide sequence as defined above; or polynucleotide fragments: (a) comprising at least one of the ORFs shown in FIGS. 1,2,3 and/or 4 or comprising a corresponding RNA sequence; (b) comprising a sequence having substantial nucleotide sequence identity with a sequence as described in (a) above; or (c) comprising a sequence which is complementary to a sequence as described in (a) or (b) above. It is to be understood that the term "substantial sequence identity" is taken to mean at least 50% (preferably at least 75%, at least 90%, or at least 95%) sequence identity.

The polynucleotide fragment of the present invention may be used to examine the expression and/or presence of the PoEV virus in donor animals and cells, tissues or organs derived from the donor animals to see if they are suitable for xenotransplantation (i.e. PoEV free). In addition, the recipients of pig cells, tissues or organs can be examined for the presence and/or expression of PoEV virus directly or by co-culture or infection of susceptible detector calls.

A polynucleotide fragment of the present invention may be used to identify polynucleotide sequences within the PoEV genome which are PoEV specific (i.e. is not necessary for the complete PoEV genome to be identified). Such PoEV specific polynucleotide sequences may be used to identify PoEV nucleic acid in samples, such as transplanted cells, tissues or organs and may be included in a definitive test for PoEV.

Thus, the present invention further provides an isolated PoEV polynucleotide fragment capable of specifically hybridising to a PoEV polynucleotide sequence. In this manner, the present invention provides probes and/or primers for use in ex vivo and/or in situ PoEV virus detection and expression studies. Typical detection studies include polymerase chain reaction (PCR) studies, hybridisation studies, or sequencing studies. In principle any PoEV specific polynucleotide sequence from the above identified PoEV sequence may be used in detection and/or expression studies.

"Capable of specifically hybridising" is taken to mean that said polynucleotide fragment preferably hybridises to a PoEV polynucleotide sequence in preference to polynucleotide sequences of other virus, animal (especially porcine or human sequences) and/or other species. In a preferment the PoEV fragment specifically binds to a native PoEV polynucleotide sequence or a part thereof.

The invention includes polynucleotide sequence(s) which are capable of specifically hybridising to a PoEV polynucleotide sequence or to a part thereof without necessarily being completely complementary to said PoEV polynucleotide sequence or fragment therefor. For example, there may be at least 50% preferable at least 75%, most preferably at least 90% or at least 95% complementarity. Of course, in some cases the sequences may be exactly complementary (100% complementary) or nearly so (e.g. there may be less than 10, preferably less than 5 mismatches). Thus the present invention also provides anti sense or complementary nucleotide sequence(s) which is/are capable of specifically hybridising to the disclosed DNA sequence. If a PoEV specific polynucleotide is to be used as a primer in PCR and/or sequencing studies, the polynucleotide must be capable of hybridising to PoEV nucleic acid and capable of initiating chain extension from 3' end of the polynucleotide, but not able to correctly initiate chain extension from non PoEV sequences (especially from human, or non-PoEV porcine sequences).

If a PoEV specific test polynucleotide sequence is to be used in hybridisation studies, to test for the presence of PoEV nucleic acid in a sample, the test polynucleotide should preferably remain hybridised to a sample polynucleotide under stringent conditions. If desired, either the test or sample polynucleotide may be immobilised. Generally the test polynucleotide sequence is at least 10 or at least 50 bases in length. It may be labelled by suitable techniques known in the art. Preferably the test polynucleotide sequence is at least 200 bases in length and may even be several kilobases in length. Thus, either a denatured sample or test sequence can be first bound to a support. Hybridization can be effected at a temperature of between 50 and 70° C. in double strength SSC (2×NaCl 17.5 g/l and sodium citrate (SC) at 8.8 g/l ) buffered saline containing 0.1% sodium dodecyl sulphate (SDS). This can be followed by rinsing of the support at the same temperature but with a buffer having a reduced SSC concentration. Depending upon the degree of stringency required, and thus the degree of similarity of the sequences, such reduced concentration buffers are typically single strength SSC containing 0.1% SDS, half strength SSC containing 0.1% SDS and one tenth strength SSC containing 0.1% SDS. Sequences having the greatest degree of similarity are those the hybridisation of which is least affected by washing in buffers of reduced concentration. It is most preferred that the sample and inventive sequences are so similar that the hybridisation between them is substantially unaffected by washing or incubation in one tenth strength sodium citrate buffer containing 0.1% SDS.

PoEV specific oligonucleotides may be designed to specifically hybridise to PoEV nucleic acid. They may be synthesised, by known techniques and used as primers in PCR or sequencing reactions or as probes in hybridisations designed to detect the presence of PoEV material in a sample. The oligonucleotides may be labelled by suitable labels known in the art, such as, radioactive labels, chemiluminescent labels or fluorescent labels and the like. Thus, the present invention also provides PoEV specific oligonucleotide probes and primers.

The term "oligonucleotide" is not mean to indicate any particular length of sequence and encompasses nucleotides of preferably at least 10 b (e.g. 10 b to 1 kb) in length, more preferably 12 b–500 b in length and most preferably 13 b to 100 b.

The PoEV specific oligonucleotides may be determined from the PoEV sequences shown in FIG. 1 and may be manufactured according to known techniques. They may have substantial sequence identity (e.g. at least 50%, at least 75%, at least 90% or at least 95% sequence identity) with one of the strands shown therein or an RNA equivalent, or with a part of such a strand. Preferably such a part is at least 10, at least 30, at least 50 or at least 200 bases long. It may be an ORF or a part thereof.

Oligonucleotides which are generally greater than 30 bases in length should preferably remain hybridised to a sample polynucleotide under one or more of the stringent conditions mentioned above. Oligonucleotides which are generally less than 30 bases in length should also preferably remain hybridised to a sample polynucleotide but under different conditions of high stringency. Typically the melting temperature of an oligonucleotide less than 30 bases may be calculated according to the formula of; 2° C. for every A or T, plus 4° C. for every G or C, minus 5° C. Hybridisation may take place at or around the calculated melting temperature for any particular oligonucleotide, in 6×SSC and 1% SDS. Non specifically hybridised oligonucleotides may then be removed by stringent washing, for example in 3×SSC and 0.1% SDS at the same temperature. Only substantially similar matched sequences remain hybridised i.e. said oligonucleotide and corresponding PoEV nucleic acid.

When oligonucleotides of generally less than 30 bases in length are used in sequencing and/or PCR studies, the melting temperature may be calculated in the same manner as described above. The oligonucleotide may then be allowed to anneal or hybridise at a temperature around the oligonucleotides calculated melting temperature. In the case of PCR studies the annealing temperature should be around the lower of the calculated melting temperatures for the two priming oligonucleotides. It is to be appreciated that the conditions and melting temperature calculation are provided by way of example only and are not intended to be limiting. It is possible through the experience of the experimenter to vary the contritions of hybridisation and thus anneal/hybridise oligonucleotides at temperatures above their calculated melting temperature. Indeed this can be desirable in preventing so-called non-specific hybridisation from occurring.

It is possible when conducting PCR studies to predict an expected size or sizes of PCR product(s) obtainable using an appropriate combination of two or more PoEV oligonucleotides, based on where they would hybridise to the sequence in FIG. 1. if, on conducting such a PCR on a sample of PoEV DNA, a fragment of the predicted size is obtained, then this is predictive that the DNA is PoEV.

The present invention also encompasses PoEV detection kits including at least one oligonucleotide which is PoEV specific, as well as any necessary reaction reagents, washing reagents, detection reagents, signal producing agents and the like or use in the test formats outlined above.

In a further aspect there is also provided use of a PoEV specific polynucleotide in the detection of PoEV in a sample.

In a yet further aspect there is provided use of a PoEV specific polynucleotide in a PCR for the detection of PoEV in a sample.

The skilled addressee will appreciate how polynucleotide fragments may be designed and used as primers/probes in polymerase chain reaction (PCR) experiments or Southern analysis (i.e. hybridisation studies) for detecting the presence or otherwise of PoEV polynucleotide in the nucleic acid of pigs or in cell, tissue or organ samples taken from pigs (e.g. from potential transplant organs such as liver, kidney and heart). Such cells, tissues or organs can be derived from transgenic animals produced as described in EP-A-0493852, or by other means known in the art. Thus the cells, tissues or organs of transgenic pigs can be associated with one or more homologous complement restriction factors active in humans to prevent/reduce activation of complement.

Furthermore the polynucleotide fragments of the present invention can be used to analyze the genetic organisation of endogenous PoEV located in the animal cell genome in pigs thus permitting the screening of herds of pigs for altered provirus and genomic loci (e.g. non-expressed provirus loci). Such a screening method would facilitate, for example, screening in a population of animals which are bred to lack expressed provirus and genomic loci and/or loci that do not encode infectious virus particles.

Reagents may also be developed from said polynucleotide fragments as aids to develop pigs that do not express an infectious, PoEV capable of infecting humans. Such pigs could still contain partial defective genomes that could result in the expression of non-infectious particles, viral proteins or viral mRNA. Alternatively, it may be possible to use constructs derived from the PoEV polynucleotide sequence to act as insertional mutagens to knockout the productive infectious PoEV in embryos, embryonic stem cells, or cells containing totipotential nuclei capable of forming a viable embryo. Thus qag, pol and/or env gene "knockouts" may be constructed to allow development of breeding programs in pigs whereby endogenous PoEV is substantially prevented or reduced. For example the nucleotide sequence of PoEV can be manipulated e.g. by deletion of a coding sequence in vitro and the resulting construct used to replace the natural PoEV sequence by recombination. Thus, the proviral genome can be rendered inactive in the porcine cells. The knockouts can be manipulated into embryos and/or stem cells and if required manipulated nuclei can be transferred from target cells to germ cells using micromanipulation techniques well known in the art. The invention also extends to animals derived from such germ cells.

Thus, transgenic pigs may be produced containing antisense constructs and/or ribozyme constructs capable or downregulating the expression of viral proteins, or transgenic pigs expressing a single chain immunoglobulin molecule with specificity for PoEV proteins or other protein that might interfere with protein synthesis or viral assembly may also be produced. Similar transgenes encoding transdominant negative regulators of PoEV expression or transgenes encoding competitive defective "genomic RNAs" may be used to reduce or eliminate the production of infectious virions. The generation of reagents to suppress the expression of native PoEV loci in pigs, such as, by generation of antisense nucleic acids (e.g. antisense mRNAs), ribozymes or other antiviral reagents may also be developed.

The polynucleotide fragment can be molecularly cloned into a prokaryotic or eukaryotic expression vactor using standard techniques and administered to a host. The expression vector is taken up by cells and the polynucleotide fragment of interest expressed, producing protein. Presentation of the protein on cell surface stimulates the host immune system to produce antibodies immunoreactive with said protein as part of a defence mechanism. Thus, expressed protein may be used as a vaccine.

Inactivated vaccines can be produced from PoEV's or cells releasing PoEV. Such infected cells may be generated by natural infection or by transfection of a proviral clone of PoEV. It will be understood that a proviral clone is a molecular clone encoding on a least one antigenic polypeptide of PoEV. After harvesting the virus and/or the infected cells, viruses or infected cells present can be inactivated for example, with formaldehyde, gluteraldehyde, acetylethylenimine or other suitable agent or process to generate an inactivated vaccine using methods commonly employed in the art. (CVMP Working Party on Immunological Veterinary Medicinal Products (1993). General requirements for the production and control of inactivated mammalian bacterial and viral vaccines for veterinary use). Sub unit vaccines may be prepared from the individual proteins encoded by the gag, pol and env genes. Typically a vaccine would contain env gene products either alone or in combination with gag genes produced by expression in bacteria, yeast or mammlian cell systems.

Proviral clones of PoEV can be engineered to develop single cycle or replication defective viral vectors suitable for vaccination using techniques. Such viral vectors known in the art (e.g. MuLV Murine Leukaemia Retrovirus, Adenovirus and Herpesviruses (Anderson W F. (1992). Human Gene Therapy. Science 256, 808–813) may have one or more genes essential for replication deleted, with the missing gene function expressed constitutively or conditionally from a further, different construct which is integrated into the chromosomal DNA of a complementing cell line to the proviral PoEV clone. PoEV virions released from the cell line may infect secondary target cells in the vaccine but not produce further infectious virus particles. For instance, the polynucleotide sequence encoding the reverse transcriptase domain of pol can be deleted from the proviral PoEV clone and the reverse transcriptase domain of pol integrated into the complementing cell line.

It will be understood that the polynucleotides; polypeptides; PoEV free cells, tissues and/or organs encompassed by the present invention could be used in therapy, diagnosis, and/or methods of treatment. The polynucleotides; polypeptides; PoEV free cells, tissues and/or organs encompassed by the present invention can also be used in the preparation of medicaments for use in therapy or diagnosis.

The cloning and expression of a recombinant PoEV polynucleotide fragment also facilitates in producing anti-PoEV antibodies and fragments thereof (particularly monoclonal antibodies) and evaluation of in vitro and in vivo biological activity of recombinant PoEV polymerase and/or envelope polypeptides. The antibodies may be a employed in diagnostic tests for native PoEV virus.

It will be understood that for the particular PoEV polypeptides embraced herein, natural variations can exist between individuals or between members of the family Suidae (i.e. the pig family ). These variations may be demonstrated by (an) amino acid difference(s) in the overall sequence or by deletions, substitutions, insertions, inversions or additions of (an) amino acid(s) in said sequence. All such derivations showing active polymerase and/or envelope polypeptide physiological and/or immunological activity are included within the scope of the invention. For example, for the purpose of thee present invention conservative replacements may be made between amino acids within the following groups:

(I) Alanine, serine, threonine;
(II) Glutamic acid and aspartic acid;
(III) Arginine and leucine;
(IV) Asparagine and qlutamine;
(V) Isoleucine, leucine and valine;
(VI) Phenylalanine, tyrosine and tryptophan Moreover, recombinant DNA technology may be used to prepare nucleic acid sequences encoding the various derivatives outlined above.

As is well known in the art, the degeneracy of the genetic code permits substitution of bases in a codon resulting in a different codon which is still capable of coding for the same amino acid, e.g. the codon for amino acid glutamic acid is both GAT and GAA. Consequently, it is clear that for the expression of polypeptides with the amino acid sequences shown in FIG. 1 or fragments thereof, use can be made of a derivative nucleic acid sequence with such an alternative codon composition different from the nucleic acid sequence shown in said FIG. 1.

Furthermore, fragments derived from the PoEV core, polymerase and/or envelope polypeptides as depicted in FIG. 3, which still display PoEV virus core polypeptide, polymerase and/or envelope polypeptide properties, or fragments derived from the nucleic acid sequence encoding the virus core polypeptides, polymerase and/or envelope polypeptides or derived from the nucleotide sequence depicted in FIGS. 1,2,3 and/or 4 encodinq fragments of said virus core polypeptide, polymerase and/or envelope polypeptides are also included of the present invention. Naturally, the skilled addressee will appreciate within the ambit that the said fragments should substantially retain the physiological and/or immunological properties of the GAG, POL and/or ENV polypeptides.

The PoEV polynucleotide fragment of the present invention is preferably linked to requlatory control sequences. Such control sequences may comprise promoters, operators, inducers, enhancers, ribosome binding sites, terminators etc. Suitable control sequences for a given host may be selected by those of ordinary skill in the art.

A polynucleotide fragment according to the present invention can be ligated to various expression controlling sequences, resulting in a so called recombinant nucleic acid molecule. Thus, the present invention also includes an expression vector containing an expressible PoEV nucleic acid molecule. The recombinant PoEV nucleic acid molecule can then be used for the transformation of a suitable host. Such hybrid molecules are preferably derived from, for example, plasmids or from nucleic acid sequences present in bacteriophages or viruses and are termed vector molecules.

Specific vectors which can be used to clone nucleic acid sequences according to the invention are known in the art (e.g. Rodriguez, R. L. and Denhadt, D. T., edit., Vectors: a survey of molecular cloning vectors and their uses, Butterworths, 1983).

The methods to be used for the construction of a recombinant nucleic acid molecule according to the invention are known to those of ordinary skill in the art and are inter alia set forth in Sambrook, et al. (Molecular Cloning: a laboratory manual Cold Spring Harbour Laboratory, 1989).

The present invention also relates to a transformed cell containing the PoEV polynucleotide fragment in an expressible form. "Transformation", as used herein, refers to the introduction of a heterologous polynucleotide fragment into a host cell. The method used may be any known in the art, for example, direct uptake, transfection transduction or electro poration (current Protocols in Molecular Biology, 1995. John Wiley and Sons Inc). The heterologous polynucleotide fragment may be maintained through autonomous replication or alternatively, may be integrated into the host genome. The recombinant nucleic acid molecules preferably are provided with appropriate control sequences compatible with the designated host which can regulate the expression of the inserted polynucleotide fragment, e.g. tetracycline responsive promoter thymidine kinasa promoter, SV-40 promoter and the like.

Suitable hosts for the expression of recombinant nucleic acid molecules may be prokaryotic or eukaryotic in origin. Hosts suitable for the expression of recombinant nucleic acid molecules may be selected from bacteria, yeast, insect cells and mammalian cells.

Since the biological half life and the degree of glycosylation of recombinant PoEV virus core polypeptide, polymerase and/or envelope polypeptides may be important for use in vivo, yeast and baculovirus systems, in which a greater degree of processing and glycosylation occur, are preferred. The yeast strain *Pichia Pastoris* exhibits potential for high level expression of recombinant proteins (Clare et al., 1991). The baculovirus system has been used successfully in the production of type 1 interferons (Smith at al., 1933).

Embodiments of aspects of the present invention will now be described by way of example only which are not intended to be limiting thereof.

EXAMPLES SECTION

Example 1
Preparation of Viral RNA 500 ml of supernatant derived from exponentially growing porcine kidney cells (PK-15, American Type Culture Collecticn CCL 33) was clarified by centrifugation of approximately 11, 000×g for 10 minutes. Virus was pelleted from the clarified supernatant by centrifugation at approximately 100,000×g or 60 minutes. The supernatant was discarded and the viral pellet retained for the preparation of viral RNA genomes. RNA was prepared from the virus pellet using a Dynabeads (registered trade mark) mRNA Direct kit according to the manufacturer's protocols; A PoEV virus pellet was resuspended in 500 µl of TNE (10 mM Tris HCl pH8.0, 0.1M NaCl, 1 mM EDTA) and the virions disrupted by the addition of 2 ml of lysis/binding buffer Dynabeads Oligo(dT)$_{25}$ were conditioned according to the manufacturer's instructions and added to the virus disrupted solution. Viral RNA was allowed to bind to the Dynabead for 10 minutes before the supernatant was removed and the bound RNA was washed three times with washing buffer with LiDS (0.5 ml) and twice with washing buffer alone. The RNA was finally resuspended in 25 µl of elution solution. All procedures were performed at ambient temperature RNase contamination was avoided by the wearing of gloves, observation of sterile technique and treatment of solutions and non-disposable glass and plasticware with diethyl pyrocarbonate (DEPC). The RNA was resuspended in DEPC-treated sterile water.

Example 2
Synthesis of cDNA cDNA was synthesised from the purified genomic RNA using Great Lengths™ cDNA amplification reverse transcriptase reagents (Clontech Laboratories Inc.) following the manufacturer's instructions. The RNA was primed with both oligo(dT) and random hexamers to maximise synthesis.

The Great Lengths cDNA synthesis protocol is based on a modified Gubler and Hoffman (1983) protocol for generating complementary DNA libraries and essentially consists or first-strand synthesis, second strand synthesis, adaptor ligation, and size fractionaction.

First strand synthesis: lock-docking primers anneal to the begining of the poly-A tail of the RNA due to the presence of A, C of a residue at the 3'-end of the primer. This increases the efficiency of cDNA synthesis or eliminating unnecessary reverse transcription of long stretches of poly-A. In addition, the reverse transcriptase used is MMLV (RNase H') which gives consistently better yields than do wild-type MMLV or AMV reverse transcriptase.

Second strand synthesis: the ratio of DNA polymerase I for RNase H has been optimised to increase the efficiency of the second strand synthesis and to minimize priming by hair pin loop formation. Following second-strand synthesis, the ds cDNA is treated with T4 DNA polymerase to create blunt ends.

Adaptor ligation: the cDNA is ligated to a specially designed adaptor that has a pre-existing EcoRI "sticky end". The use of this adaptor, instead of a linker, eliminates the need to methylate and the EcoRI—digest the cDNA, and thus leaves internal EcoRI, sites intact. The adaptor is 5'-phosphorylated at the blunt end to allow efficient ligation to the blunt-ended cDNA.

Size fractionation: the ds cDNA is phosphorylated at the EcoRI sites and size-fractionated to remove unligated adaptors and unincorporated nucleotides. The resulting cDNA is ready for cloning into a suitable EcoRI-digested vector.

Example 3
Molecular Cloning of cDNA

The size fractionated fragment was ligated with EcoRI-digested pZErO™ -1 plasmid vector. DNA (Invitrogen Corporation, San Diego, U.S.). The ligation mix was used to transform competent TOP10F'cells and these were plated onto L-Agar containing zeocin following the manufacturer's instructions (Zero Background™ cloning kit—Invitroqen). Several of the resulting zeocin resistant colonies were amplified in L-Broth containing zeocin and the plasmid DNA was purified by alkaline lysis (Maniatis et al., 1982).

The plasmid DNA was digested to completion with the endonuclease EcoRI and the resulting DNA fragments were separated by electrophoresis through an 1.0% agarose gel (Maniatis et al., 1982), in order to check that a fragment in the predicted size fractionated size range had been cloned. A clone identified as pPoEV was used in further experimentation.

Example 4
DNA Sequence Analysis.

pPoEV plasmid DNA was purified according to common techniques (Sambrook et al, 1989) and sequenced using an ABI automated sequencer. Overlapping sequencing primers from both strands of the molecular clone were used to determine the nucleotide sequence.

The first sequence obtained is shown in FIG. 1. This sequence was identified as encoding two ORFs of 924

(nucleotides 23–2793) and 218 (nucleotides 2642–3297) amino acids, relating to the pol and env genes respectevely. This sequence was revised and updated to the second sequence as shown in FIG. 2. This second sequence was identified as encoding three ORFs of 516 (nucleotides 576–2126), 1186 (nucleotides 2143–5733) and 656 (nucleotides 5606–7576) amino acids, encoding the PoEV gag, pol and env genes respectively. This second sequence has since been revised and updated to the sequence shown in FIG. 3. This third sequence was identified as encoding three ORFs of 524 (nucleotides 588–2162), 1194 (nucleotides 2153–5747) and 656 (nucleotides 5620–7590) amino acids, encoding the PoEV gag, pol and env genes respectively.

The differences in the disclosed sequences is reflected by improvements in carrying out and analysing the sequence obtained. However, there is 100% identity at the nucleic acid level, between positions 21–2681 so the first sequence and positions 2972–5653 of the third sequence. Overall there is a 70.5% identity in the entire 3310 bp of the first sequence with a corresponding portion of the third sequence.

There are only 3 base changes between the second sequence and the third sequence. These are as follows:

| base no. (from FIG. 2) | change |
|---|---|
| 2121 | insertion of a "G" |
| 2157 | insertion of a "G" |
| 5902 | "R" to an "A" |
| 7700 | "M" to an "A" |

The changes at base nos. 5902 and 7700 do not effect the corresponding amino acid sequence. However, the changes at positions 2121 and 2157 alter the amino acid sequence at the end of GAG and the beginning of POL. For GAG the final amino acid "S" have now been replaced by "VLA-LEEDKD" (SEQ ID NO: 15). The total product size is now 524 amino acids. For POL, the first five amino acids "RLGET" (SEQ ID NO: 16) have been deleted and replaced by "GRR". The total product size is now 1194 amino acids.

Similarities were observed between pPoEV and the majority of retroviruses determined by using alogrithims from DNASTAR Inc. Lasergene software (DNASTAR). The similarities were closest with gibbon ape leukaemia virus (GaLV) in the polymerase (pol) regions of the pro-virus at 68.5%, in the virus core (gaq) region, 59.2% and in the envelope (env) region, 39.3% The nucleotide sequence and major ORFs of the pPoEV insert are shown in FIG. 3. The largest ORF (nucleotides 2163–5747) encodes the polymerase polypeptide and the smaller ORFs (nucleotides 588–2162 and 5620–7590) encode the core and envelope polypeptides respectively.

Example 5
Purification of Cellular DNA from Cultured Cells, Tissues and Blood.

Cultured Cells

Cells were maintained in culture and approximately 5×10⁷ cells were harvested for DNA preparation. The cells were pelleted by centrifugation resuspended in phosphate-buffered saline, re-centrifuged at 1000 g for 2 minutes and the supernatant was discarded.

Porcine Tissues

Porcine tissue samples were frozen in liquid nitrogen and powdered by grinding in a mortar or between metal foil. The samples were resuspended in 5 ml of extraction buffer consisting of 0.025M EDTA (pH 8.0), 0.01 MTris.Cl pH 8.0, 0.5% SdS 20 μg/ml RNAse and 100 μg/ml proteinase K (Maniatis at., 1982).

Porcine Blood

A buffy coat was prepared from the blood samples, 20 ml samples were centrifuged at 1000 g for 15 minute. The buffy coat was resuspended in buffer and the samples centrifuged at 1000 g for 15 minutes. The process was repeated one further time. The sample was mixed with 5 ml (3× volume) of extraction buffer (Maniatis et al., 1982).

Purification

The samples (i.e. cultured cells, porcine tissue or porcine blood cells) in proteinase K-extraction buffer containing 20 g/ml RNAse and 100 μg/ml proteinase K were digested for approximately 24 hours at 37° C. The deproteinised DNA was extracted twice with phenol and twice with phenol chloroform and finally precipitated by ethanol in the presence of ammonium acetate. The DNA was recovered by centrifugation at 3000 g for 30 minutes and the supernatant discarded (Maniatis et al., 1982). The pellet was washed in 70% ethanol and allowed to air dry for approximately 1 hour. The DNA was allowed to re-dissolve in Tris EDTA (TE) buffer and the purity and concentration of the DNA was assessed by spectrophotometry (Maniatis et al., 1982).

Example 6
Southern Blot Analysis of Porcine Tissue and Cells

In order to demonstrate that the molecularly cloned DNA comprising the insert from PoEV was derived from the PK-15 cell line (American Type Culture Collection CCL33), the DNA was hybridised against cellular DNAs and its ability to detect proviral DNA was examined.

DNA purified from pPoEV was radioactively labelled and used to probe a Southern blot of endonuclease digested DNAs derived from PK-15 cells The DNAs probed were as follows:
a) Copy number controls of pPoEV DNA linearized by digestion with EcoRI. One copy per haploid cell genome was estimated to be 6.84 pg. The control was present at an estimated copy number of 1, 5 and 10 copies.
b) pK-15 DNA.
c) Negative control HeLa (American Type Culture Collection CCL2) DNA derived from a human adenocarcinoma cell line harbouring human papillomavirus type 18 DNA.
d) Negative control SP20 (European Collection of Animal Cell Cultures 85072401) DNA derived from a murine myeloma cell line harbouring a xenotropic MuLV retrovirus.

A hybridisation signal was observed in only the PK-15 porcine DNA. No signal was detected in either the negative human or murine DNAs. The PK-15 DNA contained more than 10 copies per cell with an estimated copy number of 20. The sizes of the three major EcoRI—endonuclease digested DNA fragments were approximately 3.8 kb, 1.8 kb and 0.6 kb. The sizes of relevant fragments detected in the recombinant pPoEV were comparable.

There are, as expected, a number of fragments common to the genomic DNA of PK-15 and pPoEV DNA and there is agreement between the patterns observed in both DNAs digested with XhoI, BamHI and HindIII. However, there are additional fragments obtained on digestion of pPoEV DNA by a number of endonucleases.

pPoEV sequences were also detected in swine testes (American Type Culture Collection CRL 1746) and primary porcine kidney cells (Central Veterinary Laboratory batch C04495) but not in hamster CHOK1 (American Type Culture Collection CCL61) or murine NSO myeloma cells (European Collection of Animal Cell Cultures 85110503).

In order to demonstrate that the molecularly cloned DNA comprising the insert from pPoEV could detect sequences in porcine cells and tissues in addition to PK-15 the pPoEV DNA was hybridised against cellular DNA from tissues derived from pigs and its ability to detect proviral DNA was examined (Maniatis et al., 1982).

The DNA purified from pPoEV was radioactively labelled and used to probe a Southern blot of endonuclease digested DNAs derived from pig organs including liver, kidney, heart and blood.

The DNAs probed were as follows:
a) Copy number controls of pPoEV DNA linearized by digestion with EcoRI. One copy per haploid cell genome was estimated to be 6.34 g. The control was present at an estimated copy number of 5,10, 20 and 50 copies.
b) DNA purified from the porcine tissues digested with EcoRI.

A hybridisation signal was observed in all the porcine DNAs.

The DNAs contained less than 5 copies per cell. There were approximately eight distinct bands in each DNA. The sizes of the three major endonuclease digested DNA fragments were approximately 3.8 kb, 1.8 kb and 0.6 kb.

Example 7
Polymerase Chain Reaction (PCR) Amplifications

Oligonucleotides were selected from the PoEV genome.

The upstream primer was 5'-GGA AGT GGA CTT CAC TGA G-3' (SEQ ID NO: 7).

The downstream primer was 5'-CTT TCC ACC CCG AAT CGG-3' (SEQ ID NO: 8).

The PCR was performed as described by Saiki et al (1987). One 1 µl of 100 ng/µl template DNA was added to a 49 µl reaction mixture containing 200 µM of dATP, dCTP, dGTP, dTTP, 30 pmol of both primers from the pair described above, 1 unit of DNA polymerase and 5 µl of reaction buffer. The reaction buffer contained 200 mM Tris-HCl pH 8.4, 500 mM potassium chloride and 15 mM magnesium chloride, ultrapure water. The solution was overlaid with two drops of mineral oil to prevent evaporation. Thirty five cycles of amplification were performed using a Perkin Elmer Cetus thermal cycler. Each cycle consisted of 1 minute, at 95° C. to denature the DNA, 1 minute, at 53° C. to anneal the primers to the template and 1 minute at 72° C. for primer extension. After the last cycle a further incubation for 10 minutes, at 72° C. was performed to allow extension or any partially completed product. On completion of the amplification, 10µl of the reaction mixture was electrophoresed through a 5 per cent acrylamide gel. The DNA was visualised by staining with ethidium bromide and exposure to ultraviolet light (320 nm).

The PCR reaction amplified a sequence of approximately 787 bp from pPoEV and from porcine cells as expected indicating that the assay detected the PoEV proviral DNA. There was no specific amplification of the expected sequence in cells of non-porcine origin and therefore, the PCR reaction and recombinant clone can be used as a specific and sensitive diagnostic tool for detection of PoEV.

Two further oligonucleotides were designed against the 3' end of the pol gene and 5' end of the gag gene respectively.

The 3' pol oligonucleotide was 5'-GAT GGC TCT CCT GCC CTT TG-3' (SEQ ID NO: 11).

The 5' gag oligonucleotide was 5'-CGA TGG AGG CGA AGC TTA AGG-3' (SEQ ID NO: 12).

The above oligonucleotide were also used in PCR reactions according to the conditions described above, with the exceptions that the annealing temperature was 58° and 30 cycles of replication were carried out The PCR reaction amplified a sequence of approximately 468 bp from pPoEV and from porine cells.

Example 8
Production of PoEV Polypeptide in *Escherichia coli*.

The open reading frame (ORF) encoding the pol peptide was isolated from the pPoEV clone and molecularly cloned into the plasmid pGEX-4T-1 (Pharmacia Ltd.) for expression.

Two ml cultures of *E. coli* transformed with various expression constructs were grown with shaking at 37° C. to late log phase (O.D.$_{600nm}$ of 0.6) and induced by the addition of IPTG to 0.1 mM. Induced cultures were then incubated for a further 2 hours after which the bacteria were collected by centrifugation. The bacterial pellet was lysed by boiling in SDS-PAGE sample buffer and the protein profile of the induced bacteria was analysed on a 12% acrylamide gel (Laemmli, 1970) followed by staining with coomassie brilliant blue dye.

Example 9
Isolation and Partial Sequencing of Raji Clone

The aim of the study was to determine whether the human cell line "Raji" was susceptible to infection with the PoEV present in porcine kidney cells (PK15). In order to test the capacity of the virus for xenotropism, PK15 cells were co-cultured with the B lymphoblastoid (Raji) cell line over 20 passages.

The culture system utilised direct culture and transwells, which separated the human and porcine cells, but permitted viruses to pass through the separating membrane. After every fifth passage, supernatants from the human cell lines are tested for the presence of retrovirus by reverse transcriptase assay.

Cell Cultures

Porcine kidney (PK15) cells (ATCC CCL 33) were used as the source of PoEV. The human cells used for co-cultivation with PK15 cells were the lymphoblast-like Burkitts lymphoma Raji (ATCC CCL 86) cell line. This cell line does not harbour endogenous retroviruses and lacks reverse transcriptase activity when tested by the present inventors.

Co-cultivation

Raji cells were co-cultivated directly with PK15 cells in duplicate 80 cm² flasks and exposed to the PK15 cells throughout the 20 passage culture period. The cells were passaged twice per week and PK15 cells added as necessary from a stock culture. At every fifth passage a sample of Raji cells was removed from the co-culture, washed and cultured for 3–4 days. Supernatant was then harvested and tested for presence of retrovirus by reverse transcriptase (RT) assay.

Results

The presence of reverse transcriptase activity with a preference for the $Mn^{2-}$ cation in the supernatant from detector cell cultures is suggestive of infection by porcine retrovirus. Reverse transcriptase activity with preference for the $Mn^{2-}$ template was not detected in the duplicate co-cultivated test cultures at passage 5 but was detected at passages 10, 15 and 20. No significant RT activity was detected in the negative control cultures. RT activity with preference for the $Mn^{2-}$ template was detected in positive control cultures at passage 5 and 20. An infected raji culture was diluted to single cells, and then a selection of cells cultured separately such that each culture originated from one cell. Each culture was tested by reverse-transcriptase assay. Genomic DNA was made from an RT-positive clone as described in example 5-purification. The PoEV ENV region was amplified by PCR as described below and the product molecularly cloned into pMOS blue T-vector (Amersham) This molecular clone was then sequenced (FIG. 4).

PCR

Oligonucleotides were selected from the PoEV genome.

The upstream primer was 5'-GAT GGC TCT CCT GCC CTT TG-3' (SEQ ID NO: 13) 5' base position: 5240.

The downstream primer was 5'-CCA CAG TCG TAC ACC ACG-3' (SEQ ID NO: 14) 5' base position: 8144.

Expected product size: 2904 bp.

Approx. 1 µg of genomic raji clone DNA was added to a 50 µl reaction mixture containing 200 µM of dATP, dCTP, dGTP, dTTP, 30 pM each primer detailed above, 1 u Taq DNA polymerase and 5 µl reaction buffer. The reaction buffer contained 200 mM Tris.Cl pH 8.4, 500 mM potassium chloride, 15 mM magnesium chloride and ultrapure water. The solution was overlaid with two drops of mineral oil to prevent evaporation. Thirty cycles of amplification was performed followed by an elongated extension reaction of 60 min. at 72° C.

The cycles consisted of:

95° C. 1 min

56° C. 1 min.

72° C. 2 min.

The PCR product was visualised as described in example 7. Product size: ~3 Kb.

Cloning

The PCR product was molecularly cloned into pMOS-Blue T-vector as directed by the manufacturer (pMOS-Blue T-vector kit—Amersham).

20 transformed colonies (clones) were picked and added to 5 mls L-broth containing 50 µg/ml ampicillin. The cultures were grown shaking at 37° C. overnight. Plasmid DNA was isolated from each clone using the perfect prep plesmid isolation kit as directed by the manufacturer (5 Prime—3 Prime Inc. Boulder, Co., USA).

Plasmid DNA was digested to completion with the endonucleases EcoRI and HindIII and the products visualised on an ethidium bromide-stained 1% agarose gel. A clone (raji env clone) showing the same banding pattern as that predicted for 'pK15 cell line derived PoEV', was selected for sequencing.

Sequencing

Raji env clone plasmid DNA prepared above was sequenced using an ABI automated sequencer, and the commercially available T7 sequencing primer.

The entire env gene region of the "Raji" was sequenced (see FIG. 4) and discovered to have substantial sequence identity at both the nucleic acid and amino acid levels (98.9% and 96.3% respectively) with the PoEV sequence from PK-15.

Example 10

Phylogenetic Analysis

Phylogenetic analysis was performed using the PHYLIP package. Sequence distances were calculated using the PROTDIST program (Dayhoff matrix) and a neighbour-joining unrooted phylogenetic tree reconstructed using the NEIGHBOUR program.

Bootstrapping was performed using 200 replicates of the pol alignment, created using the SEQBOOT program and a consensus tree was obtained using the CONSENSE program (see FIG. 5). The bootstrap percentages are indicated at the branch fork, with missing values equal to 100%. The data indicate that PoEV is closely related to but distinct from the type-C oncovirus typified by gibbon, murine and feline leukaemia viruses.

A phylogenetic tree was constructed from the pol alignment using the maximum likelihood algorithm (Dayhoff matrix). This tree differed from the pol NJ tree only in the placement of the BaEV lineage in relation to other mammalian type C viruses and corresponded to a low bootstrap for the BaEV fork observed in the NJ tree.

Example 11

Analysis of the LTR and Adjacent Region

The long terminal repeat (LTR) is a reiterated sequence at each end of the provirus that contains the enchancer and promoter governing transcription of the provirus as well as sequences required for reverse transcription of the RNA genome and integration of the proviral DNA. Three recognised domains of the LTR are identifiable, U3, R and U5 with the LTR being delineated by inverse repeats AAT-GAAAGG and CCTTTCATT a the 5' and 3' ends of U3 and U5 respectively.

| LTR Domain | PoEV Genome Sequence in accordance with FIG. 3 | Length bp |
|---|---|---|
| U3 | 7638–8106 | 469 |
| R* | 8107–8188, 1–61 | 82 |
| U5 | 62–143 | 82 |

*The position of the R is defined here by similarity to the 3' end of the MuLV LTR and is compatible with the observed location of a cap site approximately 24 bp downstream of the TATA box.

The U3 region contains multiple potential transcription sites as shown in FIG. 6. Most of the U3 region shows little or no homology to other mammalian type-C retroviruses which show conserved sites or repeat elements. However, there is homology to other mammalian type-C viruses towards the 3'end of the U3 & region and into R and U5. Amongst the potential transcription factor sites are those for the following:

LyF-1 is a transcriptional regulator that interacts with a novel class of promoters for lymphocyte-specific-genes (Lo et al 1991).

E47 is the prototype member of a new family of tissue specific enhancer proteins that have been shown to bind to the enhancer of murine leukaemia virus.

ETS-1 is a transcription factor primarily expressed in the haematopoiatic lineage.

The LTR contains direct repeats at 80006–8062 and 8045–8101 which together contain three potential CCAATT boxes. A potential TATA box is located at position 8129–8144.

The R region contains a PADS (Poly A downstream element) and consensus polyadenylation signal (AATAAA).

The primer binding site (PBS) of PoEV is glycine(2) tRNA which has not reported for any exogenous retrovirus.

References

Clare J J, Rayment F B, Ballantine S P, Sreekrishna K and Romanos M A. (1991). High Level expression of tetanus toxin fragment C in *Pichis pastoris* strains containing multiple tandem integrations of the gene. *Bioltechnolgy*, 9, 455–460

Derynck R, Singh A and Goeddel D V. (1983). Expression of the human interfron-γ in yeast. *Nucleic Acids Res.*, 11, 1319–1837.

DNASTAR. (1994). Lasergene Biocomputing Software for Windows, User's Guide.

Invitrogen. Version A, Zero Background™ Cloning Kit Catalog no K(2500-01.

Laemmli UK. (1970). Cleavage of structural proteins during the assembly of the head of bacteriophage T4N. *Nature*, 227, 680–685.

Liaber M M, Sherr C J. Benveniste R E and Torado G J. (1975). Biologic and immunologic properties of porcine type C viruses. *Virology* 66, 616–619.

Lo K, LAndau N R, Smale S T. *Mol. Cell. Biol.* 11:5229–5243 (1991)

Maniatis T, Fritsch E F and Sambrook J. (1982) *Molecular Cloning: A Laboratory Manual*, Cold spring Harbour Laboratory, Cold Spring Harbour, N.Y.

Saiki R K, Galfand D H, Stoffel S, Scharf S J, Higuchi R, Horn G T Mullis K B and Erlich H A. (1987). Prime-directed enzymatic amplificaation of DNA with a thermostable DNA polymerase. *Science* 239, 437–491.

Sambrook J Fritsch E F, and Maniatis T. (1989). *Molecular Cloning a Laboratory Manual*, 2nd ed. Cold Spring Harbour Laboratory, Cold Spring Harbour N.Y.

Smith G E, Summers M D and Fraser M J. (1983). Production of human beta interferon in insect cells infected with a baculovirus vector. *Mol. Cell. Biol.*, 3, 2156–2165.

Stranstrom H, Verjalainen P, Meoning V Hunsmann G, Schwarz H. and Schafer W. (1974). C-type particles produced by a permanent cell line from a leukemic pig. 1 Origin and properties of host cells and some evidence for the occurence of C-Type like particles *Virology* 57, 175–178.

Todaro G J, Benveniste R E, Lieber M M and Sherr C J. (1974). Characterizaation of a type C virus released from the porcine cell line PK (15). *Virology* 58; 65–74.

---

What is claimed is:

1. An isolated polynucleotide fragment comprising:
   (a) a nucleotide sequence having nucleotides 5620 to 7590 of SEQ ID NO: 3;
   (b) a nucleotide sequence which has at least 95% sequence identity over its entire length to the sequence set forth in (a); or
   (c) a nucleotide sequence which is complementary to a nucleotide sequence set forth in (a) or (b);
   and wherein (a), (b) or (c) encodes an ENV polypeptide.

2. An isolated polynucleotide fragment encoding for a polypeptide comprising the amino acid sequence set forth in SEQ ID NO: 6 or 10.

3. An isolated polynucleotide fragment comprising a nucleotide sequence having nucleotides 5620 to 7590 of SEQ ID NO: 3, or a nucleotide sequence which is complementary thereto.

4. A recombinant nucleic acid molecule comprising a polynucleotide fragment according to claim 1.

5. A recombinant nucleic acid molecule according to claim 4 wherein the recombinant nucleic acid molecule comprises regulatory control sequences operably linked to said polynucleotide fragment for controlling expression of said polynucleotide fragment.

6. A vector comprising a polynucleotide fragment according to claim 1.

7. A vector according to claim 6, which is a virus or a plasmid.

8. An isolated prokaryotio or eukaryotic host cell comprising a polynucleotide fragment according to claim 1.

* * * * *

SEQUENCE LISTING

<160> NUMBER OF SEQ ID NOS: 17

<210> SEQ ID NO 1
<211> LENGTH: 3320
<212> TYPE: DNA
<213> ORGANISM: Porcine retrovirus

<400> SEQUENCE: 1

```
gaattcgcgg ccgcgtcgac agatgccttc ttctgcctga gattacaccc cactagccaa      60
ccactttttg ccttcgaatg gagagatcca ggtacgggaa gaaccgggca gctcacctgg     120
acccgactgc cccaagggtt caagaactcc ccgaccatct ttgacgaagc cctacacagg     180
gacctggcca acttcaggat ccaacaccct caggtgaccc tcctccagta cgtggatgac     240
ctgcttctgg cgggagccac caaacaggac tgcttagaag gtacgaaggc actactgctg     300
gaattgtctg acctaggcta cagagcctct gctaagaagg cccagatttg caggagagag     360
gtaacatact tggggtacag tttgcgggggc gggcagcgat ggctgacgga ggcacggaag     420
aaaactgtag tccagatacc ggccccaacc acagccaaac aagtgagaga gttttttgggg     480 acagctggat tttgcagact gtggatcccg gggtttgcga ccttagcagc cccactctac     540
ccgctaacca aagaaaaagg gggattctcc tgggctcctg agcaccagaa ggcatttgat     600
gctatcaaaa aggccctgct gagcgcacct gctctggccc tccctgacgt aactaaaccc     660
tttacccttt atgtggatga gcgtaaggga gtagcccgag gagttttaac ccaaacccta     720
ggaccatgga ggagacctgt tgcctacctg tcaaagaagc ttgatcctgt agccagtggt     780
tggcccgtat gtctgaaggc tatcgcagct gtggccatac tggtcaagga cgctgacaaa     840
ttgactttgg gacagaatat aactgtaata gcccccccatg cattggagaa catcgttcgg     900
cagcccccag accgatggat gaccaacgcc cgcatgaccc actatcaaag cctgcttctc     960
acagagaggg tcactttcgc tccaccagcc gctctcaacc ctgccactct tctgcctgaa    1020
gagactgatg aaccagtgac tcatgattgc catcaactat tgattgagga gactggggtc    1080
cgcaaggacc ttacagacat accgctgact ggagaagtgc taacctggtt cactgacgga    1140
agcagctatg tggtggaagg taagaggatg gctgggcgg cagtggtgga cgggacccgc    1200
acgatctggg ccagcagcct gccggaagga acttcagcgc aaaaggctga gctcatggcc    1260
ctcacgcaag ctttgcggct ggccgaaggg aaatccataa acatttatac ggacagcagg    1320
```

```
tatgcctttg cgactgcaca cgtacacggg gccatctata acaaaggggg gttgcttacc    1380
tcagcaggga gggaaataaa gaacaaagag gaaattctaa gcctattaga agccttacat    1440
ttgccaaaaa ggctagctat tatacactgt cctggacatc agaaagccaa agatctcata    1500
tctagaggga accagatggc tgaccgggtt gccaagcagg cagcccaggc tgttaacctt    1560
ctgcctataa tagaaacgcc caaagcccca gaacccagac gacagtacac cctagaagac    1620
tggcaagaga taaaaagat agaccagttc tctgagactc cggaggggac ctgctatacc     1680
tcatatggga aggaaatcct gccccacaaa gaagggttag aatatgtcca acagatacat    1740
cgtctaaccc acctaggaac taaacacctg cagcagttgg tcagaacatc cccttatcat    1800
gttctgaggc taccaggagt ggctgactcg gtggtcaaac attgtgtgcc ctgccagctg    1860
gttaatgcta atccttccag aatacctcca ggaaagagac taagggggaag ccacccaggc    1920 gctcactggg aagtggactt cactgaggta agccggcta aatacggaaa caaatatcta     1980 ttggttttg tagacacctt tcaggatgg gtagaggctt atcctactaa gaaagagact      2040
tcaaccgtgg tggctaagaa atactggag gaaattttc caagatttgg aatacctaag     2100 gtaataggt cagacaatgg tccagctttc gttgcccagg taagtcaggg actggccaag    2160
atattgggga ttgattggaa actgcattgt gcatacagac cccaaagctc aggacaggta    2220
gagaggatga atagaaccat taaagagacc cttaccaaat tgaccacaga gactggcatt    2280
aatgattgga tggctctcct gcccctttgtg ctttttaggg tgaggaacac ccctggacag    2340
tttgggctga cccccctatga attgctctac gggggaccc cccgttggc agaaattgcc     2400 tttgcacata gtgctgatgt gctgcttttcc cagcctttgt tctctaggct caaggcgctc    2460
gagtgggtga ggcagcgagc gtggaagcag ctccgggagg cctactcagg aggagacttg    2520
caagttccac atcgcttcca agttggagat tcagtctatg ttagacgcca ccgtgcagga    2580
aacctcgaga ctcggtggaa gggacccttat ctcgtacttt tgaccacacc aacgctgtg    2640 aaagtcgaag gaatccccac ctggatccat gcatccacg ttaagccggc gccacctccc     2700
gattcggggt ggaaagccga aaagactgaa atccccctta agcttcgcct ccatcgcgtg    2760
gttccttact ctgtcaataa ctcctcaagt taatggtaaa cgccttgtgg acagcccgaa    2820
ctcccataaa cccttatctc tcacctggtt acttactgac tccggtacag gtattaatat    2880
taacagcact caaggggagg ctcccttggg gacctggtgg cctgaattat atgtctgcct    2940
tcgatcagta atccctggtc tcaatgacca ggccacaccc cccgatgtac tccgtgctta    3000
cgggttttac gtttgcccag gaccccaaaa taatgaagaa tattgtggaa atcctcagga    3060
tttcctttgc aagcaatgga gctgcataac ttctaatgat gggaattgga atgtgccagt    3120
ctctcagcaa gacagagtaa gttactcttt tgttaacaat cctaccagtt ataatcaatt    3180
taattatggc catgggagat ggaaagattg gcaacagcgg gtacaaaaag atgtacgaaa    3240
taagcaaata agctgtcatt cgttagacct agattactta aaaataagtt tcactaaaaa    3300
aaaaaaaaaa aaaaaaaaa                                                 3320
```

<210> SEQ ID NO 2
<211> LENGTH: 8196
<212> TYPE: DNA
<213> ORGANISM: Porcine retrovirus

<400> SEQUENCE: 2

```
tgtgggcccc agcgcgcttg gaataaaaat cctcttgctg tttgcatcaa gaccgcttct      60
```

-continued

| | |
|---|---|
| cgtgagtgat ttggggtgtc gcctcttccg akcccggacg aggggggattg ttctttttact | 120 |
| ggcctttcat ttggtgcgtt ggccgggaaa tcctgcgacc acccccttaca cccgagaacc | 180 |
| gacttggagg taaagggatc ccctttggaa cgtgtgtgtg tgtcggccgg cgtctctgtt | 240 |
| ctgagtgtct gttttcggtg atgcgcgctt tcggtttgca gctgtcctct cagaccgtaa | 300 |
| ggactggagg actgtgatca gcagacgtgc taggaggatc acaggctgcc accctggggg | 360 |
| acgcccgggg aagtggggag agccaggac gcctggtggt ctcctactgt cggtcagagg | 420 |
| accgagttct gttgttgaag cgaaagcttc cccctccgcg gccgtccgac tcttttgcct | 480 |
| gcttgtggaa gacgcggacg ggtcgcgtgt gtctggatct gttggtttct gtctcgtgtg | 540 |
| tctttgtctt gtgcgtcctt gtctacagtt ttaatatggg acagacagtg actacccccc | 600 |
| ttagtttgac tctcgaccat tggactgaag ttagatccag ggctcataat ttgtcagttc | 660 |
| aggttaagaa gggaccttgg cagactttct gtgcctctga atggccaaca ttcgatgttg | 720 |
| gatggccatc agaggggacc tttaattctg aaattatcct ggctgttaag gcaatcattt | 780 |
| ttcagactgg acccggctct catcctgatc aggagcccta tatccttacg tggcaagatt | 840 |
| tggcagaaga tcctccgcca tgggttaaac catggctaaa taaccaaga aagccaggtc | 900 |
| cccgaatcct ggctcttgga gagaaaaaca acactcggc cgaaaaagtc gagccctctt | 960 |
| cctcgtatct accccgagat cgaggagccg ccgacttggc cggaaccccca acctgttccc | 1020 |
| ccacccccttt atccagcaca gggtgctgtg aggggacctc tgcccctcct ggagctccgg | 1080 |
| tggtggaggg acctgctgcc gggactcgga gccggagagg cgccacccccg gagcggacag | 1140 |
| acgagatcgc gatattaccg ctgcgcacct atggccctcc catgccaggg ggccaattgc | 1200 |
| agcccctcca gtattggccc ttttcttctg cagatctcta taattggaaa actaaccatc | 1260 |
| cccctttctc ggaggatccc caacgcctca cggggttggt ggagtcccctt atgttctctc | 1320 |
| accagcctac ttgggatgat tgtcaacagc tgctgcagac actcttcaca accgaggagc | 1380 |
| gagagagaat tctgttagag gctagaaaaa atgttcctgg ggccgacggg cgacccacgc | 1440 |
| agttgcaaaa tgagattgac atgggattc ccttgactcg ccccggttgg gactacaaca | 1500 |
| cggctgaagg taggagagc ttgaaaatct atcgccaggc tctggtggcg ggtctccggg | 1560 |
| gcgcctcaag acggcccact aatttggcta aggtaagaga ggtgatgcag ggaccgaacg | 1620 |
| aacctcccctc ggtatttctt gagaggctca tggaagcctt caggcggttc acccctttttg | 1680 |
| atcctacctc agaggcccag aaagcctcag tggccctggc cttcattggg cagtcggctc | 1740 |
| tggatatcag gaagaaactt cagagactgg aagggttaca ggaggctgag ttacgtgatc | 1800 |
| tagtgagaga ggcagagaag gtgtattaca aagggagac agaagaggag aaggaacaga | 1860 |
| gaaaagaaaa ggagagagaa gaaagggagg aaagacgtga tagacggcaa gagaagaatt | 1920 |
| tgactaagat cttggccgca gtggttgaag ggaagagcag cagggagaga gagagagatt | 1980 |
| ttaggaaaat taggtcaggc cctagacagt cagggaacct gggcaatagg accccactcg | 2040 |
| acaaggacca gtgtgcgtat tgtaaagaaa aaggacactg ggcaaggaac tgccccaaga | 2100 |
| agggaaacaa aggaccgaag tcctagctct agaagaagat aaagattagg ggagacgggt | 2160 |
| tcggaccccc tccccgagcc cagggtaact ttgaaggtgg aggggcaacc agttgagttc | 2220 |
| ctggttgata ccggagcgga gcattcagtg ctgctacaac cattaggaaa actaaaagaa | 2280 |
| aaaaaatcct gggtgatggg tgccacaggg caacggcagt atccatggac tacccgaaga | 2340 |
| accgttgact tgggagtggg acgggtaacc cactcgtttc tggtcatccc tgagtgccca | 2400 |
| gtaccccttc taggtagaga cttactgacc aagatgggag ctcaaatttc ttttgaacaa | 2460 |

-continued

```
ggaagaccag aagtgtctgt gaataacaaa cccatcactg tgttgaccct ccaattagat      2520
gatgaatatc gactatattc tccccaagta aagcctgatc aagatataca gtcctggttg      2580
gagcagtttc cccaagcctg ggcagaaacc gcagggatgg gtttggcaaa gcaagttccc      2640
ccacaggtta ttcaactgaa ggccagtgct acaccagtat cagtcagaca gtacccttg       2700 agtagagagg ctcgagaagg aatttggccg catgttcaaa gattaatcca acagggcatc      2760
ctagttcctg tccaatcccc ttggaatact cccctgctac cggttaggaa gcctgggacc      2820
aatgattatc gaccagtaca ggacttgaga gaggtcaata aaagggtgca ggacatacac      2880
ccaacggtcc cgaacccttta taacctcttg agcgccctcc cgcctgaacg gaactggtac     2940
acagtattgg acttaaaaga tgccttcttc tgcctgagat tacacccccac tagccaacca    3000 cttttttgcct tcgaatggag agatccaggt acgggaagaa ccgggcagct cacctggacc    3060
cgactgcccc aagggttcaa gaactccccg accatctttg acgaagccct acacagggac     3120
ctggccaact tcaggatcca acaccctcag gtgaccctcc tccagtacgt ggatgacctg     3180
cttctggcgg gagccaccaa acaggactgc ttagaaggta cgaaggcact actgctggaa     3240
ttgtctgacc taggctacag agcctctgct aagaaggccc agatttgcag agagaggta     3300 acatacttgg ggtacagttt gcggggcggg cagcgatggc tgacggaggc acggaagaaa    3360
actgtagtcc agataccggc cccaaccaca gccaaacaag tgagagagtt tttggggaca     3420
gctggatttt gcagactgtg atcccgggg tttgcgacct tagcagcccc actctacccg      3480
ctaaccaaag aaaaggggg attctcctgg gctcctgagc accagaaggc atttgatgct     3540
atcaaaaagg ccctgctgag cgcacctgct ctggccctcc ctgacgtaac taaacccttt    3600 acccttatg tggatgagcg taagggagta gcccgaggag ttttaaccca aaccctagga    3660
ccatggagga gacctgttgc ctacctgtca aagaagcttg atcctgtagc cagtggttgg    3720
cccgtatgtc tgaaggctat cgcagctgtg ccatactgg tcaaggacgc tgacaaattg     3780
actttgggac agaatataac tgtaatagcc ccccatgcat tggagaacat cgttcggcag    3840 ccccccagacc gatggatgac caacgcccgc atgacccact atcaaagcct gcttctcaca    3900
gagagggtca ctttcgctcc accagccgct ctcaaccctg ccactcttct gcctgaagag    3960
actgatgaac cagtgactca tgattgccat caactattga ttgaggagac tggggtccgc    4020
aaggacctta cagacatacc gctgactgga gaagtgctaa cctggttcac tgacggaagc    4080
agctatgtgg tggaaggtaa gaggatggct ggggcggcag tggtgacgg gacccgcacg     4140 atctgggcca gcagcctgcc ggaaggaact tcagcgcaaa aggctgagct catggccctc    4200
acgcaagctt tgcggctggc cgaagggaaa tccataaaca tttatacgga cagcaggtat    4260 gccttttgcga ctgcacacgt acacggggcc atctataaac aaaggggggtt gcttacctca  4320 gcagggaggg aaataaagaa caaagaggaa attctaagcc tattagaagc cttacattg     4380 ccaaaaaggc tagctattat acactgtcct ggacatcaga aagccaaaga tctcatatct    4440
agagggaacc agatggctga ccgggttgcc aagcaggcag cccaggctgt taaccttctg    4500
cctataatag aaacgcccaa agccccagaa cccagacgac agtacaccct agaagactgg    4560
caagagataa aaagatagaa ccagttctct gagactccgg aggggacctg ctatacctca    4620
tatgggaagg aaatcctgcc ccacaaagaa gggttagaat atgtccaaca gatacatcgt    4680
ctaacccacc taggaactaa acacctgcag cagttggtca gaacatcccc ttatcatgtt    4740
ctgaggctac caggagtggc tgactcggtg gtcaaacatt gtgtgccctg ccagctggtt    4800
```

```
aatgctaatc cttccagaat acctccagga aagagactaa ggggaagcca cccaggcgct   4860
cactgggaag tggacttcac tgaggtaaag ccggctaaat acggaaacaa atatctattg   4920
gtttttgtag acaccttttc aggatgggta gaggcttatc ctactaagaa agagacttca   4980
accgtggtgg ctaagaaaat actggaggaa attttccaa gatttggaat acctaaggta   5040
atagggtcag acaatggtcc agctttcgtt gcccaggtaa gtcagggact ggccaagata   5100
ttggggattg attggaaact gcattgtgca tacagacccc aaagctcagg acaggtagag   5160
aggatgaata gaaccattaa agagaccctt accaaattga ccacagagac tggcattaat   5220
gattggatgg ctctcctgcc ctttgtgctt tttagggtga ggaacacccc tggacagttt   5280
gggctgaccc cctatgaatt gctctacggg ggaccccccc cgttggcaga aattgccttt   5340
gcacatagtg ctgatgtgct gctttcccag cctttgttct ctaggctcaa ggcgctcgag   5400
tgggtgaggc agcgagcgtg gaagcagctc cgggaggcct actcaggagg agacttgcaa   5460
gttccacatc gcttccaagt tggagattca gtctatgtta gacgccaccg tgcaggaaac   5520
ctcgagactc ggtggaaggg accttatctc gtacttttga ccacaccaac ggctgtgaaa   5580
gtcgaaggaa tccccacctg gatccatgca tcccacgtta agcyggcgcc acctcccgac   5640
tcggggtgga gagccgaaaa gactgagaat ccccttaagc ttcgcctcca tcgcctggtt   5700
ccttactcta acaataactc cccaggccag tagtaaacgc ttatagaca gctcgaaccc   5760
ccatagacct ttatcccctta cctggctgat tattgaccct gatacgggtg tcactgtaaa   5820
tagcactcga ggtgttgctc ctagaggcac ctggtggcct gaactgcatt tctgcctccg   5880
attgattaac cccgctgtta aragcacacc tcccaaccta gtccgtagtt atgggttcta   5940
ttgctgccca ggcacagaga aagagaaata ctgtgggggt tctggggaat ccttctgtag   6000
gagatggagc tgcgtcacct ccaacgatgg agactggaaa tggccgatct ctctccagga   6060
ccgggtaaaa ttctccttg tcaattccgg cccgggcaag tacaaaatga tgaaactata   6120
taaagataag agctgctccc catcagactt agattatcta aagataagtt tcactgaaag   6180
gaaaacagga aaatattcaa aagtggataa atggtatgag ctggggaata gttttttatt   6240
atatggcggg ggagcagggt ccactttaac cattcgcctt aggatagaga cggggacaga   6300
accccctgtg gcaatgggac ccgataaagt actggctgaa caggggcccc cggcctggga   6360
gccaccgcat aacttgccgg tgccccaatt aacctcgctg cggcctgaca taacacagcc   6420
gcctagcaac agtaccactg gattgattcc taccaacacg cctagaaact ccccaggtgt   6480
tcctgttaag acaggacaga gactcttcag tctcatccag ggagctttcc aagccatcaa   6540
ctccaccgac cctgatgcca cttcttcttg ttggctttgt ctatcctcag ggcctcctta   6600
ttatgagggg atggctaaag aaagaaaatt caatgtgacc aaagagcata gaaatcaatg   6660
tacatgggg tcccgaaata agcttaccct cactgaagtt tccgggaagg ggacatgcat   6720
aggaaaagct cccccatccc accaacacct ttgctatagt actgtggttt atgagcaggc   6780
ctcagaaaat cagtatttag tacctggtta taacaggtgg tgggcatgca atactgggtt   6840
aaccccctgt gtttccacct cagtcttcaa ccaatccaaa gatttctgtg tcatggtcca   6900
aatcgtcccc cgagtgtact accatcctga ggaagtggtc cttgatgaat atgactatcg   6960
gtataaccga ccaaaaagag aacccgtatc ccttacccta gctgtaatgc tcggattagg   7020
gacggccgtt ggcgtaggaa cagggacagc tgccctgatc acaggaccac agcagctaga   7080
gaaaggactt ggtgagctac atgcggccat gacagaagat ctccgagcct taaggagtc   7140
tgttagcaac ctagaagagt ccctgacttc tttgtctgaa gtggttctac agaaccggag   7200
```

-continued

```
gggattagat ctgctgtttc taagagaagg tgggttatgt gcagccttaa aagaagaatg      7260
ttgcttctat gtagatcact caggagccat cagagactcc atgaacaagc ttagaaaaaa      7320
gttagagagg cgtcgaaggg aaagagaggc tgaccagggg tggtttgaag gatggttcaa      7380
caggtctcct tggatgacca ccctgctttc tgctctgacg gggcccctag tagtcctgct      7440
cctgttactt acagttgggc cttgcttaat taataggttt gttgcctttg ttagagaacg      7500
agtgagtgca gtccagatca tggtacttag gcaacagtac caaggccttc tgagccaagg      7560
agaaactgac ctctagcctt cccagttcta agattagaac tattaacaag acaagaagtg      7620
gggaatgaaa ggatgaaaat gcaacctaac cctcccagaa cccaggaagt taataaaaag      7680
ctctaaatgc ccccgaattm cagaccctgc tggctgccag taaataggta gaaggtcaca      7740
cttcctattg ttccagggcc tgctatcctg gcctaagtaa gataacagga aatgagttga      7800
ctaatcgctt atctggattc tgtaaaactg actggcacca tagaagaatt gattacacat      7860
tgacagccct agtgacctat ctcaactgca atctgtcact ctgcccagga gcccacgcag      7920
atgcggacct ccgagctat tttaaaatga ttggtccacg gagcgcgggc tctcgatatt       7980
ttaaaatgat tggtccatgg agcgcgggct ctcgatattt taaaatgatt ggtttgtgac      8040
gcacaggctt tgttgtgaac cccataaaag ctgtcccgat tccgcactcg ggccgcagt       8100 cctctacccc tgcgtggtgt acgactgtgg gccccagcgc gcttggaata aaaatcctct      8160
tgctgtttgc atcaaaaaaa aaaaaaaaaa aaaaaa                                8196

<210> SEQ ID NO 3
<211> LENGTH: 8209
<212> TYPE: DNA
<213> ORGANISM: Porcine retrovirus
<220> FEATURE:
<221> NAME/KEY: CDS
<222> LOCATION: (588)..(2159)
<221> NAME/KEY: CDS
<222> LOCATION: (2163)..(5744)

<400> SEQUENCE: 3
gtggtgtacg actgtgggcc ccagcgcgct tggaataaaa atcctcttgc tgtttgcatc       60
aagaccgctt ctcgtgagtg atttggggtg tcgcctcttc cgagcccgga cgagggggat      120 tgttcttta ctggcctttc atttggtgcg ttggccggga atcctgcga ccaccccctta      180 cacccgagaa ccgacttgga ggtaaaggga tccccttggg aacgtgtgtg tgtgtcggcc      240
ggcgtctctg ttctgagtgt ctgttttcgg tgatgcgcgc tttcggtttg cagctgtcct      300
ctcagaccgt aaggactgga ggactgtgat cagcagacgt gctaggagga tcacaggctg      360
ccaccctggg ggacgccccg ggaggtgggg agagccaggg acgcctggtg gtctcctact      420
gtcggtcaga ggaccgagtt ctgttgttga agcgaaagct tcccccctccg cggccgtccg     480 actcttttgc ctgcttgtgg aagacgcgga cgggtcgcgt gtgtctggat ctgttggttt     540
ctgtctcgtg tgtctttgtc ttgtgcgtcc ttgtctacag ttttaat atg gga cag        596
                                                     Met Gly Gln
                                                      1 aca gtg act acc ccc ctt agt ttg act ctc gac cat tgg act gaa gtt        644
Thr Val Thr Thr Pro Leu Ser Leu Thr Leu Asp His Trp Thr Glu Val
  5                  10                  15 aga tcc agg gct cat aat ttg tca gtt cag gtt aag aag gga cct tgg        692
Arg Ser Arg Ala His Asn Leu Ser Val Gln Val Lys Lys Gly Pro Trp
 20                  25                  30                  35 cag act ttc tgt gcc tct gaa tgg cca aca ttc gat gtt gga tgg cca        740
```

-continued

```
              Gln Thr Phe Cys Ala Ser Glu Trp Pro Thr Phe Asp Val Gly Trp Pro
                              40                  45                  50 tca gag ggg acc ttt aat tct gaa att atc ctg gct gtt aag gca atc           788
Ser Glu Gly Thr Phe Asn Ser Glu Ile Ile Leu Ala Val Lys Ala Ile
            55                  60                  65 att ttt cag act gga ccc ggc tct cat cct gat cag gag ccc tat atc           836
Ile Phe Gln Thr Gly Pro Gly Ser His Pro Asp Gln Glu Pro Tyr Ile
            70                  75                  80 ctt acg tgg caa gat ttg gca gaa gat cct ccg cca tgg gtt aaa cca           884
Leu Thr Trp Gln Asp Leu Ala Glu Asp Pro Pro Pro Trp Val Lys Pro
        85                  90                  95 tgg cta aat aaa cca aga aag cca ggt ccc cga atc ctg gct ctt gga           932
Trp Leu Asn Lys Pro Arg Lys Pro Gly Pro Arg Ile Leu Ala Leu Gly
100                 105                 110                 115 gag aaa aac aaa cac tcg gcc gaa aaa gtc gag ccc tct tcc tcg tat           980
Glu Lys Asn Lys His Ser Ala Glu Lys Val Glu Pro Ser Ser Ser Tyr
                120                 125                 130 cta ccc cga gat cga gga gcc gcc gac ttg gcc gga acc cca acc tgt          1028
Leu Pro Arg Asp Arg Gly Ala Ala Asp Leu Ala Gly Thr Pro Thr Cys
                135                 140                 145 tcc ccc acc ccc tta tcc agc aca ggg tgc tgt gag ggg acc tct gcc          1076
Ser Pro Thr Pro Leu Ser Ser Thr Gly Cys Cys Glu Gly Thr Ser Ala
            150                 155                 160 cct cct gga gct ccg gtg gtg gag gga cct gct gcc ggg act cgg agc          1124
Pro Pro Gly Ala Pro Val Val Glu Gly Pro Ala Ala Gly Thr Arg Ser
            165                 170                 175 cgg aga ggc gcc acc ccg gag cgg aca gac gag atc gcg ata tta ccg          1172
Arg Arg Gly Ala Thr Pro Glu Arg Thr Asp Glu Ile Ala Ile Leu Pro
180                 185                 190                 195 ctg cgc acc tat ggc cct ccc atg cca ggg ggc caa ttg cag ccc ctc          1220
Leu Arg Thr Tyr Gly Pro Pro Met Pro Gly Gly Gln Leu Gln Pro Leu
                200                 205                 210 cag tat tgg ccc ttt tct tct gca gat ctc tat aat tgg aaa act aac          1268
Gln Tyr Trp Pro Phe Ser Ser Ala Asp Leu Tyr Asn Trp Lys Thr Asn
            215                 220                 225 cat ccc cct ttc tcg gag gat ccc caa cgc ctc acg ggg ttg gtg gag          1316
His Pro Pro Phe Ser Glu Asp Pro Gln Arg Leu Thr Gly Leu Val Glu
            230                 235                 240 tcc ctt atg ttc tct cac cag cct act tgg gat gat tgt caa cag ctg          1364
Ser Leu Met Phe Ser His Gln Pro Thr Trp Asp Asp Cys Gln Gln Leu
        245                 250                 255 ctg cag aca ctc ttc aca acc gag gag cga gag aga att ctg tta gag          1412
Leu Gln Thr Leu Phe Thr Thr Glu Glu Arg Glu Arg Ile Leu Leu Glu
260                 265                 270                 275 gct aga aaa aat gtt cct ggg gcc gac ggg cga ccc acg cag ttg caa          1460
Ala Arg Lys Asn Val Pro Gly Ala Asp Gly Arg Pro Thr Gln Leu Gln
                280                 285                 290 aat gag att gac atg gga ttt ccc ttg act cgc ccc ggt tgg gac tac          1508
Asn Glu Ile Asp Met Gly Phe Pro Leu Thr Arg Pro Gly Trp Asp Tyr
            295                 300                 305 aac acg gct gaa ggt agg gag agc ttg aaa atc tat cgc cag gct ctg          1556
Asn Thr Ala Glu Gly Arg Glu Ser Leu Lys Ile Tyr Arg Gln Ala Leu
            310                 315                 320 gtg gcg ggt ctc cgg ggc gcc tca aga cgg ccc act aat ttg gct aag          1604
Val Ala Gly Leu Arg Gly Ala Ser Arg Arg Pro Thr Asn Leu Ala Lys
        325                 330                 335 gta aga gag gtg atg cag gga ccg aac gaa cct ccc tcg gta ttt ctt          1652
Val Arg Glu Val Met Gln Gly Pro Asn Glu Pro Pro Ser Val Phe Leu
340                 345                 350                 355
```

-continued

| | |
|---|---|
| gag agg ctc atg gaa gcc ttc agg cgg ttc acc cct ttt gat cct acc<br>Glu Arg Leu Met Glu Ala Phe Arg Arg Phe Thr Pro Phe Asp Pro Thr<br>            360                 365                 370 | 1700 |
| tca gag gcc cag aaa gcc tca gtg gcc ctg gcc ttc att ggg cag tcg<br>Ser Glu Ala Gln Lys Ala Ser Val Ala Leu Ala Phe Ile Gly Gln Ser<br>    375                 380                 385 | 1748 |
| gct ctg gat atc agg aag aaa ctt cag aga ctg gaa ggg tta cag gag<br>Ala Leu Asp Ile Arg Lys Lys Leu Gln Arg Leu Glu Gly Leu Gln Glu<br>390                 395                 400 | 1796 |
| gct gag tta cgt gat cta gtg aga gag gca gag aag gtg tat tac aga<br>Ala Glu Leu Arg Asp Leu Val Arg Glu Ala Glu Lys Val Tyr Tyr Arg<br>    405                 410                 415 | 1844 |
| agg gag aca gaa gag gag aag gaa cag aga aaa gaa aag gag aga gaa<br>Arg Glu Thr Glu Glu Glu Lys Glu Gln Arg Lys Glu Lys Glu Arg Glu<br>420                 425                 430                 435 | 1892 |
| gaa agg gag gaa aga cgt gat aga cgg caa gag aag aat ttg act aag<br>Glu Arg Glu Glu Arg Arg Asp Arg Arg Gln Glu Lys Asn Leu Thr Lys<br>            440                 445                 450 | 1940 |
| atc ttg gcc gca gtg gtt gaa ggg aag agc agc agg gag aga gag aga<br>Ile Leu Ala Ala Val Val Glu Gly Lys Ser Ser Arg Glu Arg Glu Arg<br>    455                 460                 465 | 1988 |
| gat ttt agg aaa att agg tca ggc cct aga cag tca ggg aac ctg ggc<br>Asp Phe Arg Lys Ile Arg Ser Gly Pro Arg Gln Ser Gly Asn Leu Gly<br>470                 475                 480 | 2036 |
| aat agg acc cca ctc gac aag gac cag tgt gcg tat tgt aaa gaa aaa<br>Asn Arg Thr Pro Leu Asp Lys Asp Gln Cys Ala Tyr Cys Lys Glu Lys<br>    485                 490                 495 | 2084 |
| gga cac tgg gca agg aac tgc ccc aag aag gga aac aaa gga ccg aag<br>Gly His Trp Ala Arg Asn Cys Pro Lys Lys Gly Asn Lys Gly Pro Lys<br>500                 505                 510                 515 | 2132 |
| gtc cta gct cta gaa gaa gat aaa gat tag ggg aga cgg ggt tcg gac<br>Val Leu Ala Leu Glu Glu Asp Lys Asp     Gly Arg Arg Gly Ser Asp<br>            520                 525                 530 | 2180 |
| ccc ctc ccc gag ccc agg gta act ttg aag gtg gag ggg caa cca gtt<br>Pro Leu Pro Glu Pro Arg Val Thr Leu Lys Val Glu Gly Gln Pro Val<br>            535                 540                 545 | 2228 |
| gag ttc ctg gtt gat acc gga gcg gag cat tca gtg ctg cta caa cca<br>Glu Phe Leu Val Asp Thr Gly Ala Glu His Ser Val Leu Leu Gln Pro<br>    550                 555                 560 | 2276 |
| tta gga aaa cta aaa gaa aaa aaa tcc tgg gtg atg ggt gcc aca ggg<br>Leu Gly Lys Leu Lys Glu Lys Lys Ser Trp Val Met Gly Ala Thr Gly<br>565                 570                 575 | 2324 |
| caa cgg cag tat cca tgg act acc cga aga acc gtt gac ttg gga gtg<br>Gln Arg Gln Tyr Pro Trp Thr Thr Arg Arg Thr Val Asp Leu Gly Val<br>580                 585                 590 | 2372 |
| gga cgg gta acc cac tcg ttt ctg gtc atc cct gag tgc cca gta ccc<br>Gly Arg Val Thr His Ser Phe Leu Val Ile Pro Glu Cys Pro Val Pro<br>595                 600                 605                 610 | 2420 |
| ctt cta ggt aga gac tta ctg acc aag atg gga gct caa att tct ttt<br>Leu Leu Gly Arg Asp Leu Leu Thr Lys Met Gly Ala Gln Ile Ser Phe<br>            615                 620                 625 | 2468 |
| gaa caa gga aga cca gaa gtg tct gtg aat aac aaa ccc atc act gtg<br>Glu Gln Gly Arg Pro Glu Val Ser Val Asn Asn Lys Pro Ile Thr Val<br>    630                 635                 640 | 2516 |
| ttg acc ctc caa tta gat gat gaa tat cga cta tat tct ccc caa gta<br>Leu Thr Leu Gln Leu Asp Asp Glu Tyr Arg Leu Tyr Ser Pro Gln Val<br>645                 650                 655 | 2564 |
| aag cct gat caa gat ata cag tcc tgg ttg gag cag ttt ccc caa gcc<br>Lys Pro Asp Gln Asp Ile Gln Ser Trp Leu Glu Gln Phe Pro Gln Ala<br>    660                 665                 670 | 2612 |

-continued

```
tgg gca gaa acc gca ggg atg ggt ttg gca aag caa gtt ccc cca cag    2660
Trp Ala Glu Thr Ala Gly Met Gly Leu Ala Lys Gln Val Pro Pro Gln
675                 680                 685                 690 gtt att caa ctg aag gcc agt gct aca cca gta tca gtc aga cag tac    2708
Val Ile Gln Leu Lys Ala Ser Ala Thr Pro Val Ser Val Arg Gln Tyr
            695                 700                 705 ccc ttg agt aga gag gct cga gaa gga att tgg ccg cat gtt caa aga    2756
Pro Leu Ser Arg Glu Ala Arg Glu Gly Ile Trp Pro His Val Gln Arg
        710                 715                 720 tta atc caa cag ggc atc cta gtt cct gtc caa tcc cct tgg aat act    2804
Leu Ile Gln Gln Gly Ile Leu Val Pro Val Gln Ser Pro Trp Asn Thr
    725                 730                 735 ccc ctg cta ccg gtt agg aag cct ggg acc aat gat tat cga cca gta    2852
Pro Leu Leu Pro Val Arg Lys Pro Gly Thr Asn Asp Tyr Arg Pro Val
740                 745                 750 cag gac ttg aga gag gtc aat aaa agg gtg cag gac ata cac cca acg    2900
Gln Asp Leu Arg Glu Val Asn Lys Arg Val Gln Asp Ile His Pro Thr
755                 760                 765                 770 gtc ccg aac cct tat aac ctc ttg agc gcc ctc ccg cct gaa cgg aac    2948
Val Pro Asn Pro Tyr Asn Leu Leu Ser Ala Leu Pro Pro Glu Arg Asn
            775                 780                 785 tgg tac aca gta ttg gac tta aaa gat gcc ttc ttc tgc ctg aga tta    2996
Trp Tyr Thr Val Leu Asp Leu Lys Asp Ala Phe Phe Cys Leu Arg Leu
        790                 795                 800 cac ccc act agc caa cca ctt ttt gcc ttc gaa tgg aga gat cca ggt    3044
His Pro Thr Ser Gln Pro Leu Phe Ala Phe Glu Trp Arg Asp Pro Gly
    805                 810                 815 acg gga aga acc ggg cag ctc acc tgg acc cga ctg ccc caa ggg ttc    3092
Thr Gly Arg Thr Gly Gln Leu Thr Trp Thr Arg Leu Pro Gln Gly Phe
820                 825                 830 aag aac tcc ccg acc atc ttt gac gaa gcc cta cac agg gac ctg gcc    3140
Lys Asn Ser Pro Thr Ile Phe Asp Glu Ala Leu His Arg Asp Leu Ala
835                 840                 845                 850 aac ttc agg atc caa cac cct cag gtg acc ctc ctc cag tac gtg gat    3188
Asn Phe Arg Ile Gln His Pro Gln Val Thr Leu Leu Gln Tyr Val Asp
            855                 860                 865 gac ctg ctt ctg gcg gga gcc acc aaa cag gac tgc tta gaa ggt acg    3236
Asp Leu Leu Leu Ala Gly Ala Thr Lys Gln Asp Cys Leu Glu Gly Thr
        870                 875                 880 aag gca cta ctg ctg gaa ttg tct gac cta ggc tac aga gcc tct gct    3284
Lys Ala Leu Leu Leu Glu Leu Ser Asp Leu Gly Tyr Arg Ala Ser Ala
    885                 890                 895 aag aag gcc cag att tgc agg aga gag gta aca tac ttg ggg tac agt    3332
Lys Lys Ala Gln Ile Cys Arg Arg Glu Val Thr Tyr Leu Gly Tyr Ser
900                 905                 910 ttg cgg ggc ggg cag cga tgg ctg acg gag gca cgg aag aaa act gta    3380
Leu Arg Gly Gly Gln Arg Trp Leu Thr Glu Ala Arg Lys Lys Thr Val
915                 920                 925                 930 gtc cag ata ccg gcc cca acc aca gcc aaa caa gtg aga gag ttt ttg    3428
Val Gln Ile Pro Ala Pro Thr Thr Ala Lys Gln Val Arg Glu Phe Leu
            935                 940                 945 ggg aca gct gga ttt tgc aga ctg tgg atc ccg ggg ttt gcg acc tta    3476
Gly Thr Ala Gly Phe Cys Arg Leu Trp Ile Pro Gly Phe Ala Thr Leu
        950                 955                 960 gca gcc cca ctc tac ccg cta acc aaa gaa aaa ggg gga ttc tcc tgg    3524
Ala Ala Pro Leu Tyr Pro Leu Thr Lys Glu Lys Gly Gly Phe Ser Trp
    965                 970                 975 gct cct gag cac cag aag gca ttt gat gct atc aaa aag gcc ctg ctg    3572
Ala Pro Glu His Gln Lys Ala Phe Asp Ala Ile Lys Lys Ala Leu Leu
```

-continued

|  |  |  |  |  |  |  |  |  |  |  |
|---|---|---|---|---|---|---|---|---|---|---|
| 980 | | | 985 | | | 990 | | | | |
| agc | gca | cct | gct | ctg | gcc | ctc | cct | gac | gta | act | aaa | ccc | ttt | acc | 3617 |
| Ser | Ala | Pro | Ala | Leu | Ala | Leu | Pro | Asp | Val | Thr | Lys | Pro | Phe | Thr | |
| 995 | | | | 1000 | | | | 1005 | | | | | | | |
| ctt | tat | gtg | gat | gag | cgt | aag | gga | gta | gcc | cga | gga | gtt | tta | acc | 3662 |
| Leu | Tyr | Val | Asp | Glu | Arg | Lys | Gly | Val | Ala | Arg | Gly | Val | Leu | Thr | |
| 1010 | | | | 1015 | | | | 1020 | | | | | | | |
| caa | acc | cta | gga | cca | tgg | agg | aga | cct | gtt | gcc | tac | ctg | tca | aag | 3707 |
| Gln | Thr | Leu | Gly | Pro | Trp | Arg | Arg | Pro | Val | Ala | Tyr | Leu | Ser | Lys | |
| 1025 | | | | 1030 | | | | 1035 | | | | | | | |
| aag | ctt | gat | cct | gta | gcc | agt | ggt | tgg | ccc | gta | tgt | ctg | aag | gct | 3752 |
| Lys | Leu | Asp | Pro | Val | Ala | Ser | Gly | Trp | Pro | Val | Cys | Leu | Lys | Ala | |
| 1040 | | | | 1045 | | | | 1050 | | | | | | | |
| atc | gca | gct | gtg | gcc | ata | ctg | gtc | aag | gac | gct | gac | aaa | ttg | act | 3797 |
| Ile | Ala | Ala | Val | Ala | Ile | Leu | Val | Lys | Asp | Ala | Asp | Lys | Leu | Thr | |
| 1055 | | | | 1060 | | | | 1065 | | | | | | | |
| ttg | gga | cag | aat | ata | act | gta | ata | gcc | ccc | cat | gca | ttg | gag | aac | 3842 |
| Leu | Gly | Gln | Asn | Ile | Thr | Val | Ile | Ala | Pro | His | Ala | Leu | Glu | Asn | |
| 1070 | | | | 1075 | | | | 1080 | | | | | | | |
| atc | gtt | cgg | cag | ccc | cca | gac | cga | tgg | atg | acc | aac | gcc | cgc | atg | 3887 |
| Ile | Val | Arg | Gln | Pro | Pro | Asp | Arg | Trp | Met | Thr | Asn | Ala | Arg | Met | |
| 1085 | | | | 1090 | | | | 1095 | | | | | | | |
| acc | cac | tat | caa | agc | ctg | ctt | ctc | aca | gag | agg | gtc | act | ttc | gct | 3932 |
| Thr | His | Tyr | Gln | Ser | Leu | Leu | Leu | Thr | Glu | Arg | Val | Thr | Phe | Ala | |
| 1100 | | | | 1105 | | | | 1110 | | | | | | | |
| cca | cca | gcc | gct | ctc | aac | cct | gcc | act | ctt | ctg | cct | gaa | gag | act | 3977 |
| Pro | Pro | Ala | Ala | Leu | Asn | Pro | Ala | Thr | Leu | Leu | Pro | Glu | Glu | Thr | |
| 1115 | | | | 1120 | | | | 1125 | | | | | | | |
| gat | gaa | cca | gtg | act | cat | gat | tgc | cat | caa | cta | ttg | att | gag | gag | 4022 |
| Asp | Glu | Pro | Val | Thr | His | Asp | Cys | His | Gln | Leu | Leu | Ile | Glu | Glu | |
| 1130 | | | | 1135 | | | | 1140 | | | | | | | |
| act | ggg | gtc | cgc | aag | gac | ctt | aca | gac | ata | ccg | ctg | act | gga | gaa | 4067 |
| Thr | Gly | Val | Arg | Lys | Asp | Leu | Thr | Asp | Ile | Pro | Leu | Thr | Gly | Glu | |
| 1145 | | | | 1150 | | | | 1155 | | | | | | | |
| gtg | cta | acc | tgg | ttc | act | gac | gga | agc | agc | tat | gtg | gtg | gaa | ggt | 4112 |
| Val | Leu | Thr | Trp | Phe | Thr | Asp | Gly | Ser | Ser | Tyr | Val | Val | Glu | Gly | |
| 1160 | | | | 1165 | | | | 1170 | | | | | | | |
| aag | agg | atg | gct | ggg | gcg | gca | gtg | gtg | gac | ggg | acc | cgc | acg | atc | 4157 |
| Lys | Arg | Met | Ala | Gly | Ala | Ala | Val | Val | Asp | Gly | Thr | Arg | Thr | Ile | |
| 1175 | | | | 1180 | | | | 1185 | | | | | | | |
| tgg | gcc | agc | agc | ctg | ccg | gaa | gga | act | tca | gcg | caa | aag | gct | gag | 4202 |
| Trp | Ala | Ser | Ser | Leu | Pro | Glu | Gly | Thr | Ser | Ala | Gln | Lys | Ala | Glu | |
| 1190 | | | | 1195 | | | | 1200 | | | | | | | |
| ctc | atg | gcc | ctc | acg | caa | gct | ttg | cgg | ctg | gcc | gaa | ggg | aaa | tcc | 4247 |
| Leu | Met | Ala | Leu | Thr | Gln | Ala | Leu | Arg | Leu | Ala | Glu | Gly | Lys | Ser | |
| 1205 | | | | 1210 | | | | 1215 | | | | | | | |
| ata | aac | att | tat | acg | gac | agc | agg | tat | gcc | ttt | gcg | act | gca | cac | 4292 |
| Ile | Asn | Ile | Tyr | Thr | Asp | Ser | Arg | Tyr | Ala | Phe | Ala | Thr | Ala | His | |
| 1220 | | | | 1225 | | | | 1230 | | | | | | | |
| gta | cac | ggg | gcc | atc | tat | aaa | caa | agg | ggg | ttg | ctt | acc | tca | gca | 4337 |
| Val | His | Gly | Ala | Ile | Tyr | Lys | Gln | Arg | Gly | Leu | Leu | Thr | Ser | Ala | |
| 1235 | | | | 1240 | | | | 1245 | | | | | | | |
| ggg | agg | gaa | ata | aag | aac | aaa | gag | gaa | att | cta | agc | cta | tta | gaa | 4382 |
| Gly | Arg | Glu | Ile | Lys | Asn | Lys | Glu | Glu | Ile | Leu | Ser | Leu | Leu | Glu | |
| 1250 | | | | 1255 | | | | 1260 | | | | | | | |
| gcc | tta | cat | ttg | cca | aaa | agg | cta | gct | att | ata | cac | tgt | cct | gga | 4427 |
| Ala | Leu | His | Leu | Pro | Lys | Arg | Leu | Ala | Ile | Ile | His | Cys | Pro | Gly | |
| 1265 | | | | 1270 | | | | 1275 | | | | | | | |
| cat | cag | aaa | gcc | aaa | gat | ctc | ata | tct | aga | ggg | aac | cag | atg | gct | 4472 |

```
His Gln Lys Ala Lys Asp Leu Ile Ser Arg Gly Asn Gln Met Ala
1280                1285                1290 gac cgg gtt gcc aag cag gca gcc cag gct gtt aac ctt ctg cct      4517
Asp Arg Val Ala Lys Gln Ala Ala Gln Ala Val Asn Leu Leu Pro
1295                1300                1305 ata ata gaa acg ccc aaa gcc cca gaa ccc aga cga cag tac acc      4562
Ile Ile Glu Thr Pro Lys Ala Pro Glu Pro Arg Arg Gln Tyr Thr
1310                1315                1320 cta gaa gac tgg caa gag ata aaa aag ata gac cag ttc tct gag      4607
Leu Glu Asp Trp Gln Glu Ile Lys Lys Ile Asp Gln Phe Ser Glu
1325                1330                1335 act ccg gag ggg acc tgc tat acc tca tat ggg aag gaa atc ctg      4652
Thr Pro Glu Gly Thr Cys Tyr Thr Ser Tyr Gly Lys Glu Ile Leu
1340                1345                1350 ccc cac aaa gaa ggg tta gaa tat gtc caa cag ata cat cgt cta      4697
Pro His Lys Glu Gly Leu Glu Tyr Val Gln Gln Ile His Arg Leu
1355                1360                1365 acc cac cta gga act aaa cac ctg cag cag ttg gtc aga aca tcc      4742
Thr His Leu Gly Thr Lys His Leu Gln Gln Leu Val Arg Thr Ser
1370                1375                1380 cct tat cat gtt ctg agg cta cca gga gtg gct gac tcg gtg gtc      4787
Pro Tyr His Val Leu Arg Leu Pro Gly Val Ala Asp Ser Val Val
1385                1390                1395 aaa cat tgt gtg ccc tgc cag ctg gtt aat gct aat cct tcc aga      4832
Lys His Cys Val Pro Cys Gln Leu Val Asn Ala Asn Pro Ser Arg
1400                1405                1410 ata cct cca gga aag aga cta agg gga agc cac cca ggc gct cac      4877
Ile Pro Pro Gly Lys Arg Leu Arg Gly Ser His Pro Gly Ala His
1415                1420                1425 tgg gaa gtg gac ttc act gag gta aag ccg gct aaa tac gga aac      4922
Trp Glu Val Asp Phe Thr Glu Val Lys Pro Ala Lys Tyr Gly Asn
1430                1435                1440 aaa tat cta ttg gtt ttt gta gac acc ttt tca gga tgg gta gag      4967
Lys Tyr Leu Leu Val Phe Val Asp Thr Phe Ser Gly Trp Val Glu
1445                1450                1455 gct tat cct act aag aaa gag act tca acc gtg gtg gct aag aaa      5012
Ala Tyr Pro Thr Lys Lys Glu Thr Ser Thr Val Val Ala Lys Lys
1460                1465                1470 ata ctg gag gaa att ttt cca aga ttt gga ata cct aag gta ata      5057
Ile Leu Glu Glu Ile Phe Pro Arg Phe Gly Ile Pro Lys Val Ile
1475                1480                1485 ggg tca gac aat ggt cca gct ttc gtt gcc cag gta agt cag gga      5102
Gly Ser Asp Asn Gly Pro Ala Phe Val Ala Gln Val Ser Gln Gly
1490                1495                1500 ctg gcc aag ata ttg ggg att gat tgg aaa ctg cat tgt gca tac      5147
Leu Ala Lys Ile Leu Gly Ile Asp Trp Lys Leu His Cys Ala Tyr
1505                1510                1515 aga ccc caa agc tca gga cag gta gag agg atg aat aga acc att      5192
Arg Pro Gln Ser Ser Gly Gln Val Glu Arg Met Asn Arg Thr Ile
1520                1525                1530 aaa gag acc ctt acc aaa ttg acc aca gag act ggc att aat gat      5237
Lys Glu Thr Leu Thr Lys Leu Thr Thr Glu Thr Gly Ile Asn Asp
1535                1540                1545 tgg atg gct ctc ctg ccc ttt gtg ctt ttt agg gtg agg aac acc      5282
Trp Met Ala Leu Leu Pro Phe Val Leu Phe Arg Val Arg Asn Thr
1550                1555                1560 cct gga cag ttt ggg ctg acc ccc tat gaa ttg ctc tac ggg gga      5327
Pro Gly Gln Phe Gly Leu Thr Pro Tyr Glu Leu Leu Tyr Gly Gly
1565                1570                1575
```

|  |  |  |
|---|---|---|
| ccc ccc ccg ttg gca gaa att gcc ttt gca cat agt gct gat gtg<br>Pro Pro Pro Leu Ala Glu Ile Ala Phe Ala His Ser Ala Asp Val<br>1580                              1585                        1590 | | 5372 |
| ctg ctt tcc cag cct ttg ttc tct agg ctc aag gcg ctc gag tgg<br>Leu Leu Ser Gln Pro Leu Phe Ser Arg Leu Lys Ala Leu Glu Trp<br>1595                              1600                        1605 | | 5417 |
| gtg agg cag cga gcg tgg aag cag ctc cgg gag gcc tac tca gga<br>Val Arg Gln Arg Ala Trp Lys Gln Leu Arg Glu Ala Tyr Ser Gly<br>1610                              1615                        1620 | | 5462 |
| gga gac ttg caa gtt cca cat cgc ttc caa gtt gga gat tca gtc<br>Gly Asp Leu Gln Val Pro His Arg Phe Gln Val Gly Asp Ser Val<br>1625                              1630                        1635 | | 5507 |
| tat gtt aga cgc cac cgt gca gga aac ctc gag act cgg tgg aag<br>Tyr Val Arg Arg His Arg Ala Gly Asn Leu Glu Thr Arg Trp Lys<br>1640                              1645                        1650 | | 5552 |
| gga cct tat ctc gta ctt ttg acc aca cca acg gct gtg aaa gtc<br>Gly Pro Tyr Leu Val Leu Leu Thr Thr Pro Thr Ala Val Lys Val<br>1655                              1660                        1665 | | 5597 |
| gaa gga atc ccc acc tgg atc cat gca tcc cac gtt aag ccg gcg<br>Glu Gly Ile Pro Thr Trp Ile His Ala Ser His Val Lys Pro Ala<br>1670                              1675                        1680 | | 5642 |
| cca cct ccc gac tcg ggg tgg aga gcc gaa aag act gag aat ccc<br>Pro Pro Pro Asp Ser Gly Trp Arg Ala Glu Lys Thr Glu Asn Pro<br>1685                              1690                        1695 | | 5687 |
| ctt aag ctt cgc ctc cat cgc ctg gtt cct tac tct aac aat aac<br>Leu Lys Leu Arg Leu His Arg Leu Val Pro Tyr Ser Asn Asn Asn<br>1700                              1705                        1710 | | 5732 |
| tcc cca ggc cag tagtaaacgc cttatagaca gctcgaaccc ccatagacct<br>Ser Pro Gly Gln<br>1715 | | 5784 |
| ttatcccttca cctggctgat tattgaccct gatacgggtg tcactgtaaa tagcactcga | | 5844 |
| ggtgttgctc ctagaggcac ctggtggcct gaactgcatt tctgcctccg attgattaac | | 5904 |
| cccgctgtta aaagcacacc tcccaaccta gtccgtagtt atgggttcta ttgctgccca | | 5964 |
| ggcacagaga aagagaaata ctgtgggggt tctggggaat ccttctgtag gagatggagc | | 6024 |
| tgcgtcacct ccaacgatgg agactggaaa tggccgatct ctctccagga ccgggtaaaa | | 6084 |
| ttctcctttg tcaattccgg cccgggcaag tacaaaatga tgaaactata taagataag | | 6144 |
| agctgctccc catcagactt agattatcta agataagtt tcactgaaag gaaaacagga | | 6204 |
| aaatattcaa aagtggataa atggtatgag ctggggaata gttttttatt atatggcggg | | 6264 |
| ggagcagggt ccactttaac cattcgcctt aggatagaga cggggacaga accccctgtg | | 6324 |
| gcaatgggac ccgataaagt actggctgaa caggggcccc cggccctgga gccaccgcat | | 6384 |
| aacttgccgg tgcccaatt aacctcgctg cggcctgaca taacacagcc gcctagcaac | | 6444 |
| agtaccactg gattgattcc taccaacacg cctagaaact ccccaggtgt tcctgttaag | | 6504 |
| acaggacaga gactcttcag tctcatccag ggagctttcc aagccatcaa ctccaccgac | | 6564 |
| cctgatgcca cttcttcttg ttggctttgt ctatcctcag ggcctcctta ttatgagggg | | 6624 |
| atggctaaag aaagaaaatt caatgtgacc aaagagcata gaaatcaatg tacatggggg | | 6684 |
| tcccgaaata agcttaccct cactgaagtt ccgggaagg ggacatgcat aggaaaagct | | 6744 |
| cccccatccc accaacacct ttgctatagt actgtggttt atgagcaggc ctcagaaaat | | 6804 |
| cagtatttag tacctggtta taacaggtgg tgggcatgca atactgggtt aacccctgt | | 6864 |
| gtttccacct cagtcttcaa ccaatccaaa gatttctgtg tcatggtcca aatcgtcccc | | 6924 |
| cgagtgtact accatcctga ggaagtggtc cttgatgaat atgactatcg gtataaccga | | 6984 |

-continued

```
ccaaaaagag aacccgtatc ccttacccta gctgtaatgc tcggattagg gacggccgtt    7044
ggcgtaggaa cagggacagc tgccctgatc acaggaccac agcagctaga gaaaggactt    7104
ggtgagctac atgcggccat gacagaagat ctccgagcct taaaggagtc tgttagcaac    7164
ctagaagagt ccctgacttc tttgtctgaa gtggttctac agaaccggag gggattagat    7224
ctgctgtttc taagagaagg tggttatgt gcagccttaa aagaagaatg ttgcttctat    7284
gtagatcact caggagccat cagagactcc atgaacaagc ttagaaaaaa gttagagagg    7344
cgtcgaaggg aaagagaggc tgaccagggg tggtttgaag gatggttcaa caggtctcct    7404
tggatgacca ccctgctttc tgctctgacg gggcccctag tagtcctgct cctgttactt    7464
acagttgggc cttgcttaat taataggttt gttgcctttg ttagagaacg agtgagtgca    7524
gtccagatca tggtacttag gcaacagtac caaggccttc tgagccaagg agaaactgac    7584
ctctagcctt cccagttcta agattagaac tattaacaag acaagaagtg gggaatgaaa    7644
ggatgaaaat gcaacctaac cctcccagaa cccaggaagt taataaaaag ctctaaatgc    7704
ccccgaatta cagaccctgc tggctgccag taaataggta gaaggtcaca cttcctattg    7764
ttccagggcc tgctatcctg gcctaagtaa gataacagga aatgagttga ctaatcgctt    7824
atctggattc tgtaaaactg actggcacca tagaagaatt gattacacat tgacagccct    7884
agtgacctat ctcaactgca atctgtcact ctgcccagga gcccacgcag atgcggacct    7944
ccggagctat tttaaaatga ttggtccacg gagcgcgggc tctcgatatt ttaaaatgat    8004
tggtccatgg agcgcgggct ctcgatattt taaaatgatt ggtttgtgac gcacaggctt    8064
tgttgtgaac cccataaaag ctgtcccgat tccgcactcg gggccgcagt cctctacccc    8124
tgcgtggtgt acgactgtgg gccccagcgc gcttggaata aaaatcctct tgctgtttgc    8184
atcaaaaaaa aaaaaaaaaa aaaaa                                          8209
```

<210> SEQ ID NO 4
<211> LENGTH: 524
<212> TYPE: PRT
<213> ORGANISM: Porcine retrovirus

<400> SEQUENCE: 4

```
Met Gly Gln Thr Val Thr Thr Pro Leu Ser Leu Thr Leu Asp His Trp
  1               5                  10                  15

Thr Glu Val Arg Ser Arg Ala His Asn Leu Ser Val Gln Val Lys Lys
             20                  25                  30

Gly Pro Trp Gln Thr Phe Cys Ala Ser Glu Trp Pro Thr Phe Asp Val
         35                  40                  45

Gly Trp Pro Ser Glu Gly Thr Phe Asn Ser Glu Ile Ile Leu Ala Val
     50                  55                  60

Lys Ala Ile Ile Phe Gln Thr Gly Pro Gly Ser His Pro Asp Gln Glu
 65                  70                  75                  80

Pro Tyr Ile Leu Thr Trp Gln Asp Leu Ala Glu Asp Pro Pro Pro Trp
                 85                  90                  95

Val Lys Pro Trp Leu Asn Lys Pro Arg Lys Pro Gly Pro Arg Ile Leu
            100                 105                 110

Ala Leu Gly Glu Lys Asn Lys His Ser Ala Glu Lys Val Glu Pro Ser
        115                 120                 125

Ser Ser Tyr Leu Pro Arg Asp Arg Gly Ala Ala Asp Leu Ala Gly Thr
    130                 135                 140

Pro Thr Cys Ser Pro Thr Pro Leu Ser Ser Thr Gly Cys Cys Glu Gly
```

-continued

```
            145                 150                 155                 160
        Thr Ser Ala Pro Pro Gly Ala Pro Val Val Glu Gly Pro Ala Ala Gly
                        165                 170                 175
        Thr Arg Ser Arg Arg Gly Ala Thr Pro Glu Arg Thr Asp Glu Ile Ala
                    180                 185                 190
        Ile Leu Pro Leu Arg Thr Tyr Gly Pro Pro Met Pro Gly Gly Gln Leu
                    195                 200                 205
        Gln Pro Leu Gln Tyr Trp Pro Phe Ser Ser Ala Asp Leu Tyr Asn Trp
                210                 215                 220
        Lys Thr Asn His Pro Pro Phe Ser Glu Asp Pro Gln Arg Leu Thr Gly
        225                 230                 235                 240
        Leu Val Glu Ser Leu Met Phe Ser His Gln Pro Thr Trp Asp Asp Cys
                        245                 250                 255
        Gln Gln Leu Leu Gln Thr Leu Phe Thr Thr Glu Glu Arg Glu Arg Ile
                    260                 265                 270
        Leu Leu Glu Ala Arg Lys Asn Val Pro Gly Ala Asp Gly Arg Pro Thr
                275                 280                 285
        Gln Leu Gln Asn Glu Ile Asp Met Gly Phe Pro Leu Thr Arg Pro Gly
                290                 295                 300
        Trp Asp Tyr Asn Thr Ala Glu Gly Arg Glu Ser Leu Lys Ile Tyr Arg
        305                 310                 315                 320
        Gln Ala Leu Val Ala Gly Leu Arg Gly Ala Ser Arg Arg Pro Thr Asn
                        325                 330                 335
        Leu Ala Lys Val Arg Glu Val Met Gln Gly Pro Asn Glu Pro Pro Ser
                    340                 345                 350
        Val Phe Leu Glu Arg Leu Met Glu Ala Phe Arg Arg Phe Thr Pro Phe
                    355                 360                 365
        Asp Pro Thr Ser Glu Ala Gln Lys Ala Ser Val Ala Leu Ala Phe Ile
                370                 375                 380
        Gly Gln Ser Ala Leu Asp Ile Arg Lys Lys Leu Gln Arg Leu Glu Gly
        385                 390                 395                 400
        Leu Gln Glu Ala Glu Leu Arg Asp Leu Val Arg Glu Ala Glu Lys Val
                        405                 410                 415
        Tyr Tyr Arg Arg Glu Thr Glu Glu Lys Glu Gln Arg Lys Glu Lys
                    420                 425                 430
        Glu Arg Glu Glu Arg Glu Arg Arg Asp Arg Arg Gln Glu Lys Asn
                    435                 440                 445
        Leu Thr Lys Ile Leu Ala Ala Val Val Glu Gly Lys Ser Ser Arg Glu
                450                 455                 460
        Arg Glu Arg Asp Phe Arg Lys Ile Arg Ser Gly Pro Arg Gln Ser Gly
        465                 470                 475                 480
        Asn Leu Gly Asn Arg Thr Pro Leu Asp Lys Asp Gln Cys Ala Tyr Cys
                        485                 490                 495
        Lys Glu Lys Gly His Trp Ala Arg Asn Cys Pro Lys Lys Gly Asn Lys
                    500                 505                 510
        Gly Pro Lys Val Leu Ala Leu Glu Glu Asp Lys Asp
                    515                 520
```

<210> SEQ ID NO 5
<211> LENGTH: 1194
<212> TYPE: PRT
<213> ORGANISM: Porcine retrovirus

<400> SEQUENCE: 5

-continued

```
Gly Arg Arg Gly Ser Asp Pro Leu Pro Glu Pro Arg Val Thr Leu Lys
  1               5                  10                  15

Val Glu Gly Gln Pro Val Glu Phe Leu Val Asp Thr Gly Ala Glu His
             20                  25                  30

Ser Val Leu Leu Gln Pro Leu Gly Lys Leu Lys Glu Lys Lys Ser Trp
         35                  40                  45

Val Met Gly Ala Thr Gly Gln Arg Gln Tyr Pro Trp Thr Thr Arg Arg
     50                  55                  60

Thr Val Asp Leu Gly Val Gly Arg Val Thr His Ser Phe Leu Val Ile
 65                  70                  75                  80

Pro Glu Cys Pro Val Pro Leu Leu Gly Arg Asp Leu Leu Thr Lys Met
             85                  90                  95

Gly Ala Gln Ile Ser Phe Glu Gln Gly Arg Pro Glu Val Ser Val Asn
            100                 105                 110

Asn Lys Pro Ile Thr Val Leu Thr Leu Gln Leu Asp Asp Glu Tyr Arg
        115                 120                 125

Leu Tyr Ser Pro Gln Val Lys Pro Asp Gln Asp Ile Gln Ser Trp Leu
    130                 135                 140

Glu Gln Phe Pro Gln Ala Trp Ala Glu Thr Ala Gly Met Gly Leu Ala
145                 150                 155                 160

Lys Gln Val Pro Gln Val Ile Gln Leu Lys Ala Ser Ala Thr Pro
                165                 170                 175

Val Ser Val Arg Gln Tyr Pro Leu Ser Arg Glu Ala Arg Glu Gly Ile
                180                 185                 190

Trp Pro His Val Gln Arg Leu Ile Gln Gln Gly Ile Leu Val Pro Val
        195                 200                 205

Gln Ser Pro Trp Asn Thr Pro Leu Leu Pro Val Arg Lys Pro Gly Thr
    210                 215                 220

Asn Asp Tyr Arg Pro Val Gln Asp Leu Arg Glu Val Asn Lys Arg Val
225                 230                 235                 240

Gln Asp Ile His Pro Thr Val Pro Asn Pro Tyr Asn Leu Leu Ser Ala
                245                 250                 255

Leu Pro Pro Glu Arg Asn Trp Tyr Thr Val Leu Asp Leu Lys Asp Ala
                260                 265                 270

Phe Phe Cys Leu Arg Leu His Pro Thr Ser Gln Pro Leu Phe Ala Phe
        275                 280                 285

Glu Trp Arg Asp Pro Gly Thr Gly Arg Thr Gly Gln Leu Thr Trp Thr
290                 295                 300

Arg Leu Pro Gln Gly Phe Lys Asn Ser Pro Thr Ile Phe Asp Glu Ala
305                 310                 315                 320

Leu His Arg Asp Leu Ala Asn Phe Arg Ile Gln His Pro Gln Val Thr
                325                 330                 335

Leu Leu Gln Tyr Val Asp Asp Leu Leu Leu Ala Gly Ala Thr Lys Gln
                340                 345                 350

Asp Cys Leu Glu Gly Thr Lys Ala Leu Leu Leu Glu Leu Ser Asp Leu
        355                 360                 365

Gly Tyr Arg Ala Ser Ala Lys Lys Ala Gln Ile Cys Arg Arg Glu Val
    370                 375                 380

Thr Tyr Leu Gly Tyr Ser Leu Arg Gly Gly Gln Arg Trp Leu Thr Glu
385                 390                 395                 400

Ala Arg Lys Lys Thr Val Val Gln Ile Pro Ala Pro Thr Thr Ala Lys
                405                 410                 415

Gln Val Arg Glu Phe Leu Gly Thr Ala Gly Phe Cys Arg Leu Trp Ile
```

-continued

```
            420             425             430
Pro Gly Phe Ala Thr Leu Ala Ala Pro Leu Tyr Pro Leu Thr Lys Glu
        435             440             445
Lys Gly Gly Phe Ser Trp Ala Pro Glu His Gln Lys Ala Phe Asp Ala
    450             455             460
Ile Lys Lys Ala Leu Leu Ser Ala Pro Ala Leu Ala Leu Pro Asp Val
465             470             475             480
Thr Lys Pro Phe Thr Leu Tyr Val Asp Glu Arg Lys Gly Val Ala Arg
                485             490             495
Gly Val Leu Thr Gln Thr Leu Gly Pro Trp Arg Pro Val Ala Tyr
            500             505             510
Leu Ser Lys Lys Leu Asp Pro Val Ala Ser Gly Trp Pro Val Cys Leu
        515             520             525
Lys Ala Ile Ala Ala Val Ala Ile Leu Val Lys Asp Ala Asp Lys Leu
    530             535             540
Thr Leu Gly Gln Asn Ile Thr Val Ile Ala Pro His Ala Leu Glu Asn
545             550             555             560
Ile Val Arg Gln Pro Pro Asp Arg Trp Met Thr Asn Ala Arg Met Thr
                565             570             575
His Tyr Gln Ser Leu Leu Leu Thr Glu Arg Val Thr Phe Ala Pro Pro
            580             585             590
Ala Ala Leu Asn Pro Ala Thr Leu Leu Pro Glu Glu Thr Asp Glu Pro
        595             600             605
Val Thr His Asp Cys His Gln Leu Leu Ile Glu Thr Gly Val Arg
    610             615             620
Lys Asp Leu Thr Asp Ile Pro Leu Thr Gly Glu Val Leu Thr Trp Phe
625             630             635             640
Thr Asp Gly Ser Ser Tyr Val Val Glu Gly Lys Arg Met Ala Gly Ala
                645             650             655
Ala Val Val Asp Gly Thr Arg Thr Ile Trp Ala Ser Ser Leu Pro Glu
            660             665             670
Gly Thr Ser Ala Gln Lys Ala Glu Leu Met Ala Leu Thr Gln Ala Leu
        675             680             685
Arg Leu Ala Glu Gly Lys Ser Ile Asn Ile Tyr Thr Asp Ser Arg Tyr
    690             695             700
Ala Phe Ala Thr Ala His Val His Gly Ala Ile Tyr Lys Gln Arg Gly
705             710             715             720
Leu Leu Thr Ser Ala Gly Arg Glu Ile Lys Asn Lys Glu Glu Ile Leu
                725             730             735
Ser Leu Leu Glu Ala Leu His Leu Pro Lys Arg Leu Ala Ile Ile His
            740             745             750
Cys Pro Gly His Gln Lys Ala Lys Asp Leu Ile Ser Arg Gly Asn Gln
        755             760             765
Met Ala Asp Arg Val Ala Lys Gln Ala Gln Ala Val Asn Leu Leu
    770             775             780
Pro Ile Ile Glu Thr Pro Lys Ala Pro Glu Pro Arg Arg Gln Tyr Thr
785             790             795             800
Leu Glu Asp Trp Gln Glu Ile Lys Lys Ile Asp Gln Phe Ser Glu Thr
                805             810             815
Pro Glu Gly Thr Cys Tyr Thr Ser Tyr Gly Lys Glu Ile Leu Pro His
            820             825             830
Lys Glu Gly Leu Glu Tyr Val Gln Gln Ile His Arg Leu Thr His Leu
        835             840             845
```

```
Gly Thr Lys His Leu Gln Gln Leu Val Arg Thr Ser Pro Tyr His Val
    850                 855                 860

Leu Arg Leu Pro Gly Val Ala Asp Ser Val Val Lys His Cys Val Pro
865                 870                 875                 880

Cys Gln Leu Val Asn Ala Asn Pro Ser Arg Ile Pro Pro Gly Lys Arg
                885                 890                 895

Leu Arg Gly Ser His Pro Gly Ala His Trp Glu Val Asp Phe Thr Glu
            900                 905                 910

Val Lys Pro Ala Lys Tyr Gly Asn Lys Tyr Leu Leu Val Phe Val Asp
        915                 920                 925

Thr Phe Ser Gly Trp Val Glu Ala Tyr Pro Thr Lys Lys Glu Thr Ser
    930                 935                 940

Thr Val Val Ala Lys Lys Ile Leu Glu Glu Ile Phe Pro Arg Phe Gly
945                 950                 955                 960

Ile Pro Lys Val Ile Gly Ser Asp Asn Gly Pro Ala Phe Val Ala Gln
                965                 970                 975

Val Ser Gln Gly Leu Ala Lys Ile Leu Gly Ile Asp Trp Lys Leu His
            980                 985                 990

Cys Ala Tyr Arg Pro Gln Ser Ser Gly Gln Val Glu Arg Met Asn Arg
        995                 1000                1005

Thr Ile Lys Glu Thr Leu Thr Lys Leu Thr Thr Glu Thr Gly Ile Asn
    1010                1015                1020

Asp Trp Met Ala Leu Leu Pro Phe Val Leu Phe Arg Val Arg Asn Thr
1025                1030                1035                1040

Pro Gly Gln Phe Gly Leu Thr Pro Tyr Glu Leu Leu Tyr Gly Gly Pro
                1045                1050                1055

Pro Pro Leu Ala Glu Ile Ala Phe Ala His Ser Ala Asp Val Leu Leu
            1060                1065                1070

Ser Gln Pro Leu Phe Ser Arg Leu Lys Ala Leu Glu Trp Val Arg Gln
        1075                1080                1085

Arg Ala Trp Lys Gln Leu Arg Glu Ala Tyr Ser Gly Gly Asp Leu Gln
    1090                1095                1100

Val Pro His Arg Phe Gln Val Gly Asp Ser Val Tyr Val Arg Arg His
1105                1110                1115                1120

Arg Ala Gly Asn Leu Glu Thr Arg Trp Lys Gly Pro Tyr Leu Val Leu
                1125                1130                1135

Leu Thr Thr Pro Thr Ala Val Lys Val Glu Gly Ile Pro Thr Trp Ile
            1140                1145                1150

His Ala Ser His Val Lys Pro Ala Pro Pro Asp Ser Gly Trp Arg
        1155                1160                1165

Ala Glu Lys Thr Glu Asn Pro Leu Lys Leu Arg Leu His Arg Leu Val
    1170                1175                1180

Pro Tyr Ser Asn Asn Asn Ser Pro Gly Gln
1185                1190

<210> SEQ ID NO 6
<211> LENGTH: 656
<212> TYPE: PRT
<213> ORGANISM: Porcine retrovirus

<400> SEQUENCE: 6

Met His Pro Thr Leu Ser Arg Arg His Leu Pro Thr Arg Gly Gly Glu
1               5                   10                  15

Pro Lys Arg Leu Arg Ile Pro Leu Ser Phe Ala Ser Ile Ala Trp Phe
```

```
                    20                  25                  30
Leu Thr Leu Thr Ile Thr Pro Gln Ala Ser Ser Lys Arg Leu Ile Asp
            35                  40                  45

Ser Ser Asn Pro His Arg Pro Leu Ser Leu Thr Trp Leu Ile Ile Asp
        50                  55                  60

Pro Asp Thr Gly Val Thr Val Asn Ser Thr Arg Gly Val Ala Pro Arg
65                      70                  75                  80

Gly Thr Trp Trp Pro Glu Leu His Phe Cys Leu Arg Leu Ile Asn Pro
                    85                  90                  95

Ala Val Lys Ser Thr Pro Pro Asn Leu Val Arg Ser Tyr Gly Phe Tyr
                100                 105                 110

Cys Cys Pro Gly Thr Glu Lys Glu Lys Tyr Cys Gly Gly Ser Gly Glu
                115                 120                 125

Ser Phe Cys Arg Arg Trp Ser Cys Val Thr Ser Asn Asp Gly Asp Trp
            130                 135                 140

Lys Trp Pro Ile Ser Leu Gln Asp Arg Val Lys Phe Ser Phe Val Asn
145                 150                 155                 160

Ser Gly Pro Gly Lys Tyr Lys Met Met Lys Leu Tyr Lys Asp Lys Ser
                    165                 170                 175

Cys Ser Pro Ser Asp Leu Asp Tyr Leu Lys Ile Ser Phe Thr Glu Arg
                180                 185                 190

Lys Thr Gly Lys Tyr Ser Lys Val Asp Lys Trp Tyr Glu Leu Gly Asn
                195                 200                 205

Ser Phe Leu Leu Tyr Gly Gly Ala Gly Ser Thr Leu Thr Ile Arg
        210                 215                 220

Leu Arg Ile Glu Thr Gly Thr Glu Pro Pro Val Ala Met Gly Pro Asp
225                 230                 235                 240

Lys Val Leu Ala Glu Gln Gly Pro Pro Ala Leu Glu Pro Pro His Asn
                    245                 250                 255

Leu Pro Val Pro Gln Leu Thr Ser Leu Arg Pro Asp Ile Thr Gln Pro
                260                 265                 270

Pro Ser Asn Ser Thr Thr Gly Leu Ile Pro Thr Asn Thr Pro Arg Asn
            275                 280                 285

Ser Pro Gly Val Pro Val Lys Thr Gly Gln Arg Leu Phe Ser Leu Ile
        290                 295                 300

Gln Gly Ala Phe Gln Ala Ile Asn Ser Thr Asp Pro Asp Ala Thr Ser
305                 310                 315                 320

Ser Cys Trp Leu Cys Leu Ser Ser Gly Pro Pro Tyr Tyr Glu Gly Met
                    325                 330                 335

Ala Lys Glu Arg Lys Phe Asn Val Thr Lys Glu His Arg Asn Gln Cys
                340                 345                 350

Thr Trp Gly Ser Arg Asn Lys Leu Thr Leu Thr Glu Val Ser Gly Lys
            355                 360                 365

Gly Thr Cys Ile Gly Lys Ala Pro Pro Ser His Gln His Leu Cys Tyr
        370                 375                 380

Ser Thr Val Val Tyr Glu Gln Ala Ser Glu Asn Gln Tyr Leu Val Pro
385                 390                 395                 400

Gly Tyr Asn Arg Trp Trp Ala Cys Asn Thr Gly Leu Thr Pro Cys Val
                    405                 410                 415

Ser Thr Ser Val Phe Asn Gln Ser Lys Asp Phe Cys Val Met Val Gln
                420                 425                 430

Ile Val Pro Arg Val Tyr Tyr His Pro Glu Glu Val Val Leu Asp Glu
            435                 440                 445
```

```
Tyr Asp Tyr Arg Tyr Asn Arg Pro Lys Arg Glu Pro Val Ser Leu Thr
    450                 455                 460
Leu Ala Val Met Leu Gly Leu Gly Thr Ala Val Gly Val Gly Thr Gly
465                 470                 475                 480
Thr Ala Ala Leu Ile Thr Gly Pro Gln Gln Leu Glu Lys Gly Leu Gly
            485                 490                 495
Glu Leu His Ala Ala Met Thr Glu Asp Leu Arg Ala Leu Lys Glu Ser
        500                 505                 510
Val Ser Asn Leu Glu Glu Ser Leu Thr Ser Leu Ser Glu Val Val Leu
    515                 520                 525
Gln Asn Arg Arg Gly Leu Asp Leu Leu Phe Leu Arg Glu Gly Gly Leu
    530                 535                 540
Cys Ala Ala Leu Lys Glu Cys Cys Phe Tyr Val Asp His Ser Gly
545                 550                 555                 560
Ala Ile Arg Asp Ser Met Asn Lys Leu Arg Lys Lys Leu Glu Arg Arg
            565                 570                 575
Arg Arg Glu Arg Glu Ala Asp Gln Gly Trp Phe Glu Gly Trp Phe Asn
        580                 585                 590
Arg Ser Pro Trp Met Thr Thr Leu Leu Ser Ala Leu Thr Gly Pro Leu
    595                 600                 605
Val Val Leu Leu Leu Leu Thr Val Gly Pro Cys Leu Ile Asn Arg
    610                 615                 620
Phe Val Ala Phe Val Arg Glu Arg Val Ser Ala Val Gln Ile Met Val
625                 630                 635                 640
Leu Arg Gln Gln Tyr Gln Gly Leu Leu Ser Gln Gly Glu Thr Asp Leu
            645                 650                 655

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide designed against Porcine retrovirus genome

<400> SEQUENCE: 7
ggaagtggac ttcactga                                              18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide designed against Porcine retrovirus genome

<400> SEQUENCE: 8
ctttccaccc cgaatcgg                                              18

<210> SEQ ID NO 9
<211> LENGTH: 2956
<212> TYPE: DNA
<213> ORGANISM: Unknown Organism
<220> FEATURE:
<223> OTHER INFORMATION: Description of Unknown Organism: Genomic "Raji"
      clone DNA ENV region

<400> SEQUENCE: 9 tgcttttag ggttaggaac acccctggac agtttgggct gaccccctat gaattgctct    60
```

```
acgggggacc cccccgttg gtagaaattg cttctgtaca tagtgctgat gtgctgcttt      120
cccagccttt gttctctagg ctcaaggcgc tcgagtgggt gaggcaacga gcgtggaagc      180
agctccggga ggcctactca ggagagagag acttgcaagt tccacatcgc ttccaagttg      240
gagattcagt ctatgttaga cgccaccgtg caggaaacct cgagactcgg tggaagggac      300
cttatctcgt acttttgacc acaccaacg ctgtgaaagt cgaaggaatc tccacctgga      360
tccatgcatc ccacgttaag ctggcgccac ctcccgactc ggggtggaga gccgaaaaga      420
ctgagaatcc ccttaagctt cgcctccatc gcctggttcc ttactctaac aataactccc      480
caggccagta gtaaacgcct tatagacagc tcgaacccc atagacctt atcccctacc       540 tggctgatta ttgaccctga tacgggtgtc actgtaaata gcactcgagg tgttgctcct      600
agaggcacct ggtggcctga actgcatttc tgcctccgat tgattaaccc cgctgttaaa      660
agcacacctc ccaacctagt ccgtagttat gggttctatt gctgcccagg cacagagaaa      720
gagaaatact gtgggggttc tggggaatcc ttctgtagga gatggagctg cgtcacctcc      780
aacgatggag actggaaatg gccgatctct ctccaggacc gggtaaaatt ctcctttgtc      840
aattccggcc cgggcaagta caaaatgatg aaactatata aagataagag ctgctcccca      900
tcagacttag attatctaaa gataagtttc actgaaaaag gaaaacagga aaatattcaa      960
aagtggataa atggtatgag ctggggaata gttttttaat aatatggcgg gggagcaggg     1020
tccactttaa ccattcgcct taggatagag acggggacag aaccccctgt ggcaatggga     1080
cccgataaag tactggctga acaggggccc ccggccctgg agccaccgca taacttgccg     1140
gtgccccaat taacctcgct gcggcctgac ataacacagc cgcctagcaa cagtaccact     1200
ggattgattc ctaccaacac gcctagaaac tccccaggtg ttcctgttaa dacaggacag     1260
agactcttca gtctcatcca gggagctttc caagccatca actccaccga ccctgatgcc     1320
acttcttctt gttggcttg tctatcctca gggcctcctt attatgaggg gatggctaaa     1380
gaaagaaaat tcaatgtgac caaagagcat agaaatcaat gtacatgggg gtcccgaaat     1440
aagcttaccc tcactgaagt ttccgggaag gggacatgca taggaaaagc tcccccatcc     1500
caccaacacc tttgctatag tactgtggtt tatgagcagg cctcagaaaa tcagtattta     1560
gtacctggtt ataacaggtg gtgggcatgc aatactgggt taaccccctg tgtttccacc     1620
tcagtcttca accaatccaa agatttgtgt gtcatggtcc aaatcgtccc ccgagtgtac     1680
taccatcctg aggaagtggt ccttgatgaa tatgactatc ggtataaccg accaaaaaga     1740
gaacccgtat cccttaccct agctgtaatg ctcggattag ggacggccgt tggcgtagga     1800
acagggacag ctgccctgat cacaggacca cagcagctag agaaaggact tggtgagcta     1860
catgcggcca tgacagaaga tctccgagcc ttaaaggagt ctgttagcaa cctagaagag     1920
tccctgactt ctttgtctga agtggttcta cagaaccgga ggggattaga tctgctgttt     1980
ctaagagaag gtgggttatg tgcagcctta aagaagaat gttgcttcta tgtagatcac     2040
tcaggagcca tcagagactc catgaacaag cttagaaaaa agttagagag gcgtcgaagg     2100
gaaagagagg ctgaccaggg gtggtttgaa ggatggttca acaggtctcc ttggatgacc     2160
accctgcttt ctgctctgac ggggccccta gtagtcctgc tcctgttact tacagttggg     2220
ccttgcttaa ttaataggtt tgttgccttt gttagagaac gagtgagtgc agtccagatc     2280
atggtactta ggcaacagta ccaaggcctt ctgagccaag gagaaactga cctctagcct     2340
tcccagttct aagattagaa ctattaacaa gacaagaagt ggggaatgaa aggatgaaaa     2400
tgcaacctaa ccctcccaga acccaggaag ttaataaaaa gctctaaatg cccccgaatt     2460
```

-continued

```
acagaccctg ctggctgcca gtaaataggt agaaggtcac acttcctatt gttccagggc    2520
ctgctatcct ggcctaagta agataacagg aaatgagttg actaatcgct tatctggatt    2580
ctgtaaaact gactggcacc atagaagaat tgattacaca ttgacagccc tagtgaccta    2640
tctcaactgc aatctgtcac tctgcccagg agcccacgca gatgcggacc tccggagcta    2700 tttttaaaatg attggtccac ggagcgcggg ctctcgatat tttaaaatga ttggtccatg    2760
gagcgcgggc tctcgatatt ttaaaatgat tggtttgtga cgcacaggct ttgttgtgaa    2820
ccccataaaa gctgtcccga ttccgcactc ggggccgcag tcctctaccc ctgcgtggtg    2880
tacgactgtg ggccccagcg cgcttggaat aaaaatcctc ttgctgtttg catcaaaaaa    2940
aaaaaaaaaa aaaaa                                                     2956
```

<210> SEQ ID NO 10
<211> LENGTH: 657
<212> TYPE: PRT
<213> ORGANISM: Unknown Organism
<220> FEATURE:
<223> OTHER INFORMATION: Description of Unknown Organism: Amino acid sequence of ENV region "Raji"

<400> SEQUENCE: 10

```
Met His Pro Thr Leu Ser Trp Arg His Leu Pro Thr Arg Gly Gly Glu
  1               5                  10                  15

Pro Lys Arg Leu Arg Ile Pro Leu Ser Phe Ala Ser Ile Ala Trp Phe
             20                  25                  30

Leu Thr Leu Thr Ile Thr Pro Gln Ala Ser Ser Lys Arg Leu Ile Asp
         35                  40                  45

Ser Ser Asn Pro His Arg Pro Leu Ser Pro Thr Trp Leu Ile Ile Asp
     50                  55                  60

Pro Asp Thr Gly Val Thr Val Asn Ser Thr Arg Gly Val Ala Pro Arg
 65                  70                  75                  80

Gly Thr Trp Trp Pro Glu Leu His Phe Cys Leu Arg Leu Ile Asn Pro
                 85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Gly Glu
        115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Met Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
        195                 200                 205

Ile Val Phe Tyr Lys Tyr Gly Gly Gly Ala Gly Ser Thr Leu Thr Ile
    210                 215                 220

Arg Leu Arg Ile Glu Thr Gly Thr Glu Pro Val Ala Met Gly Pro
225                 230                 235                 240

Asp Lys Val Leu Ala Glu Gln Gly Pro Pro Ala Leu Glu Pro His
                245                 250                 255

Asn Leu Pro Val Pro Gln Leu Thr Ser Leu Arg Pro Asp Ile Thr Gln
```

-continued

```
                        260                     265                     270
        Pro Pro Ser Asn Ser Thr Thr Gly Leu Ile Pro Thr Asn Thr Pro Arg
                    275                     280                     285
        Asn Ser Pro Gly Val Pro Val Lys Thr Gly Gln Arg Leu Phe Ser Leu
                    290                     295                     300
        Ile Gln Gly Ala Phe Gln Ala Ile Asn Ser Thr Asp Pro Asp Ala Thr
        305                     310                     315                     320
        Ser Ser Cys Trp Leu Cys Leu Ser Ser Gly Pro Pro Tyr Tyr Glu Gly
                            325                     330                     335
        Met Ala Lys Glu Arg Lys Phe Asn Val Thr Lys Glu His Arg Asn Gln
                        340                     345                     350
        Cys Thr Trp Gly Ser Arg Asn Lys Leu Thr Leu Thr Glu Val Ser Gly
                        355                     360                     365
        Lys Gly Thr Cys Ile Gly Lys Ala Pro Pro Ser His Gln His Leu Cys
                        370                     375                     380
        Tyr Ser Thr Val Val Tyr Glu Gln Ala Ser Glu Asn Gln Tyr Leu Val
        385                     390                     395                     400
        Pro Gly Tyr Asn Arg Trp Trp Ala Cys Asn Thr Gly Leu Thr Pro Cys
                            405                     410                     415
        Val Ser Thr Ser Val Phe Asn Gln Ser Lys Asp Leu Cys Val Met Val
                            420                     425                     430
        Gln Ile Val Pro Arg Val Tyr Tyr His Pro Glu Glu Val Val Leu Asp
                        435                     440                     445
        Glu Tyr Asp Tyr Arg Tyr Asn Arg Pro Lys Arg Glu Pro Val Ser Leu
                    450                     455                     460
        Thr Leu Ala Val Met Leu Gly Leu Gly Thr Ala Val Gly Val Gly Thr
        465                     470                     475                     480
        Gly Thr Ala Ala Leu Ile Thr Gly Pro Gln Gln Leu Glu Lys Gly Leu
                            485                     490                     495
        Gly Glu Leu His Ala Ala Met Thr Glu Asp Leu Arg Ala Leu Lys Glu
                        500                     505                     510
        Ser Val Ser Asn Leu Glu Glu Ser Leu Thr Ser Leu Ser Glu Val Val
                    515                     520                     525
        Leu Gln Asn Arg Arg Gly Leu Asp Leu Leu Phe Leu Arg Glu Gly Gly
        530                     535                     540
        Leu Cys Ala Ala Leu Lys Glu Glu Cys Cys Phe Tyr Val Asp His Ser
        545                     550                     555                     560
        Gly Ala Ile Arg Asp Ser Met Asn Lys Leu Arg Lys Lys Leu Glu Arg
                            565                     570                     575
        Arg Arg Arg Glu Arg Glu Ala Asp Gln Gly Trp Phe Glu Gly Trp Phe
                        580                     585                     590
        Asn Arg Ser Pro Trp Met Thr Thr Leu Leu Ser Ala Leu Thr Gly Pro
                        595                     600                     605
        Leu Val Val Leu Leu Leu Leu Thr Val Gly Pro Cys Leu Ile Asn
                    610                     615                     620
        Arg Phe Val Ala Phe Val Arg Glu Arg Val Ser Ala Val Gln Ile Met
        625                     630                     635                     640
        Val Leu Arg Gln Gln Tyr Gln Gly Leu Leu Ser Gln Gly Glu Thr Asp
                            645                     650                     655
        Leu
```

<210> SEQ ID NO 11
<211> LENGTH: 20

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
gatggctctc ctgcccttg                                              20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
cgatggaggc gaagcttaag g                                           21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
gatggctctc ctgcccttg                                              20

<210> SEQ ID NO 14
<211> LENGTH: 18
<212> TYPE: DNA
<213> ORGANISM: Porcine retrovirus

<400> SEQUENCE: 14
ccacagtcgt acaccacg                                               18

<210> SEQ ID NO 15
<211> LENGTH: 9
<212> TYPE: PRT
<213> ORGANISM: Porcine retrovirus

<400> SEQUENCE: 15

Val Leu Ala Leu Glu Glu Asp Lys Asp
  1               5

<210> SEQ ID NO 16
<211> LENGTH: 5
<212> TYPE: PRT
<213> ORGANISM: Porcine retrovirus

<400> SEQUENCE: 16

Arg Leu Gly Glu Thr
  1               5

<210> SEQ ID NO 17
<211> LENGTH: 673
<212> TYPE: DNA
<213> ORGANISM: Porcine retrovirus

<400> SEQUENCE: 17
aagaagtggg gaatgaaagg atgaaaatgc aacctaaccc tcccagaacc caggaagtta    60
ataaaaagct ctaaatgccc ccgaattmca gaccctgctg gctgccagta aataggtaga   120
```

| | | | | | |
|---|---|---|---|---|---|
| aggtcacact | tcctattgtt | ccagggcctg | ctatcctggc | ctaagtaaga | taacaggaaa | 180 |
| tgagttgact | aatcgcttat | ctggattctg | taaaactgac | tggcaccata | gaagaattga | 240 |
| ttacacattg | acagccctag | tgacctatct | caactgcaat | ctgtcactct | gcccaggagc | 300 |
| ccacgcagat | gcggacctcc | ggagctattt | taaaatgatt | ggtccacgga | gcgcgggctc | 360 |
| tcgatatttt | aaaatgattg | gtccatggag | cgcgggctct | cgatatttta | aaatgattgg | 420 |
| tttgtgacgc | acaggctttg | ttgtgaaccc | cataaaagct | gtcccgattc | cgcactcggg | 480 |
| gccgcagtcc | tctaccoctg | cgtggtgtac | gactgtgggc | cccagcgcgc | ttggaataaa | 540 |
| aatcctcttg | ctgtttgcat | caagaccgct | tctygtgagt | gatttggggt | gtcgcctctt | 600 |
| ccgakcccgg | acgaggggga | ttgttctttt | actggccttt | catttggtgc | gttggccggg | 660 |
| aaatcctgcg | acc | | | | | 673 |